US007569361B2

(12) United States Patent
Chung et al.

(10) Patent No.: US 7,569,361 B2
(45) Date of Patent: Aug. 4, 2009

(54) THROMBOPOIETIN PROTEIN VARIANTS

(75) Inventors: Yong-Hoon Chung, Seoul (KR); Hak-sup Lee, Gangwon-do (KR); Ki-Wan Yi, Gyeonggi-do (KR); Youn-Hwa Heo, Seoul (KR); Jae-Youn Kim, Seoul (KR)

(73) Assignee: Medexgen Co., Ltd., Seoul (KR)

( * ) Notice: Subject to any disclaimer, the term of this patent is extended or adjusted under 35 U.S.C. 154(b) by 0 days.

(21) Appl. No.: 10/519,390

(22) PCT Filed: May 27, 2004

(86) PCT No.: PCT/KR2004/001246

§ 371 (c)(1),
(2), (4) Date: Jul. 29, 2005

(87) PCT Pub. No.: WO2005/010043

PCT Pub. Date: Feb. 3, 2005

(65) Prior Publication Data

US 2006/0008872 A1 Jan. 12, 2006

(30) Foreign Application Priority Data

Jul. 26, 2003 (KR) ...................... 10-2003-0051846

(51) Int. Cl.
*C07K 14/00* (2006.01)
*C07K 14/475* (2006.01)

(52) U.S. Cl. ....................... 435/69.1; 530/350; 530/399

(58) Field of Classification Search ....................... None
See application file for complete search history.

(56) References Cited

U.S. PATENT DOCUMENTS 5,194,596 A * 3/1993 Tischer et al. ............... 530/399
5,350,836 A * 9/1994 Kopchick et al. ........... 530/399
2005/0220800 A1* 10/2005 Scott et al. ............... 424/184.1

OTHER PUBLICATIONS

Benjamin et al., 1998, Development 125:1591-1598.*
Vukicevic et al., 1996, PNAS USA 93:9021-9026.*
Massague, 1987, Cell 49:437-8.*
Pilbeam et al., 1993, Bone 14:717-720.*
Skolnick et al.,2000, Trends in Biotech. 18:34-39.*
Bork. 2000, Genome Research 10:398-400.*
Doerks et al., 1998, Trends in Genetics 14:248-250.*
Smith et al., 1997, Nature Biotechnology 15:1222-1223.*
Brenner. 1999, Trends in Genetics 15:132-133.*
Bork et al., 1996, Trends in Genetics 12:425-427.*
Smulevich et al., Biochemistry 1994; 33(23):7398-7407.*
Smulevich, G., et al. "Characterization of recombinant horseradish peroxidase C and three site-directed mutants, F41V, F41W and R38K, by resonance Raman spectroscopy" Biochemistry, 1994, vol. 33(23): pp. 7398-7407.

(Continued)

*Primary Examiner*—Cherie M Woodward
(74) *Attorney, Agent, or Firm*—Sheridan Ross P.C.

(57) ABSTRACT

Disclosed is a protein variant which substitutes valine for phenylalanine residue in a binding domain having a biological response-modifying function by binding to a receptor, ligand or substrate. Also, the present invention discloses a DNA encoding the protein variant, a recombinant expression vector to which the DNA is operably linked, a host cell transformed or transfected with the recombinant expression vector, and a method of preparing the protein variant comprising cultivating the host cell and isolating the protein variant from the resulting culture. Further, the present invention discloses a pharmaceutical composition comprising the protein variant and a pharmaceutically acceptable carrier.

4 Claims, 29 Drawing Sheets

OTHER PUBLICATIONS

Wu, H., et al., "Kinetic and structural analysis of mutant CD4 receptors that are defective in HIV gp120 binding", Proc. Natl. Acad. Sci. USA, 1996, vol. 93(26): pp. 15030-15035.

Delorme, E., et al., "Role of glycosylation on the secretion and biological activity of erythropoietin", Biochemistry, 1992, vol. 31(41): pp. 9871-9876.

Carakushansky, M., et al., "A new missence mutation in the growth hormone-releasing hormone receptor gene in familial isolated GH deficiency", Eur. J. Endocrinol., Jan. 2003, vol. 148(1): pp. 25-30.

Panayotatos, N. et al. "Localization and functional receptor epitopes on the structure of ciliary neurotrophic factor indicates a conserved, function-related epitope topography among helical cytokines", *Journal of Biological Chemistry*, vol. 270, No. 23, pp. 14007-14014, Jun. 9, 1995, The American Society for Biochemistry and Molecular Biology, Inc.

Wlodawer, A. et al., "Hematopoietic cytokines: similarities and differences in the structures, with implications for receptor binding", *Protein Science*, vol. 2, pp. 1373-1382, 1993, The Protein Society.

* cited by examiner

THROMBOPOIETIN PROTEIN VARIANTS

TECHNICAL FIELD

The present invention relates to a protein variant which substitutes valine for phenylalanine residue in a binding domain having a biological response-modifying function by binding to a receptor, ligand or substrate. More particularly, the present invention relates to a protein variant which substitutes valine for phenylalanine residue in an α-helix domain participating in the binding of a human cytokine protein to a corresponding receptor.

BACKGROUND ART

Many human diseases are caused by the loss of protein function due to defects or an insufficient amount of a protein. To treat such diseases, related proteins have been directly administered to patients. However, many physiologically active proteins used as medicines are easily degraded in serum before they arrive at target tissues and act therein. For this reason, most physiologically active proteins having therapeutic value are excessively or frequently administered to patients to maintain an appropriate concentration capable of offering satisfactory therapeutic effects.

An approach to solve the above problems is to conjugate with polyethylene glycol (PEGylation) or microencapsulate physiologically active proteins. However, these methods are cumbersome because target proteins are primarily produced in microorganisms and purified, and are then PEGlyated or microencapsulated. In addition, cross-linking may occur at undesired positions, which may negatively affect the homogeneity of final products.

Another approach involves glycosylation. Cell surface proteins and secretory proteins produced by eukaryotic cells are modified by a glycosylation process. Glycosylation is known to influence in vivo stability and function of proteins, as well as their physiological properties. However, since glycosylated proteins can be produced only by eukaryotic cells capable of performing glycosylation, their production process is complicated, and it is difficult to attain homogeneous final products which are glycosylated at all desired positions.

In addition, the conventional techniques all improve the problems associated with administration frequency, but do not increase the physiological efficacy of proteins, leading to excessive dosage. For example, NESP developed by the Amgen Company (see U.S. Pat. No. 6,586,398) improves the frequent administration by extending the half-lives of proteins in the blood, but does not increase the efficacy of proteins, leading to excessive dosage that may induce the production of blocking antibodies.

An approach used to improve the efficacy of physiologically active proteins is to mutagenize some amino acid residues of a wild-type protein to improve biological activity of the protein. Related protein variants are disclosed in the following patent publications: (1) U.S. Pat No. 5,457,089: human erytropoietin (EPO) variants where the carboxyl terminal region was altered to increase binding affinity of EPO to its receptor, (2) International Pat. Publication No. 02/077034: human granulocyte colony stimulating factor (G-CSF) variants where a T-cell epitope was altered to reduce immunogenicity of human G-CSF in humans; (3) International Pat. Publication No. 99/57147: human thrombopoietin (TPO) variants prepared by substituting glutamic acid at the 115 position with lysine, arginine or tyrosine in a TOP protein having an amino acid sequence corresponding to 7th to 151st amino acid residues of human mature TPO; and (4) U.S. Pat. Nos. 6,136,563 and 6,022,711 that disclose human growth hormone variants having alanine substitutions at the 18, 22, 25, 26, 29, 65, 168 and 174 positions.

However, the aforementioned protein variants are altered forms made for improving only therapeutic efficacy regardless of changes in in vivo antigenicity. Thus, the scale, degree and position of these alterations have high potential to induce immune responses in humans. Antigenicity in humans may cause serious adverse effects (Casadevall et al. N. Eng. J. Med. 2002, vol. 346, p. 469).

DISCLOSURE OF THE INVENTION

It is therefore an object of the present invention to provide biological response-modifying protein variants having improved pharmacological action, which are capable of maximizing biological response modifying effects upon administration and preventing the formation of blocking antibodies through an improvement in efficacy of conventional biological response-modifying proteins, and methods of preparing such variants.

In one aspect, the present invention provides a protein variant which substitutes valine for phenylalanine residue in a binding domain of a protein having a biological response-modifying function by binding to a receptor, ligand or substrate.

In another aspect, the present invention provides a DNA encoding a protein variant which substitutes valine for phenylalanine residue in a binding domain of a protein having a biological response-modifying function by binding to a receptor, ligand or substrate.

In a further aspect, the present invention provides a recombinant expression vector to which a DNA encoding a protein variant which substitutes valine for phenylalanine residue in a binding domain of a protein having a biological response-modifying function by binding to a receptor, ligand or substrate is operably linked.

In yet another aspect, the present invention provides a host cell transformed or transfected with a recombinant expression vector to which a DNA encoding a protein variant which substitutes valine for phenylalanine residue in a binding domain of a protein having a biological response-modifying function by binding to a receptor, ligand or substrate is operably linked.

In still another aspect, the present invention provides a method of preparing a protein variant, comprising cultivating a host cell transformed or transfected with a recombinant expression vector to which a DNA encoding a protein variant which substitutes valine for phenylalanine residue in a binding domain of a protein having a biological response-modifying function by binding to a receptor, ligand or substrate is operably linked, and isolating the protein variant from a resulting culture.

In still another aspect, the present invention provides a pharmaceutical composition comprising a protein variant which substitutes valine for phenylalanine residue in a binding domain of a protein having a biological response-modifying function by binding to a receptor, ligand or substrate, and a pharmaceutically acceptable carrier.

BRIEF DESCRIPTION OF THE DRAWINGS

The above and other objects, features and other advantages of the present invention will be more clearly understood from the following detailed description taken in conjunction with the accompanying drawings, in which:

FIG. 1A is a multiple alignment of amino acid sequences of domains participating in the binding of 4-helix bundle cytokines to corresponding receptors;

FIG. 1B is a multiple alignment of amino acid sequences of domains participating in the binding of interferons to corresponding receptors;

FIG. 2A shows the results of Western blotting of TPO variants according to the present invention, (from the leftmost lane: marker, wild-type TPO; TPO-[F46V]; TPO-[F128V]; TPO-[F131V]; and TPO-[F141V]);

FIG. 2B shows the results of Western blotting of EPO variants according to the present invention, (from the leftmost lane: marker, wild-type EPO; EPO-[F48V]; EPO-[F138V]; EPO-[F142V]; and EPO-[F148V]);

FIG. 2C shows the results of Western blotting of G-CSF variants according to the present invention, (from the leftmost lane: marker, wild-type G-CSF; G-CSF-[F13V]; G-CSF-[F83V]; G-CSF-[F113V]; G-CSF-[F140V]; G-CSF-[F144V]; and G-CSF-[F160V]);

Figure 9A:
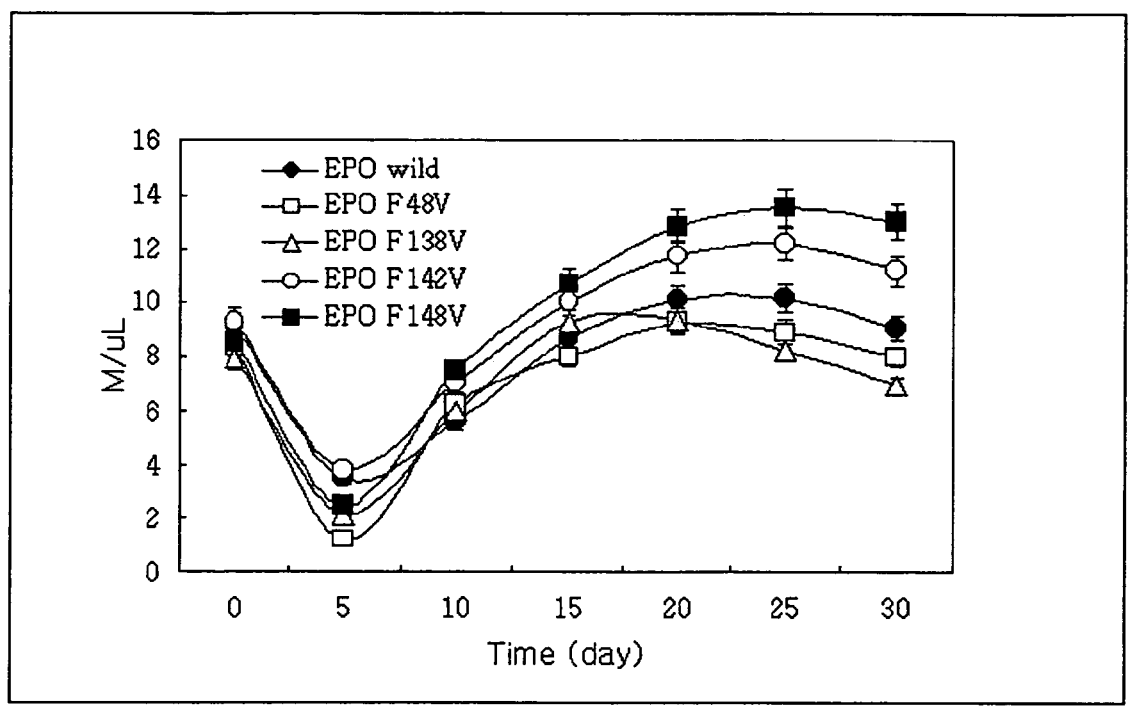
Figure 9B:
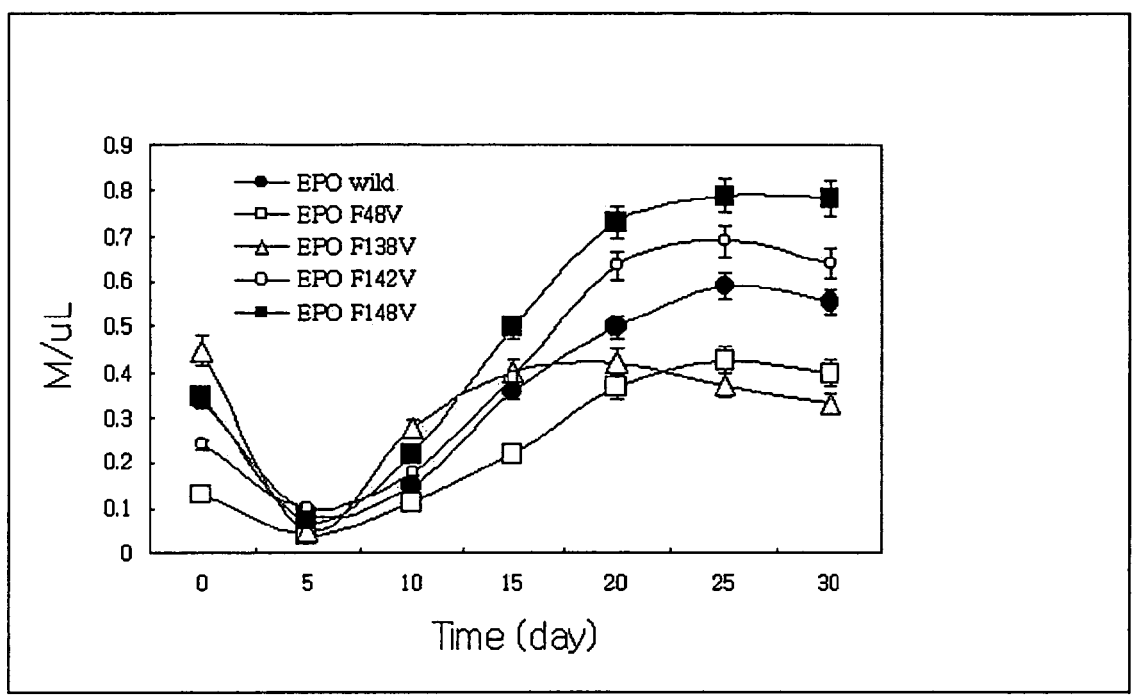
Figure 9C:
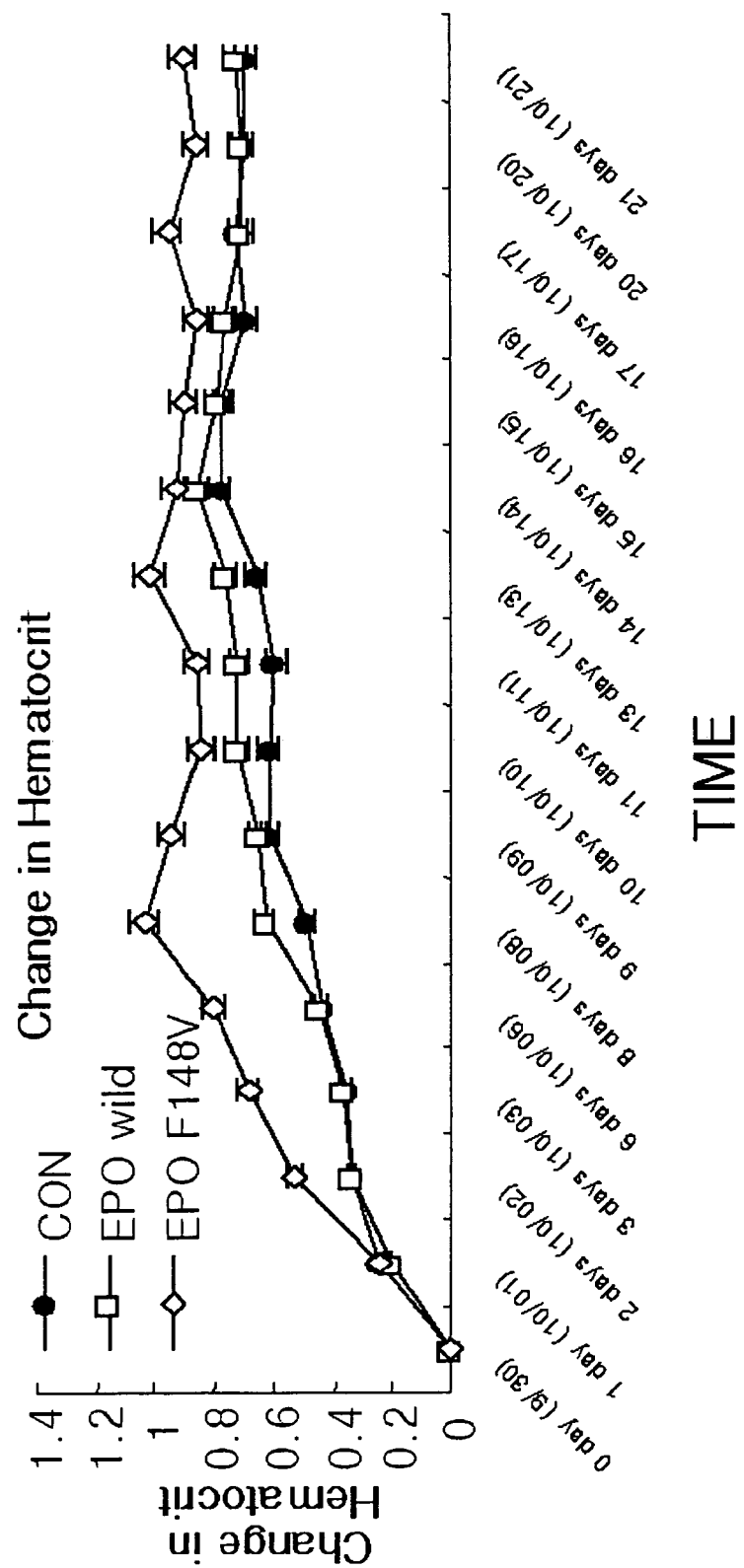
Figure 10A:
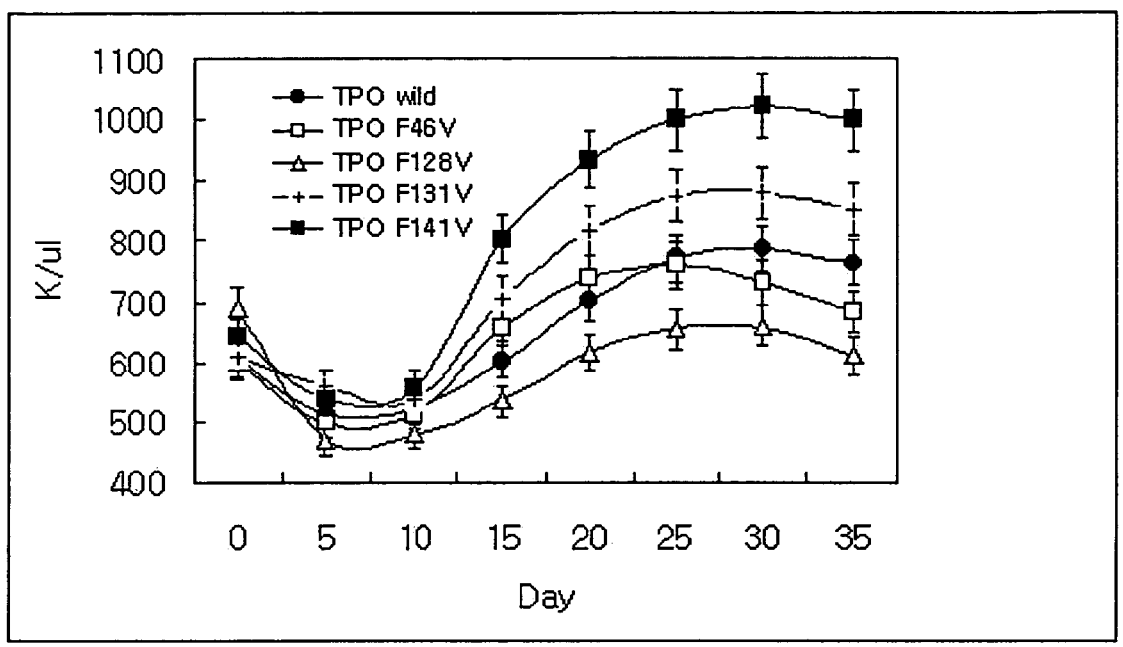
Figure 10B:
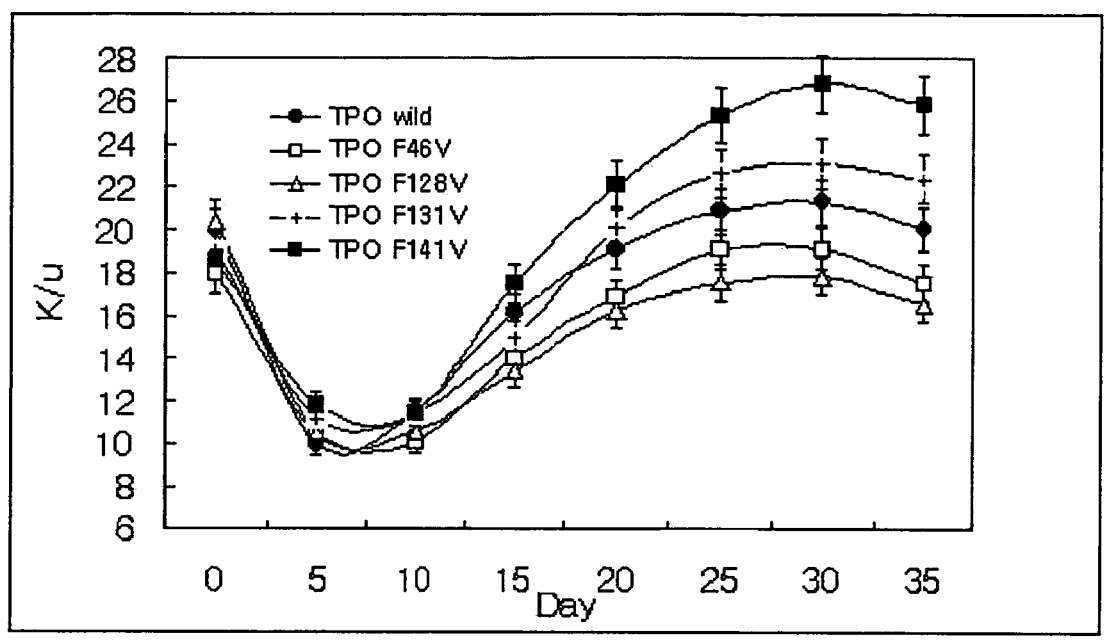
Figure 10C:
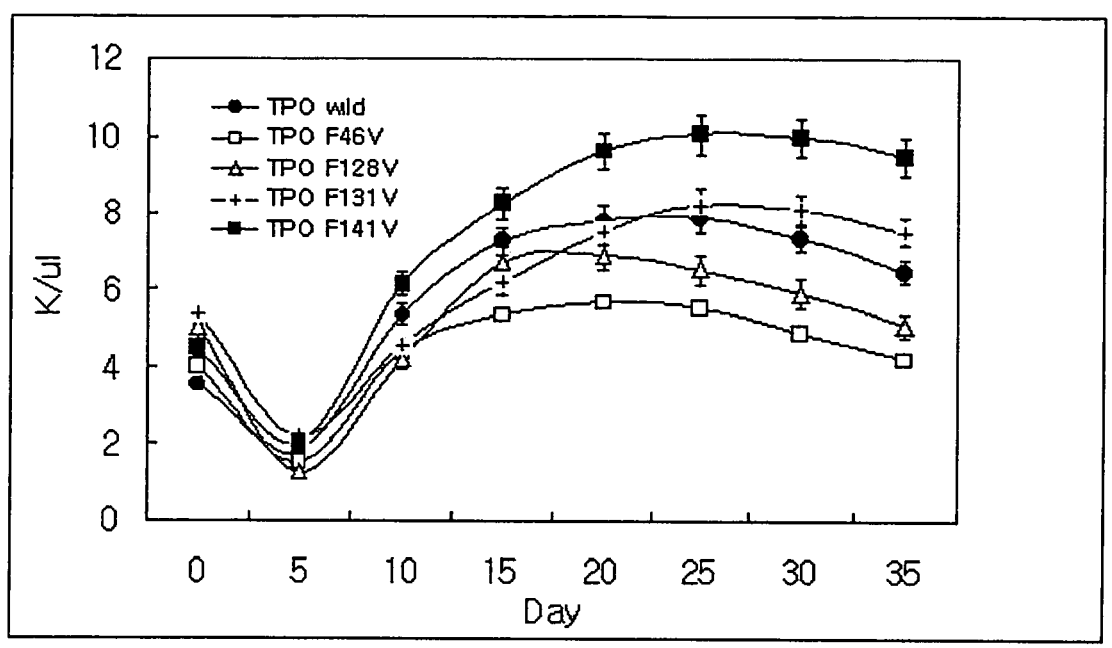

FIGS. 9A, 9B and 9C are graphs showing the proliferation rates of erytrocytes, proliferation rates of reticulocytes, and changes in hematocrit, respectively, as results of tests to evaluate in vivo activity of EPO variants according to the present invention, in nice intraperitoneally injected with the EPO variants; and FIGS. 10A, 10B and 10C are graphs showing proliferation rates of platelets, leukocytes and neutrophils, respectively, as results of tests to evaluate the in vivo activity of TPO variants according to the present invention, in rats intraperitoneally injected with the TPO variants.

BEST MODE FOR CARRYING OUT THE INVENTION

Single capital letters standing for amino acids, as used herein, represent the following amino acids according to the standard abbreviations defined by the International Union of Biochemistry:

A: Alanine; B: Asparagine or Aspartic acid;
C: Cysteine; D: Aspartic acid; E: Glutamic acid,
F: Phenylalanine; G: Glycine; H: Histidine;
I: Isoleucine; K: Lysine; L: Leucine;
M: Methionine; N: Asparagine; P: Proline;
Q: Glutamine; R: Arginine; S: Serine;
T: Threonine; V: Valine; W: Tryptophan;
Y: Tyrosine; and Z: Glutamine or Glutamic acid The designation "(one capital for an amino acid)(amino acid position)(one capital for another amino acid)", as used herein, means that the former amino acid is substituted by the latter amino acid at the designated amino acid position of a certain protein. For example, F48V indicates that the phenylalanine residue at the 48th position of a certain protein is substituted by valine. The amino acid position is numbered from the N terminus of a mature wild-type protein The term "protein variant", as used herein, refers to a protein that has an amino acid sequence different from a wild-type form by a substitution of valine for phenylalanine residue in a protein having physiological function by binding to a receptor, ligand or substrate, in particular, in a domain participating in the binding to a receptor, ligand or substrate. In the present invention, a protein variant is designated for convenience as "protein name-[(one capital for an amino acid)(amino acid position)(one capital for another amino acid)]". For example, TPO-[F131V] indicates a TPO variant in which the phenylalanine residue at position 131 of wild-type TPO is substituted by valine.

The term "biological response-modifying proteins", as used herein, refers to proteins involved in maintaining homeostasis in the body by inducing the initiation or stop of various biological responses occurring in the multicellular body and regulating the responses to be organically connected to each other. These proteins typically act by binding to receptors, ligands or substrates.

Proteins capable of being altered according to the present invention include all proteins that have innate function to modulate biological responses by binding receptors, ligands or substrates. Non-limiting examples of the proteins include cytokines, cytokine receptors, adhesion molecules, tumor necrosis factor (TNF) receptors, enzymes, receptor tyrosine kinases, chemokine receptors, other cell surface proteins, and soluble ligands. Non-limiting examples of the cytokines include CNTF (cytoneurotrophic factor), GH (growth hormone), IL-1, IL-1Ra (interleukin-1 receptor antagonist), placental lactogen (PL), cardioliphin, IL-2, IL-3, IL-4, IL-5, IL-6, IL-7, IL-10, IL-12, IL-17, TNF, TGF (transforming growth factor), IFN (interferon), GM-CSF (granulocyte-monocyte colony stimulating factor), G-CSF (granulocyte colony stimulating factor), EPO (erytropoietin), TPO (thrombopoietin), M-CSF (monocyte colony stimulating factor), LIF (leukemia inhibitory factor), OSM (oncostatin-M), SCF (stem cell factor), HGF (hepatocyte growth factor), FGF (fibroblast growth factor), IGF (insulin-like growth factor), and LPT (Leptin). Non-limiting examples of the cytokine receptors include growth hormone receptor (GHR), IL-13R, IL-1R, IL-2R, IL-3R, IL-4R, IL-5R, IL-6R, IL-7R, IL-9R, IL-15R, TNFR, TGFR, IFNR (e.g., IFN-γR α-chain, IFN-γR β-chain), interferon-αR, -βR and -γR, GM-CSFR, GCSFR, EPOR, cMp1, gp130, and Fas (Apo 1). Examples of the chemokine receptors include CCR1 and CXCR1-4. Examples of the receptor tyrosine kinases include TrkA, TrkB, TrkC, Hrk, REK7, Rse/Tyro-3, hepatocyte growth factor R, platelet-derived growth factor R, and Flt-1. Examples of other cell surface proteins include CD2, CD4, CD5, CD6, CD22, CD27, CD28, CD30, CD31, CD40, CD44, CD100, CD137, CD150, LAG-3, B7, B61, β-neurexin, CTLA-4, ICOS, ICAM-1, complement R-2(CD21), IgER, lysosomal membrane gp-1, α2-microglobulin receptor-related protein, and natriuretic peptide receptor.

To improve the efficacy of modulating biological responses for the aforementioned numerous proteins having biological response-modulating function, the present invention intends to provide protein variants capable of binding to receptors, ligands or substrates having a higher hydrophobic force than that of wild types. For this purpose, the present invention is characterized by substituting valine for phenylalanine residue in a binding domain of each of the proteins.

Phenylalanine is a relatively non-polar amino acid that has an aromatic side chain and a known hydrophobicity index of 3.0. Valine is a non-polar hydrophobic amino acid that has an aliphatic side chain and a known hydrophobicity index of 4.0. In addition, since valine is smaller than phenylalanine, a protein substituting valine for phenylalanine residue becomes more deeply depressed in a pocket binding to a corresponding receptor, ligand or substrate. Thus, a protein substituting valine for phenylalanine residue in a binding domain has increased hydrophobic force and a more deeply depressed space so that it has increased binding affinity to a receptor, ligand or substrate, leading to a desired increase in biological response-modulating efficiency.

In addition, the valine substitution for phenylalanine residue, as a conservative substitution, has a minimal influence on the secondary or tertiary structure of a protein, and thus rarely affects the function of the protein (Argos, EMBO J. 1989, vol. 8, pp 779-85). Further, because phenylalanine is mainly present in a highly hydrophobic region, it is rarely exposed to the exterior. When such phenylalanine residue is substituted by valine, a protein becomes more deeply depressed from the surface due to the higher hydrophobicity of valine. Thus, this substitution has a lower potential to induce antibody production. A certain protein should primarily bind a corresponding receptor, ligand or substrate to modulate a specific biological response. In the case that the stronger this binding is, the efficacy of modulating a biological response is improved, related proteins all may be altered according to the present invention, and the present invention includes all of the resulting protein variants.

The fact that such a substitution of valine for phenylalanine residue leads to increased binding affinity is supported by the finding of a mutation of FcγRIIIa(CD16) expressed on NK cells in human autoimmune diseases. The human receptor protein has a genetic polymorphism. That is, individuals are divided into two groups: at position 176 in a region participating in recognizing Fc of an antibody ligand, one group has phenylalanine, and the other group has valine. Individuals having phenylalanine at position 176 of the receptor have weakened binding affinity to the Fc region of the antibody ligand and are highly susceptible to systemic lupus erythematosus (SLE) (Jianming Wu et al. J. CIin. Invest. 1997, vol. 100, pp. 1059-70).

On the other hand, as noted above, the present invention is characterized by substituting valine for phenylalanine residue in a binding domain of a biological response-modulating protein. The term "binding domain", as used herein, refers to a portion (that is, domain) of a protein performing its biological function by binding to a receptor, ligand or substrate, and has relatively high hydrophobicity and low antigenicity compared to other regions of the protein. Binding domains of proteins are well known in the art. For example, some 4-α helix bundle cytokines and interferons, which are used in an embodiment of the present invention, are known to have a D-α helix structure and an A-α helix structure, respectively, that serve as binding domains for corresponding receptors.

However, a binding domain altered according to the present invention is not limited to binding domains known in the art. This is because the binding of a biological response-modulating protein to a receptor, ligand or substrate is influenced by, in addition to amino acid residues involved in direct binding, other several amino acid residues. A "binding domain" of a biological response-modulating protein, altered according to the present invention, further includes about 50 amino acid residues, preferably about 25 amino acid residues, and more preferably about 10 amino acid residues, from both ends of a binding domain known in the art.

Figure 1A:
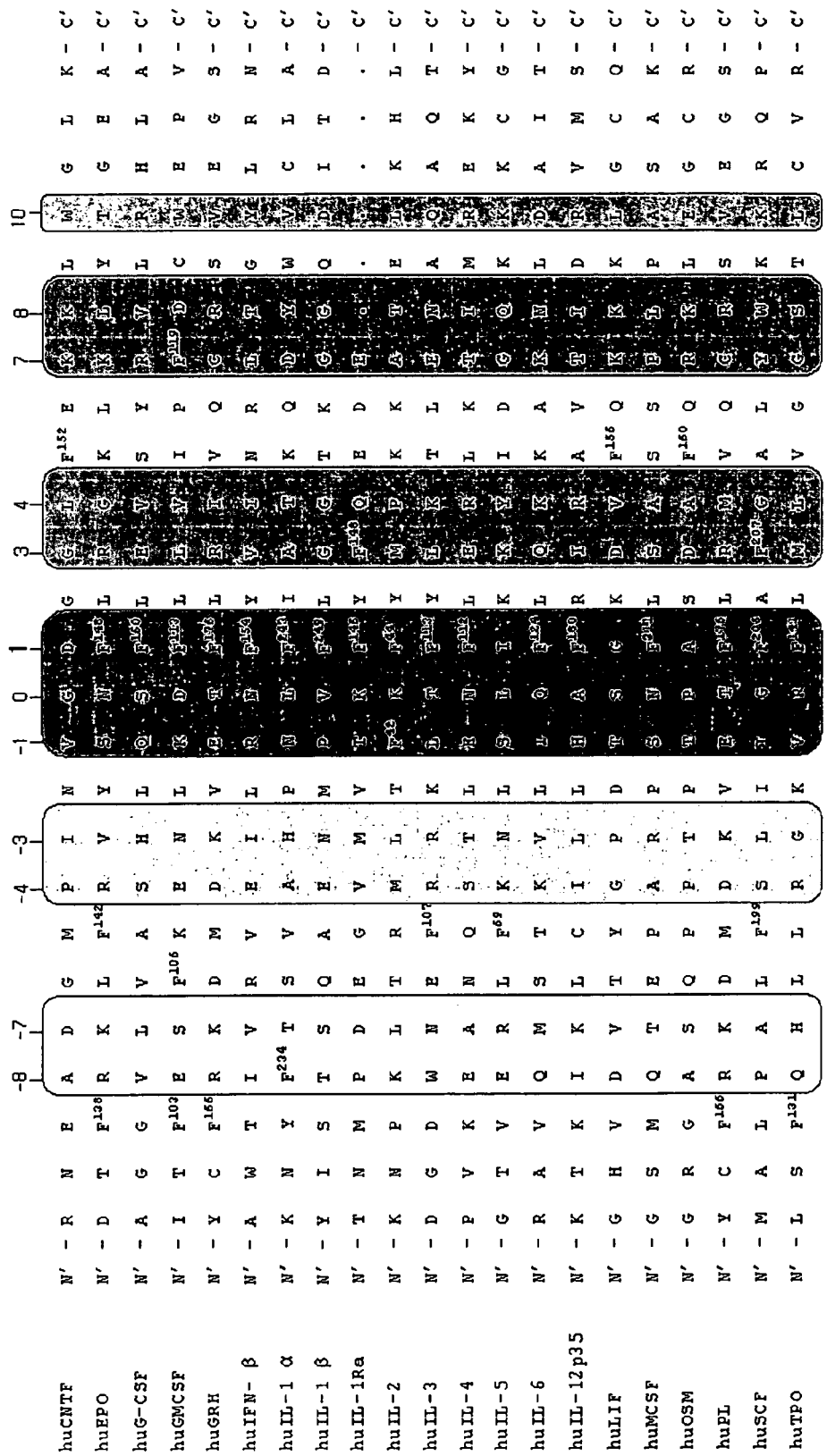
Figure 1B:
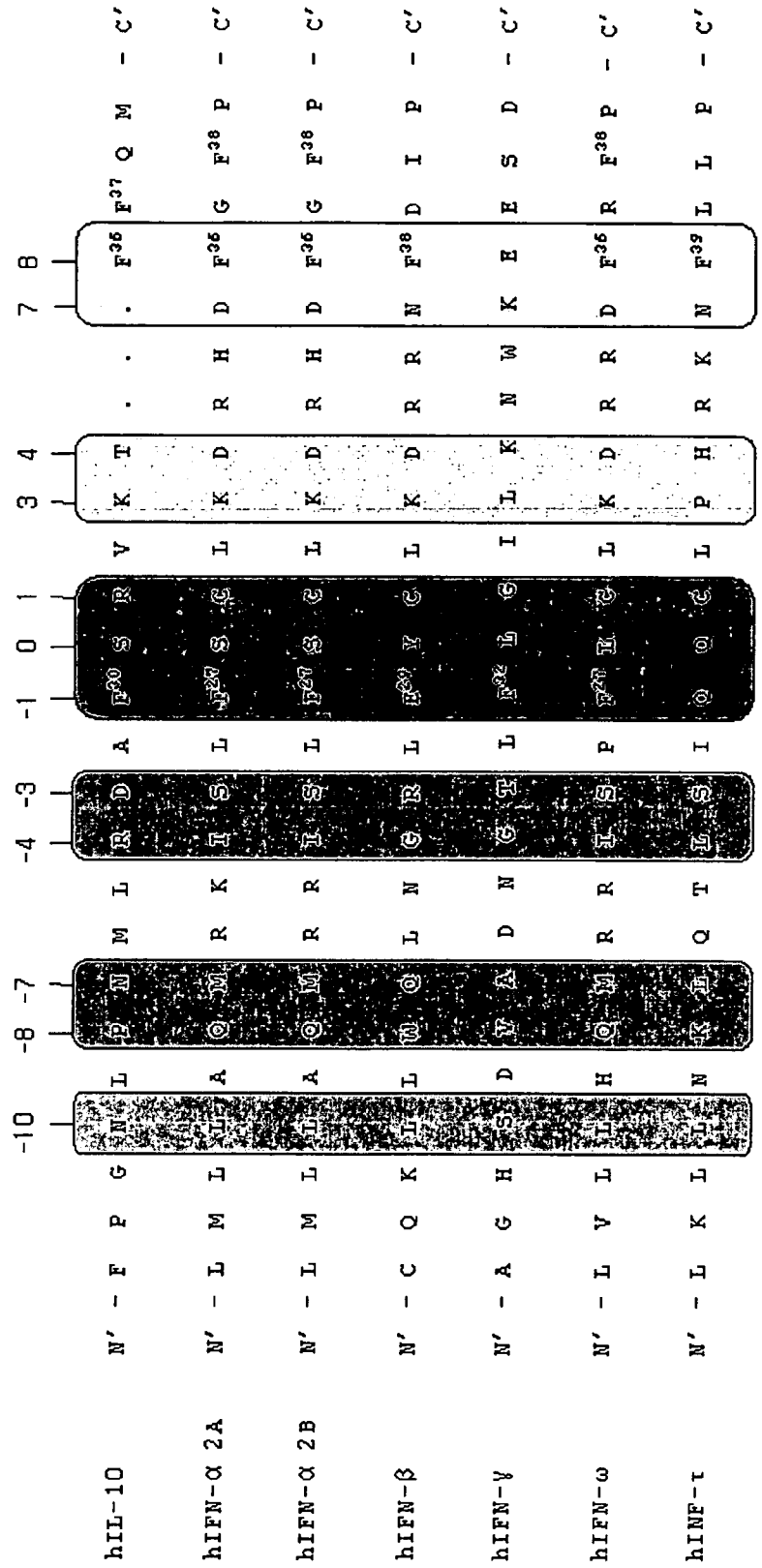

One aspect of the present invention involves cytokines that typically contain several a helix structures. Among them, the first and last helices from the N-termius are known as binding domains participating in binding of cytokines to corresponding cytokine receptors (see FIG. 1). α helices responsible for binding of cytokines to corresponding receptors differ according to the type of cytokines, and are well known in the art. For example, in IL-2, the second and fifth helices bind to the p55α receptor among IL-2 receptors, the first helix binds to the p75γ receptor among IL2 receptors, and the sixth helix binds to gamma receptor (Fernando Bazan, Science J. 1992, vol. 257, pp. 410-2). As described above, cytokines each have particular helices participating in binding, but the helices have highly conserved amino acid sequences. The present invention provides a cytokine variant that is capable of binding to a cytokine receptor with higher affinity than a wild-type cytokine by substituting valine for phenylalanine residue in an alpha helix corresponding to a binding domain of a cytokine.

One aspect related to the cytokines involves the 4-helix bundle family of cytokines. Such cytokines include CNTF, EPO, Flt3L, GM-CSF, IL-2, IL-3, IL-4, IL-5, IL-6, IL-12p35, LPT, LIF, M-CSF, OSM, PL, SCF, TPO G-CSF, GHR and IFN. These cytokines all have four alpha helices, which are designated as A-alpha helix, B-alpha helix, C-alpha helix and D-alpha helix, respectively. The D- and A-alpha helices mainly participate in binding to receptors (Fernando Bazan, Immunology today, 1990, vol. 11 pp. 350-4, The Cytokine Facts Book, 1994, pp. 104-247).

Among the aforementioned 4-helix bundle cytokines, CNTF, EPO, Flt3L, GM-CSF, IL-2, IL-3, IL-4, IL-5, IL-6, IL-12p35, LPT, LIF, M-CSF, OSM, PL, SCF, TPO, G-CSF and GHR have binding domains which each include a D-alpha helix and a region linking a C-alpha helix and the D-alpha helix. More particularly, the binding domains include amino acid residues between positions 110 and 180 among amino acid residues of the 4-helix bundle cytokines. Therefore, in an aspect, the present invention provides a 4-helix bundle cytokine variant that is capable of binding to a corresponding receptor with higher affinity than a wild type by substituting valine for phenylalanine among amino acid residues between positions 110 and 180 of a 4-helix bundle cytokine.

Of the aforementioned 4-helix bundle cytokines, interferons (e.g., IFN-α2A, IFN-α2B, IFN-β, IFN-γ, IFN-ω, IFN-τ) have a binding domain that contains an "A-alpha helix". More particularly, the binding domain of interferons includes amino acid residues between positions 1 and 50. Therefore, in another aspect, the present invention provides an interferon variant that is capable of binding to an interferon receptor having higher affinity than a wild type by substituting valine for phenylalanine among amino acid residues between positions 1 and 50 of an interferon.

On the other hand, the binding domain altered according to the present invention may include two or more phenylalanine residues. The two or more phenylalanine residues may all be substituted by valine. However, because this case leads to a great reduction in protein expression levels, preferably only one phenylalanine residue is substituted by valine. In this regard, the present inventors found that, when phenylalanine residue present in a highly hydrophobic region is substituted by valine, the biological response-modulating protein has much improved efficacy. Therefore, in the present invention, the phenylalanine residue to be substituted by valine is preferably selected in a highly hydrophobic region present in the binding domain specified according to the present invention. Hydrophobicity for a specific region of an amino acid sequence comprising a protein may be determined by a method known in the art (Kyte, J. et al. J. Mol. Biol. 1982, vol. 157, pp. 105-132, Hopp, T. P. et al. Proc. Nat. Acad. Sci. USA, 1981, vol. 78(6), pp. 3824-3828).

The variant of a biological response-modulating protein according to the present invention may be prepared by chemical synthetic methods generally known in the art (Creighton, Proteins: Structures and Molecular Principles, W.H. Freeman and Co., NY 1983). Representative methods, but are not limited to, include liquid or solid phase synthesis, fragment condensation, and F-MOC or T-BOC chemical synthesis (Chemical Approaches to the Synthesis of Peptides and Proteins, Williams et al., Eds., CRC Press, Boca Raton Fla., 1997; A Practical Approach, Atherton & Sheppard, Eds., IRL Press, Oxford, England, 1989).

Alternatively, the protein variant according to the present invention may be prepared by recombinant DNA techniques. These techniques include a process of preparing a DNA sequence encoding the protein variant according to the present invention. Such a DNA sequence may be prepared by altering a DNA sequence encoding a wild-type protein. In brief after a DNA sequence encoding a wild-type protein is synthesized, a codon for phenylalanine is changed to another codon for valine by sitelirected mutagenesis, thus generating a desired DNA sequence.

Also, the preparation of a DNA sequence encoding the protein variant according to the present invention may be achieved by a chemical method. For example, a DNA sequence encoding the protein variant may be synthesized by a chemical method using an oligonucleotide synthesizer. An oligonucleotide is made based on an amino acid sequence of a desired protein variant, and preferably by selecting a appropriate codon used by a host cell producing a protein variant. The degeneracy in the genetic code, which means that one amino acid is specified by more than one codon, is well known in the art. Thus, there is a plurality of DNA sequences with degeneracy encoding a specific protein variant, and they all fall into the scope of the present inventions A DNA sequence encoding the protein variant according to the present invention may or may not include a DNA sequence encoding a signal sequence. The signal sequence, if present, should be recognized by a host cell selected for the expression of the protein variant. The signal sequence may have a prokaryotic or eukaryotic origin or a combinational origin, and may be a signal sequence of a native protein. The employment of a signal sequence may be determined according to the effect of expression of a protein variant as a secretory form in a recombinant cell producing the protein variant. If a selected cell is a prokaryotic cell, a DNA sequence typically does not encode a signal sequence but instead contains preferably an N-terminal methionine for direct expression of a desired protein, and most preferably, a signal sequence derived from a wild type protein is used Such a DNA sequence as prepared above is operably linked to another DNA sequence encoding the protein variant of the present invention, and is inserted into a vector including one or more expression control sequences regulating the expression of the resulting DNA sequence. Then, a host is transformed or transfected with the resulting recombinant expression vector. The resulting transformant or transfectant is cultured in a suitable medium under suitable conditions for the expression of the DNA sequence. A substantially pure variant of a biological response-modulating protein coded by the DNA sequence is recovered from the resulting culture.

The term "vector", as used herein, means a DNA molecule serving as a vehicle capable of stably carrying exogeneous genes into host cells. For useful application, a vector should be replicable, have a system for introducing itself into a host cell, and possess selectable markers. In addition, the term "recombinant expression vector", as used herein, refers to a circular DNA molecule carrying exogeneous genes operably linked thereto to be expressed in a host cell. When introduced into a host cell, the recombinant expression plasmid has the ability to replicate regardless of host chromosomal DNA at a high copy number and to produce heterogeneous DNA. As generally known in the art, in order to increase the expression level of a transfected gene in a host cell, the gene should be operably linked to transcription and translation regulatory sequences functional in a host cell selected as an expression system. Preferably, the expression regulation sequences and the exogeneous genes may be carried in a single expression vector containing bacteria-selectable markers and a replication origin. In the case that eukaryotic cells are used as an expression system, the expression vector should further comprise expression markers useful in the eukaryotic host cells.

The term "expression control sequences", as used herein in connection with a recombinant expression vector, refers to nucleotide sequences necessary or advantageous for expression of the protein variant according to the present invention. Each control sequence may be native or foreign to the nucleotide sequence encoding the protein variant Non-limiting examples of the expression control sequences include leader sequences, polyadenylation sequences, propeptide sequences, promoters, enhancers or upstream activating sequences, signal peptide sequences, and transcription terminators. The expression control sequence contains at least one promoter sequence.

The term "operably linked" refers to a state in which a nucleotide sequence is arranged with another nucleotide sequence in a functional relationship. The nucleotide sequences maybe a gene and control sequences, which are linked in such a manner that gene expression is induced when a suitable molecule (for example, transcription-activating protein) binds to the control sequence(s). For example, when a pre-sequence or secretory leader facilitates secretion of a mature protein, it is referred to as "operably linked to the protein". A promoter is operably linked with a coding sequence when it regulates transcription of the coding sequence. A ribosome-binding site is operably linked to a coding sequence when it is present at a position allowing translation of the coding sequence. Typically, the term "operably linked" means that linked nucleotide sequences are in contact with each other. In the case of a secretory leader sequence, the term means that it contacts a coding sequence and is present within a leading frame of the coding sequence. However, an enhancer need not necessarily contact a coding sequence. Linkage of the nucleotide sequences may be achieved by ligation at convenient restriction enzyme recognition sites. In the absence of restriction enzyme recognition sites, oligonucleotide adaptors or linkers may be used, which are synthesized by the conventional methods.

In order to express a DNA sequence encoding the protein variant according to the present invention, a wide variety of combinations of host cells and vectors as an expression system may be used. Expression vectors useful for transforming eukaryotic host cells contain expression regulation sequences from, for example, SV40, bovine papillomavirus, adenovirus, adeno-associated viruses, cytomegalovirus and retroviruses. Expression vectors useful in bacterial host cells include bacterial plasmids from $E.$ $coli$, which are exemplified by pET, pRSET, pBluescript, pGEX2T, pUC, pBR322, pMB9 and derivatives thereof, plasmids having a broad range of host cells, such as RP4, phage DNAs, exemplified by a wide variety of λ phage derivatives including λ gt10, λ gt11 and NM989, and other DNA phages, exemplified by filamentous single-stranded DNA phages such as M13. Expression vectors useful in yeast cells include 2µ plasmid and derivatives thereof Expression vectors useful in insect cells include pVL 941.

To express a DNA sequence encoding the protein variant according to the present invention, any of a wide variety of expression control sequences may be used by these vectors. Such useful expression control sequences include those associated with structural genes of the aforementioned expression vectors. Examples of useful expression control sequences include the early and later promoters of SV40 or adenoviruses, the lac system, the trp system, the TAC or TRC system, T3 and T7 promoters, the major operator and promoter regions of phage λ, the control regions for fd coat protein, the promoter for 3-phosphoglycerate kinase or other glycolytic enzymes, the promoters of phosphatases, for example, Pho5, the promoters of the yeast alpha-mating system and other sequences known to control the expression of genes of prokaryotic or eukaryotic cells or their viruses, and various combinations thereof In particular, T7 RNA polymerase promoter Φ 10 is useful for expressing a polypeptide in $E.$ $coli$.

Host cells transformed or transfected with the aforementioned recombinant expression vector comprise another aspect of the present invention. A wide range of mononuclear host cells may be used for expressing a DNA sequence encoding the protein variant of the present invention. Examples of the host cells include prokaryotic and eukaryotic cells such as $E.$ $coli,$ $Pseudomonas$ sp., $Bacillus$ sp., $Streptomyces$ sp., fungi or yeasts, insect cells such as $Spodoptera$ $frugiperda$ (Sf9), animal cells such as Chinese hamster ovary cells (CHO) or mouse cells, African green monkey cells such as COS 1, COS 7, BSC 1, BSC 40 or BMT 10, and tissue-cultured human and plant cells. Preferred hosts include bacteria such as $E.$ $coli$ and $Bacillus$ $subtilis$, and tissue-cultured mammalian cells.

The transformation and transfection may be performed by the methods described in basic experimental guidebooks (Davis et al., Basic Methods in Molecular Biology, 1986; Sambrook, J., et al., Basic Methods in Molecular Biology, 1989). The preferred methods for introducing a DNA sequence encoding the protein variant according to the present invention into a host cell include, for example, calcium phosphate transfection, DEAE-Dextra mediated transfection, transfection, microinjection, cationic lipid-mediated transfection, electroporation, transduction, scrape loading, ballistic introduction, and infection Also, it will be understood that all vectors and expression control sequences do not function equally in expressing the DNA sequence of the present invention. Likewise, all hosts do not function equally for an identical expression system. However, those skilled in the art are able to make a suitable selection from various vectors, expression control sequences and hosts, within the scope of the present invention, without a heavy experimental burden. For example, a vector may be selected taking a host cell into consideration because the vector should be replicated in the host cell. The copy number of a vector, ability to control the copy number, and expression of other proteins encoded by the vector, for example, an antibiotic marker, should be deliberated. Also, an expression control sequence may be selected taking several factors into consideration. For example, relative strength, control capacity and compatibility with the DNA sequence of the present invention of the sequence, particularly with respect to possible secondary structures, should be deliberated Further, the selection of a host cell may be made under consideration of compatibility with a selected vector, toxicity of a product encoded by a nucleotide sequence, secretory nature of the product, ability to correctly fold a polypeptide, fermentation or cultivation requirements, ability to ensure easy purification of a product encoded by a nucleotide sequence, or the like.

In the method of preparing the protein variant according to the present invention, the host cells are cultivated in a nutrient medium suitable for production of a polypeptide using methods known in the art. For example, the cells may be cultivated by shake flask cultivation, small-scale or large-scale fermentation in laboratory or industrial fermenters performed in a suitable medium and under conditions allowing the polypeptide to be expressed and/or isolated. The cultivation takes place in a suitable nutrient medium containing carbon and nitrogen sources and inorganic salts, using procedures known in the art Suitable media are commercially available from commercial suppliers and may be prepared according to published compositions (for example, the catalog of American Type Culture Collection). If the polypeptide is secreted into the nutrient medium, the polypeptide can be recovered directly from the medium. If the polypeptide is not secreted, it can be recovered from cell lysates.

The biological response-modulating protein variant according to the present invention may be recovered by methods known in the art For example, the protein variant may be recovered from the nutrient medium by conventional procedures including, but not limited to, centrifugation, filtration, extraction, spray drying, evaporation, or precipitation. Further, the protein variant may be purified by a variety of procedures known in the art including, but not limited to, chromatography (e.g., ion exchange, affinity, hydrophobicity, and size exclusion), electrophoresis, differential solubility (e.g., ammonium sulfate precipitation), SDS-PAGE, or extraction.

The present invention provides a pharmaceutical composition comprising a variant of a biological response-modulating protein and a pharmaceutically acceptable carrier. In the pharmaceutical composition according to the present invention, the biological response-modulating protein variant is preferably contained in a therapeutically effective amount.

The carrier used in the pharmaceutical composition of the present invention includes the commonly used carriers, adjuvants and vehicles, in the pharmaceutical field, which are as a whole called "pharmaceutically acceptable carriers". Non-limiting pharmaceutically acceptable carriers useful in the pharmaceutical composition of the present invention include ion exchange, alumina, aluminum stearate, lecithin, serum proteins (e.g., human serum albumin), buffering agents (e.g., sodium phosphate, glycine, sorbic acid, potassium sorbate, partial glyceride mixtures of vegetable satuaed fatty acids), water, salts or electrolytes (e.g., protamine sulfate, disodium hydrophosphate, potassium hydrophoshate, sodium chloride, and zinc salts), colloidal silica, magnesium trisilicate, polyvinylpyrrolidone, cellulose-based substrates, polyethylene glycol, sodium carboxymethylcellulose, polyarylate, waxes, polyethylene-polyoxypropylene-block copolymers, polyethylene glycol, and wool fat.

The pharmaceutical composition of the present invention may be administered via any of the common routes, if it is able to reach a desired tissue. Therefore, the pharmaceutical composition of the present invention may be administered topically, orally, parenterally, intraocularly, transdermally, intrarectally and intraluminally, and may be formulated into solutions, suspensions, tablets, pills, capsules and sustained release preparations. The term "parenteral", as used herein includes subcutaneous, intranasal, intravenous, intraperitoneal, intramuscular, intra-articular, intra-synovial, intrasternal, intracardial intrathecal, intralesional and intracranial injection or infusion techniques.

In an aspect, the pharmaceutical composition of the present invention may be formulate as aqueous solutions for parenteral administration. Preferably, a suitable buffer solution, such as Hank's solution, Ringer's solution or physiologically buffered saline, may be employed. Aqueous injection suspensions may be supplemented with substances capable of increasing viscosity of the suspensions, which are exemplified by sodium carboxymethylcellulose, sorbitol and dextran. In addition, suspensions of the active components, such as oily injection suspension, include lipophilic solvents or carriers, which are exemplified by fatty oils such as sesame oil, and synthetic fatty acid esters such as ethyl oleate, triglycerides or liposomes. Polycationic non-lipid amino polymers may also be used as vehicles. Optionally, the suspensions may contain suitable stabilizers or drugs to increase the solubility of protein variants and obtain high concentrations of the protein variants.

The pharmaceutical composition of the present invention is preferably in the form of a sterile injectable preparation, such as a sterile injectable aqueous or oleaginous suspension. Such suspension may be formulated according to the methods known in the art, using suitable dispersing or wetting agents (e.g., Tween 80) and suspending agents. The sterile injectable preparations may also be a sterile injectable solution or suspension in a non-toxic parenterally-acceptable diluent or solvent, such as a solution in 1,3-butanediol. The acceptable vehicles and solvents include mannitol, water, Ringer's solution and isotonic sodium chloride solution. In addition, sterile fixed oils may conventionally be employed as a solvent or suspending medium. For this purpose, any bland fixed oil may be employed, including synthetic mono- or di-glycerides. In addition, fatty acids, such as oleic acid and glyceride derivatives thereof, may be used in the preparation of injectable preparations, like the pharmaceutically acceptable natural oils (e.g., olive oil or castor oil), and particularly, polyoxyethylated derivatives thereof.

The aforementioned aqueous composition is sterilized mainly by filtration using a filter to remove bacteria, mixing with disinfectants or in combination with radiation. The sterilized composition can be hardened, for example, by freeze-drying to obtain a hardened product, and for practical use, the hardened product is dissolved in sterilize water or a sterilized diluted solution.

The term "therapeutically effective amount", as used herein in connection with the pharmaceutical composition of the present invention, means an amount in which an active component shows an improved or therapeutic effect toward a disease to which the pharmaceutical composition of the present invention is applied. The therapeutically effective amount of the pharmaceutical composition of the present invention may vary according to the patient's age and sex, application sites, administration frequency, administration duration, formulation types and adjuvant types. Typically, the pharmaceutical composition of the present invention is admit in smaller amounts than a wild-type protein, for example, 0.01-1000 μg/kg/day, more preferably 0.1-500 μg/kg/day, and most preferably 1-100 μg/kg/day.

On the other hand, it will be apparent to those skilled in the art that diseases to which the present composition is applied may vary according to the protein type. The EPO and TPO altered as in an embodiment of the present invention may be used for treating, in addition to anemia itself, anemia as a complication associated with other diseases (e.g., anemia in inflammatory bowel disease, Progressive Kidney Disease, anemia of renal failure, the anemia associated with HIV infection in zidovudine (AZT) treated patients, anemia associated with cancer chemotherapy, Huntington's disease (HD), sickle cell anemia, Late Hyporegenerative Anemia in Neonates with Rh Hemolytic Disease after in utero Exchange Transfusion). In addition, the G-CSF altered according to the present invention may be used for treating neutropenia itself and neutropenia developed after bone marrow transplantation or cancer chemotherapy, the GH variants may be used for treating pituitary dwarfism and paediatric chronic renal failure. However, the present invention is not limited to these applications.

Hereinafter, the present invention provides interferon variants which each substitute valine for specific phenylalanine residue of 4-helix bundle cytokines, in detail, CNTF, EPO, Flt3L, G-CSF, GM-CSF, GH, IL-2, IL-3, IL-4, IL-5, IL-6, IL-12p35, LPT, LIF, M-CSF, OSM, PL, SCF, TPO, IFN-α2A, IFN-α2B, IFN-β, IFN-γ, IFN-ω and IFN-τ.

In one specific aspect, the present invention provides the following protein variants: (1) a CNTF variant that substitutes valine for the phenylalanine residue at the position 3, 83, 98, 105, 119, 152 or 178 of an amino acid sequence (SEQ ID NO.: 1) of a wild-type CNTF; (2) an EPO variant that substitutes valine for the phenylalanine residue at the position 48, 138, 142 or 148 of an amino acid sequence (SEQ ID NO.: 2) of a wild-type EPO; (3) a Flt3L variant that substitutes valine for the phenylalanine residue at the position 6, 15, 81, 87, 96 or 124 of an amino acid sequence (SEQ ID NO.: 3) of a wild-type Flt3L; (4) a G-CSF variant that substitutes valine for the phenylalanine residue at the position 13, 83, 113, 140, 144 or 160 of an amino acid sequence (SEQ ID NO.: 4) of a wild-type G-CSF; (5) a GM-CSF variant that substitutes valine for the phenylalanine residue at the position 47, 103, 106, 113 or 119 of an amino acid sequence (SEQ ID NO.: 5) of a wild-type GM-CSF; (6) a GH variant that substitutes valine for the phenylalanine residue at the position 1, 10, 25, 31, 44, 54, 92, 97, 139, 146, 166, 176 or 191 of an amino acid sequence (SEQ ID NO.: 6) of a wild-type GH; (7) an IFN-α2A variant that substitutes valine for the phenylalanine residue at the position 27, 36, 38, 43, 47, 64, 67, 84, 123 or 151 of an amino acid sequence (SEQ ID NO.: 7) of a wild-type IFN-α2A; (8) an IFN-α2B variant that substitutes valine for the phenylalanine residue at the position 27, 36, 38, 43, 47, 64, 67, 84, 123 or 151 of an amino acid sequence (SEQ ID NO.: 8) of a wild-type IFN-α2B; (9) an IFN-β variant that substitutes valine for the phenylalanine residue at the position 8, 38, 50, 67, 70, 111 or 154 of an amino acid sequence (SEQ ID NO.: 9) of a wild-type IFN-β; (10) an IFN-γ variant that substitutes valine for the phenylalanine residue at the position 18, 32, 55, 57, 60, 63, 84, 85, 95 or 139 of an amino acid sequence (SEQ ID NO.: 10) of a wild-type IFN-γ; (11) an IFN-ω variant that substitutes valine for the phenylalanine residue at the position 27, 36, 38, 65, 68, 124 or 153 of an amino acid sequence (SEQ ID NO.: 11) of a wild-type IFN-ω; (12) an IFN-τ variant that substitutes valine for the phenylalanine residue at the position 8, 39, 68, 71, 88, 127, 156, 157, 159 or 183 of an amino acid sequence (SEQ ID NO.: 12) of a wild-type IFN-τ; (13) an IL-2 variant that substitutes valine for the phenylalanine residue at the position 42, 44, 78, 103, 117 or 124 of an amino acid sequence (SEQ ID NO.: 13) of a wild-type IL-2; (14) an IL-3 variant that substitutes valine for the phenylalanine residue at the position 37, 61, 107, 113 or 133 of an amino acid sequence (SEQ ID NO.: 14) of a wild-type IL-3; (15) an IL-4 variant that substitutes valine for the phenylalanine residue at the position 33, 45, 55, 73, 82 or 112 of an amino acid sequence (SEQ ID NO.: 15) of a wild-type IL-4; (16) an IL-5 variant that substitutes valine for the phenylalanine residue at the position 49, 69, 96 or 103 of an amino acid sequence (SEQ ID NO.: 16) of a wild-type IL-5; (17) an IL-6 variant that substitutes valine for the phenylalanine residue at the position 73, 77, 93, 104, 124, 169 or 172 of an amino acid sequence (SEQ ID NO.: 17) of a wild-type L-6; (18) an L-12p35 variant that substitutes valine for the phenylalanine residue at the position 13, 39, 82, 96, 116, 132, 150, 166 or 180 of an amino acid sequence (SEQ ID NO.: 18) of a wild-type IL-12p35; (19) a LPT variant that substitutes valine for the phenylalanine residue at the position 41 or 92 of an amino acid sequence (SEQ ID NO.: 19) of a wild-type LPT; (20) a LIF variant that substitutes valine for the phenylalanine residue at the position 41, 52, 67, 70, 156 or 180 of an amino acid sequence (SEQ ID NO.: 20) of a wild-type LIF; (21) a M-CSF variant that substitutes valine for the phenylalanine residue at the position 35, 37, 54, 67, 91, 106, 121, 135, 143, 229, 255, 311, 439, 466 or 485 of an amino acid sequence (SEQ ID NO.: 21) of a wild-type M-CSF; (22) an OSM variant that substitutes valine for the phenylalanine residue at the position 56, 70, 160, 169, 176 or 184 of an amino acid sequence (SEQ ID NO.: 22) of a wild-type OSM; (23) a PL variant that substitutes valine for the phenylalanine residue at the position 10, 31, 44, 52, 54, 92, 97, 146, 166, 176 or 191 of an amino acid sequence (SEQ ID NO.: 23) of a wild-type PL; (24) a SCF variant that substitutes valine for the phenylalanine residue at the position 63, 102, 110, 115, 116, 119, 126, 129, 158, 199, 205, 207 or 245 of an amino acid sequence (SEQ ID NO.: 24) of a wild-type SCF; and (25) a TPO variant that substitutes valine for the phenylalanine residue at the position 46, 128, 131, 141, 186, 204, 240 or 286 of an amino acid sequence (SEQ ID NO.: 25) of a wild-type TPO.

In another specific aspect, the present invention provides the following DNA molecules: (1) a DNA encoding a CNTF variant that substitutes valine for the phenylalanine residue at the position 3, 83, 98, 105, 119, 152 or 178 of an amino acid sequence (SEQ ID NO.: 1) of a wild-type CNTF; (2) a DNA encoding an EPO variant that substitutes valine for the phenylalanine residue at the position 48, 138, 142 or 148 of an amino acid sequence (SEQ ID NO.: 2) of a wild-type EPO; (3) a DNA encoding a Flt3L variant that substitutes valine for the phenylalanine residue at the position 6, 15, 81, 87, 96 or 124 of an amino acid sequence (SEQ ID NO.: 3) of a wild-type Flt3L; (4) a DNA encoding a G-CSF variant that substitutes valine for the phenylalanine residue at the position 13, 83, 113, 140, 144 or 160 of an amino acid sequence (SEQ ID NO.: 4) of a wild-type G-CSF; (5) a DNA encoding a GM-CSF variant that substitutes valine for the phenylalanine residue at the position 47, 103, 106, 113 or 119 of an amino acid sequence (SEQ ID NO.: 5) of a wild-type GM-CSF; (6) a DNA encoding a GH variant that substitutes valine for the phenylalanine residue at the position 1, 10, 25, 31, 44, 54, 92, 97, 139, 146, 166, 176 or 191 of an amino acid sequence (SEQ ID NO.: 6) of a wild-type GH; (7) a DNA encoding an IFN-α2A variant that substitutes valine for the phenylalanine residue at the position 27, 36, 38, 43, 47, 64, 67, 84, 123 or 151 of an amino acid sequence (SEQ ID NO.: 7) of a wild-type IFN-α2A, (8) a DNA encoding an IFN-α2B variant that substitutes valine for the phenylalanine residue at the position 27, 36, 38, 43, 47, 64, 67, 84, 123 or 151 of an amino acid sequence (SEQ ID NO.: 8) of a wild-type IFN-α2B; (9) a DNA encoding an IFN-β variant that substitutes valine for the phenylalanine residue at the position 8, 38, 50, 67, 70, 111 or 154 of an amino acid sequence (SEQ ID NO.: 9) of a wild-type IFN-β; (10) a DNA encoding an IFN-γ variant that substitutes valine for the phenylalanine residue at the position 18, 32, 55, 57, 60, 63, 84, 85, 95 or 139 of an amino acid sequence (SEQ ID NO.: 10) of a wild-type IFN-γ; (11) a DNA encoding an IFN-ω variant that substitutes valine for the phenylalanine residue at the position 27, 36, 38, 65, 68, 124 or 153 of an amino acid sequence (SEQ ID NO.: 11) of a wild-type IFN-ω; (12) a DNA encoding an IFN-τ variant that substitutes valine for the phenylalanine residue at the position 8, 39, 68, 71, 88, 127, 156, 157, 159 or 183 of an amino acid sequence (SEQ ID NO.: 12) of a wild-type IFN-τ; (13) a DNA encoding an IL-2 variant that substitutes valine for the phenylalanine residue at the position 42, 44, 78, 103, 117 or 124 of an amino acid sequence (SEQ ID NO.: 13) of a wild-type IL-2; (14) a DNA encoding an IL-3 variant that substitutes valine for the phenylalanine residue at the position 37, 61, 107, 113 or 133 of an amino acid sequence (SEQ ID NO.: 14) of a wild-type IL-3; (15) a DNA encoding an IL-4 variant that substitutes valine for the phenylalanine residue at the position 33, 45, 55, 73, 82 or 112 of an amino acid sequence (SEQ ID NO.: 15) of a wild-type IL-4; (16) a DNA encoding an IL-5 variant that substitutes valine for the phenylalanine residue at the position 49, 69, 96 or 103 of an amino acid sequence (SEQ ID NO.: 16) of a wild-type IL-5; (17) a DNA encoding an IL-6 variant that substitutes valine for the phenylalanine residue at the position 73, 77, 93, 104, 124, 169 or 172 of an amino acid sequence (SEQ ID NO.: 17) of a wild-type IL-6; (18) a DNA encoding an IL-12p35 variant that substitutes valine for the phenylalanine residue at the position 13, 39, 82, 96, 116, 132, 150, 166 or 180 of an amino acid sequence (SEQ ID NO.: 18) of a wild-type IL-12p35; (19) a DNA encoding a LPT variant that substitutes valine for the phenylalanine residue at the position 41 or 92 of an amino acid sequence (SEQ ID NO.: 19) of a wild-type LPT; (20) a DNA encoding a LIF variant that substitutes valine for the phenylalanine residue at the position 41, 52, 67, 70, 156 or 180 of an amino acid sequence (SEQ ID NO.: 20) of a wild-type LIF; (21) a DNA encoding a M-CSF variant that substitutes valine for the phenylalanine residue at the position 35, 37, 54, 67, 91, 106, 121, 135, 143, 229, 255, 311, 439, 466 or 485 of an amino acid sequence (SEQ ID NO.: 21) of a wild-type M-CSF; (22) a DNA encoding an OSM variant that substitutes valine for the phenylalanine residue at the position 56, 70, 160, 169, 176 or 184 of an amino acid sequence (SEQ ID NO.: 22) of a wild-type OSM; (23) a DNA encoding a PL variant that substitutes valine for the phenylalanine residue at the position 10, 31, 44, 52, 54, 92, 97, 146, 166, 176 or 191 of an amino acid sequence (SEQ ID NO.: 23) of a wild-type PL; (24) a DNA encoding a SCF variant that substitutes valine for the phenylalanine residue at the position 63, 102, 110, 115, 116, 119, 126, 129, 158, 199, 205, 207 or 245 of an amino acid sequence (SEQ ID NO.: 24) of a wild-type SCF; and (25) a DNA encoding a TPO variant that substitutes valine for the phenylalanine residue at the position 46, 128, 131, 141, 186, 204, 240 or 286 of an amino acid sequence (SEQ ID NO.: 25) of a wild-type TPO.

In a further specific aspect, the present invention provides the following recombinant expression vectors: (1) a recombinant expression vector to which a DNA encoding a CNTF variant that substitutes valine for the phenylalanine residue at the position 3, 83, 98, 105, 119, 152 or 178 of an amino acid sequence (SEQ ID NO.: 1) of a wild-type CNTF is operably linked; (2) a recombinant expression vector to which a DNA encoding an EPO variant that substitutes valine for the phenylalanine residue at the position 48, 138, 142 or 148 of an amino acid sequence (SEQ ID NO.: 2) of a wild-type EPO is operably linked; (3) a recombinant expression vector to which a DNA encoding a Flt3L variant that substitutes valine for the phenylalanine residue at the position 6, 15, 81, 87, 96 or 124 of an amino acid sequence (SEQ ID NO.: 3) of a wild-type Flt3L is operably linked; (4) a recombinant expression vector to which a DNA encoding a G-CSF variant that substitutes valine for the phenylalanine residue at the position 13, 83, 113, 140, 144 or 160 of an amino acid sequence (SEQ ID NO.: 4) of a wild-type G-CSF is operably linked; (5) a recombinant expression vector to which a DNA encoding a GM-CSF variant that substitutes valine for the phenylalanine residue at the position 47, 103, 106, 113 or 119 of an amino acid sequence (SEQ ID NO.: 5) of a wild-type GM-CSF is operably linked; (6) a recombinant expression vector to which a DNA encoding a GH variant that substitutes valine for the phenylalanine residue at the position 1, 10, 25, 31, 44, 54, 92, 97, 139, 146, 166, 176 or 191 of an amino acid sequence (SEQ ID NO.: 6) of a wild-type GH is operably linked; (7) a recombinant expression vector to which a DNA encoding an IFN-α2A variant that substitutes valine for the phenylalanine residue at the position 27, 36, 38, 43, 47, 64, 67, 84, 123 or 151 of an amino acid sequence (SEQ ID NO.: 7) of a wild-type IFN-α2A is operably linked; (8) a recombinant expression vector to which a DNA encoding an IFN-α2B variant that substitutes valine for the phenylalanine residue at the position 27, 36, 38, 43, 47, 64, 67, 84, 123 or 151 of an amino acid sequence (SEQ ID NO.: 8) of a wild-type IFN-α2B is operably linked; (9) a recombinant expression vector to which a DNA encoding an IFN-β variant that substitutes valine for the phenylalanine residue at the position 8, 38, 50, 67, 70, 111 or 154 of an amino acid sequence (SEQ ID NO.: 9) of a wild-type IFN-β is operably linked; (10) a recombinant expression vector to which a DNA encoding an IFN-γ variant that substitutes valine for the phenylalanine residue at the position 18, 32, 55, 57, 60, 63, 84, 85, 95 or 139 of an amino acid sequence (SEQ ID NO.: 10) of a wild-type IFN-γ is operably linked; (11) a recombinant expression vector to which a DNA encoding an IFN-ω variant that substitutes valine for the phenylalanine residue at the position 27, 36, 38, 65, 68, 124 or 153 of an amino acid sequence (SEQ ID NO.: 11) of a wild-type IFN-ω is operably linked; (12) a recombinant expression vector to which a DNA encoding an IFN-τ variant that substitutes valine for the phenylalanine residue at the position 8, 39, 68, 71, 88, 127, 156, 157, 159 or 183 of an amino acid sequence (SEQ ID NO.: 12) of a wild-type IFN-τ is operably linked; (13) a recombinant expression vector to which a DNA encoding an IL-2 variant that substitutes valine for the phenylalanine residue at the position 42, 44, 78, 103, 117 or 124 of an amino acid sequence (SEQ ID NO.: 13) of a wild-type IL-2 is operably linked; (14) a recombinant expression vector to which a DNA encoding an IL-3 variant that substitutes valine for the phenylalanine residue at the position 37, 61, 107, 113 or 133 of an amino acid sequence (SEQ ID NO.: 14) of a wild-type IL-3 is operably linked; (15) a recombinant expression vector to which a DNA encoding an IL-4 variant that substitutes valine for the phenylalanine residue at the position 33, 45, 55, 73, 82 or 112 of an amino acid sequence (SEQ ID NO.: 15) of a wild-type IL-4 is operably linked; (16) a recombinant expression vector to which a DNA encoding an IL-5 variant that substitutes valine for the phenylalanine residue at the position 49, 69, 96 or 103 of an amino acid sequence (SEQ ID NO.: 16) of a wild-type IL-5 is operably linked; (17) a recombinant expression vector to which a DNA encoding an IL-6 variant that substitutes valine for the phenylalanine residue at the position 73, 77, 93, 104, 124, 169 or 172 of an amino acid sequence (SEQ ID NO.: 17) of a wild-type IL-6 is operably linked; (18) a recombinant expression vector to which a DNA encoding an IL-12p35 variant that substitutes valine for the phenylalanine residue at the position 13, 39, 82,96, 116, 132, 150, 166 or 180 of an amino acid sequence (SEQ ID NO.: 18) of a wild-type IL-12p35 is operably linked; (19) a recombinant expression vector to which a DNA encoding a LPT variant that substitutes valine for the phenylalanine residue at the position 41 or 92 of an amino acid sequence (SEQ ID NO.: 19) of a wild-type LPT is operably linked; (20) a recombinant expression vector to which a DNA encoding a LIF variant that substitutes valine for the phenylalanine residue at the position 41, 52, 67, 70, 156 or 180 of an amino acid sequence (SEQ ID NO.: 20) of a wild-type LIF is operably linked; (21) a recombinant expression vector to which a DNA encoding a M-CSF variant that substitutes valine for the phenylalanine residue at the position 35, 37, 54, 67, 91, 106, 121, 135, 143, 229, 255, 311, 439, 466 or 485 of an amino acid sequence (SEQ ID NO.: 21) of a wild-type M-CSF is operably linked; (22) a recombinant expression vector to which a DNA encoding an OSM variant that substitutes valine for the phenylalanine residue at the position 56, 70, 160, 169, 176 or 184 of an amino acid sequence (SEQ ID NO.: 22) of a wild-type OSM is operably linked; (23) a recombinant expression vector to which a DNA encoding a PL variant that substitutes valine for the phenylalanine residue at the position 10, 31, 44, 52, 54, 92, 97, 146, 166, 176 or 191 of an amino acid sequence (SEQ ID NO.: 23) of a wild-type PL is operably linked; (24) a recombinant expression vector to which a DNA encoding a SCF variant that substitutes valine for the phenylalanine residue at the position 63, 102, 110, 115, 116, 119, 126, 129, 158, 199, 205, 207 or 245 of an amino acid sequence (SEQ ID NO.: 24) of a wild-type SCF is operably linked; and (25) a recombinant expression vector to which a DNA encoding a TPO variant that substitutes valine for the phenylalanine residue at the position 46, 128, 131, 141, 186, 204, 240 or 286 of an amino acid sequence (SEQ ID NO.: 25) of a wild-type TPO is operably linked In yet another specific aspect, the present invention provides the following host cells: (1) a host cell transformed or transfected with a recombinant expression vector to which a DNA encoding a CNTF variant that substitutes valine for the phenylalanine residue at the position 3, 83, 98, 105, 119, 152 or 178 of an amino acid sequence (SEQ ID NO.: 1) of a wild-type CNTF is operably linked; (2) a host cell transformed or transfected with a recombinant expression vector to which a DNA encoding an EPO variant that substitutes valine for the phenylalanine residue at the position 48, 138, 142 or 148 of an amino acid sequence (SEQ ID NO.: 2) of a wild-type EPO is operably linked; (3) a host cell transformed or transfected with a recombinant expression vector to which a DNA encoding a Flt3L variant that substitutes valine for the phenylalanine residue at the position 6, 15, 81, 87, 96 or 124 of an amino acid sequence (SEQ ID NO.: 3) of a wild-type Flt3L is operably linked; (4) a host cell transformed or transfected with a recombinant expression vector to which a DNA encoding a G-CSF variant that substitutes valine for the phenylalanine residue at the position 13, 83, 113, 140, 144 or 160 of an amino acid sequence (SEQ ID NO.: 4) of a wild-type G-CSF is operably linked; (5) a host cell transformed or transfected with a recombinant expression vector to which a DNA encoding a GM-CSF variant that substitutes valine for the phenylalanine residue at the position 47, 103, 106, 113 or 119 of an amino acid sequence (SEQ ID NO.: 5) of a wild-type GM-CSF is operably linked; (6) a host cell transformed or transfected with a recombinant expression vector to which a DNA encoding a GH variant that substitutes valine for the phenylalanine residue at the position 1, 10, 25, 31, 44, 54, 92, 97, 139, 146, 166, 176 or 191 of an amino acid sequence (SEQ ID NO.: 6) of a wild-type GH is operably linked; (7) a host cell transformed or transfected with a recombinant expression vector to which a DNA encoding an IFN-α2A variant that substitutes valine for the phenylalanine residue at the position 27, 36, 38, 43, 47, 64, 67, 84, 123 or 151 of an amino acid sequence (SEQ ID NO.: 7) of a wild-type IFN-α2A is operably linked; (8) a host cell transformed or transfected with a recombinant expression vector to which a DNA encoding an IFN-α2B variant that substitutes valine for the phenylalanine residue at the position 27, 36, 38, 43, 47, 64, 67, 84, 123 or 151 of an amino acid sequence (SEQ ID NO.: 8) of a wild-type IFN-α2B is operably linked; (9) a host cell transformed or transfected with a recombinant expression vector to which a DNA encoding an IFN-β variant that substitutes valine for the phenylalanine residue at the position 8, 38, 50, 67, 70, 111 or 154 of an amino acid sequence (SEQ ID NO.: 9) of a wild-type IFN-β is operably linked; (10) a host cell transformed or transfected with a recombinant expression vector to which a DNA encoding an IFN-γ variant that substitutes valine for the phenylalanine residue at the position 18, 32, 55, 57, 60, 63, 84, 85, 95 or 139 of an amino acid sequence (SEQ ID NO.: 10) of a wild-type IFN-γ is operably linked; (11) a host cell transformed or transfected with a recombinant expression vector to which a DNA encoding an IFN-ω variant that substitutes valine for the phenylalanine residue at the position 27, 36, 38, 65, 68, 124 or 153 of an amino acid sequence (SEQ ID NO.: 11) of a wild-type IFN-ω is operably linked; (12) a host cell transformed or transfected with a recombinant expression vector to which a DNA encoding an IFN-τ variant that substitutes valine for the phenylalanine residue at the position 8, 39, 68, 71, 88, 127, 156, 157, 159 or 183 of an amino acid sequence (SEQ ID NO.: 12) of a wild-type IFN-τ is operably linked; (13) a host cell transformed or transfected with a recombinant expression vector to which a DNA encoding an IL-2 variant that substitutes valine for the phenylalanine residue at the position 42, 44, 78, 103, 117 or 124 of an amino acid sequence (SEQ ID NO.: 13) of a wild-type IL-2 is operably linked; (14) a host cell transformed or transfected with a recombinant expression vector to which a DNA encoding an IL-3 variant that substitutes valine for the phenylalanine residue at the position 37, 61, 107, 113 or 133 of an amino acid sequence (SEQ ID NO.: 14) of a wild-type IL-3 is operably linked; (15) a host cell transformed or transfected with a recombinant expression vector to which a DNA encoding an IL-4 variant that substitutes valine for the phenylalanine residue at the position 33, 45, 55, 73, 82 or 112 of an amino acid sequence (SEQ ID NO.: 15) of a wild-type IL-4 is operably linked; (16) a host cell transformed or transfected with a recombinant expression vector to which a DNA encoding an IL-5 variant that substitutes valine for the phenylalanine residue at the position 49, 69, 96 or 103 of an amino acid sequence (SEQ ID NO.: 16) of a wild-type IL-5 is operably linked; (17) a host cell transformed or transfected with a recombinant expression vector to which a DNA encoding an IL-6 variant that substitutes valine for the phenylalanine residue at the position 73, 77, 93, 104, 124, 169 or 172 of an amino acid sequence (SEQ ID NO.: 17) of a wild-type IL-6 is operably linked; (18) a host cell transformed or transfected with a recombinant expression vector to which a DNA encoding an IL-12p35 variant that substitutes valine for the phenylalanine residue at the position 13, 39, 82, 96, 116, 132, 150, 166 or 180 of an amino acid sequence (SEQ ID NO.: 18) of a wild-type IL-12p35 is operably linked; (19) a host cell transformed or transfected with a recombinant expression vector to which a DNA encoding a LPT variant that substitutes valine for the phenylalanine residue at the position 41 or 92 of an amino acid sequence (SEQ ID NO.: 19) of a wild-type LPT is operably linked; (20) a host cell transformed or transfected with a recombinant expression vector to which a DNA encoding a LIF variant that substitutes valine for the phenylalanine residue at the position 41, 52, 67, 70, 156 or 180 of an amino acid sequence (SEQ ID NO.: 20) of a wild-type LIF is operably linked; (21) a host cell transformed or transfected with a recombinant expression vector to which a DNA encoding a M-CSF variant that substitutes valine for the phenylalanine residue at the position 35, 37, 54, 67, 91, 106, 121, 135, 143, 229, 255, 311, 439, 466 or 485 of an amino acid sequence (SEQ ID NO.: 21) of a wild-type M-CSF is operably linked; (22) a host cell transformed or transfected with a recombinant expression vector to which a DNA encoding an OSM variant that substitutes valine for the phenylalanine residue at the position 56, 70, 160, 169, 176 or 184 of an amino acid sequence (SEQ ID NO.: 22) of a wild-type OSM is operably linked; (23) a host cell transformed or transfected with a recombinant expression vector to which a DNA encoding a PL variant that substitutes valine for the phenylalanine residue at the position 10, 31, 44, 52, 54, 92, 97, 146, 166, 176 or 191 of an amino acid sequence (SEQ ID NO.: 23) of a wild-type PL is operably linked; (24) a host cell transformed or transfected with a recombinant expression vector to which a DNA encoding a SCF variant that substitutes valine for the phenylalanine residue at the position 63, 102, 110, 115, 116, 119, 126, 129, 158, 199, 205, 207 or 245 of an amino acid sequence (SEQ ID NO.: 24) of a wild-type SCF is operably linked; and (25) a host cell transformed or transfected with a recombinant expression vector to which a DNA encoding a TPO variant that substitutes valine for the phenylalanine residue at the position 46, 128, 131, 141, 186, 204, 240 or 286 of an amino acid sequence (SEQ ID NO.: 25) of a wild-type TPO is operably linked.

In still another specific aspect, the present invention provides the following methods of preparing a protein variant: (1) a method of preparing a protein variant, comprising cultivating a host cell transformed or transfected with a recombinant expression vector to which a DNA encoding a CNTF variant that substitutes valine for the phenylalanine residue at the position 3, 83, 98, 105, 119, 152 or 178 of an amino acid sequence (SEQ ID NO.: 1) of a wild-type CNTF is operably linked, and isolating the protein variant from a resulting culture; (2) a method of preparing a protein variant, comprising cultivating a host cell transformed or transfected with a recombinant expression vector to which a DNA encoding an EPO variant that substitutes valine for the phenylalanine residue at the position 48, 138, 142 or 148 of an amino acid sequence (SEQ ID NO.: 2) of a wild-type EPO is operably linked, and isolating the protein variant from a resulting culture; (3) a method of preparing a protein variant, comprising cultivating a host cell transformed or transfected with a recombinant expression vector to which a DNA encoding a Flt3L variant that substitutes valine for the phenylalanine residue at the position 6, 15, 81, 87, 96 or 124 of an amino acid sequence (SEQ ID NO.: 3) of a wild-type Flt3L is operably linked, and isolating the protein variant from a resulting culture; (4) a method of preparing a protein variant, comprising cultivating a host cell transformed or transfected with a recombinant expression vector to which a DNA encoding a G-CSF variant that substitutes valine for the phenylalanine residue at the position 13, 83, 113, 140, 144 or 160 of an amino acid sequence (SEQ ID NO.: 4) of a wild-type G-CSF is operably linked, and isolating the protein variant from a resulting culture; (5) a method of preparing a protein variant, comprising cultivating a host cell transformed or transfected with a recombinant expression vector to which a DNA encoding a GM-CSF variant that substitutes valine for the phenylalanine residue at the position 47, 103, 106, 113 or 119 of an amino acid sequence (SEQ ID NO.: 5) of a wild-type GM-CSF is operably linked, and isolating the protein variant from a resulting culture; (6) a method of preparing a protein variant, comprising cultivating a host cell transformed or transfected with a recombinant expression vector to which a DNA encoding a GH variant that substitutes valine for the phenylalanine residue at the position 1, 10, 25, 31, 44, 54, 92, 97, 139, 146, 166, 176 or 191 of an amino acid sequence (SEQ ID NO.: 6) of a wild-type GH is operably linked, and isolating the protein variant from a resulting culture; (7) a method of preparing a protein variant, comprising cultivating a host cell transformed or transfected with a recombinant expression vector to which a DNA encoding an IFN-α2A variant that substitutes valine for the phenylalanine residue at the position 27, 36, 38, 43, 47, 64, 67, 84, 123 or 151 of an amino acid sequence (SEQ ID NO.: 7) of a wild-type IFN-α2A is operably linked, and isolating the protein variant from a resulting culture; (8) a method of preparing a protein variant, comprising cultivating a host cell transformed or transfected with a recombinant expression vector to which a DNA encoding an IFN-α2B variant that substitutes valine for the phenylalanine residue at the position 27, 36, 38, 43, 47, 64, 67, 84, 123 or 151 of an amino acid sequence (SEQ ID NO.: 8) of a wild-type IFN-α2B is operably linked, and isolating the protein variant from a resulting culture; (9) a method of preparing a protein variant, comprising cultivating a host cell transformed or transfected with a recombinant expression vector to which a DNA encoding an IFN-β variant that substitutes valine for the phenylalanine residue at the position 8, 38, 50, 67, 70, 111 or 154 of an amino acid sequence (SEQ ID NO.: 9) of a wild-type IFN-β is operably linked, and isolating the protein variant from a resulting culture; (10) a method of preparing a protein variant, comprising cultivating a host cell transformed or transfected with a recombinant expression vector to which a DNA encoding an IFN-γ variant that substitutes valine for the phenylalanine residue at the position 18, 32, 55, 57, 60, 63, 84, 85, 95 or 139 of an amino acid sequence (SEQ ID NO.: 10) of a wild-type IFN-γ is operably linked, and isolating the protein variant from a resulting culture; (11) a method of preparing a protein variant, comprising cultivating a host cell transformed or transfected with a recombinant expression vector to which a DNA encoding an IFN-ω variant that substitutes valine for the phenylalanine residue at the position 27, 36, 38, 65, 68, 124 or 153 of an amino acid sequence (SEQ ID NO.: 11) of a wild-type IFN-ω is operably linked, and isolating the protein variant from a resulting culture; (12) a method of preparing a protein variant, comprising cultivating a host cell transformed or transfected with a recombinant expression vector to which a DNA encoding an IFN-τ variant that substitutes valine for the phenylalanine residue at the position 8, 39, 68, 71, 88, 127, 156, 157, 159 or 183 of an amino acid sequence (SEQ ID NO.: 12) of a wild-type IFN-τ is operably linked, and isolating the protein variant from a resulting culture; (13) a method of preparing a protein variant, comprising cultivating a host cell transformed or transfected with a recombinant expression vector to which a DNA encoding an IL-2 variant that substitutes valine for the phenylalanine residue at the position 42, 44, 78, 103, 117 or 124 of an amino acid sequence (SEQ ID NO.: 13) of a wild-type IL-2 is operably linked, and isolating the protein variant from a resulting culture; (14) a method of preparing a protein variant, comprising cultivating a host cell transformed or transfected with a recombinant expression vector to which a DNA encoding an IL-3 variant that substitutes valine for the phenylalanine residue at the position 37, 61, 107, 113 or 133 of an amino acid sequence (SEQ ID NO.: 14) of a wild-type IL-3 is operably linked, and isolating the protein variant from a resulting culture; (15) a method of preparing a protein variant, comprising cultivating a host cell transformed or transfected with a recombinant expression vector to which a DNA encoding an IL-4 variant that substitutes valine for the phenylalanine residue at the position 33, 45, 55, 73, 82 or 112 of an amino acid sequence (SEQ ID NO.: 15) of a wild-type IL-4 is operably linked, and isolating the protein variant from a resulting culture; (16) a method of preparing a protein variant, comprising cultivating a host cell transformed or transfected with a recombinant expression vector to which a DNA encoding an IL-5 variant that substitutes valine for the phenylalanine residue at the position 49, 69, 96 or 103 of an amino acid sequence (SEQ ID NO.: 16) of a wild-type IL-5 is operably linked, and isolating the protein variant from a resulting culture; (17) a method of preparing a protein variant, comprising cultivating a host cell transformed or transfected with a recombinant expression vector to which a DNA encoding an IL-6 variant that substitutes valine for the phenylalanine residue at the position 73, 77, 93, 104, 124, 169 or 172 of an amino acid sequence (SEQ ID NO.: 17) of a wild-type IL-6 is operably linked, and isolating the protein variant from a resulting culture; (18) a method of preparing a protein variant, comprising cultivating a host cell transformed or transfected with a recombinant expression vector to which a DNA encoding an IL-12p35 variant that substitutes valine for the phenylalanine residue at the position 13, 39, 82, 96, 116, 132, 150, 166 or 180 of an amino acid sequence (SEQ ID NO.: 18) of a wild-type IL-12p35 is operably linked, and isolating the protein variant from a resulting culture; (19) a method of preparing a protein variant, comprising cultivating a host cell transformed or transfected with a recombinant expression vector to which a DNA encoding a LPT variant that substitutes valine for the phenylalanine residue at the position 41 or 92 of an amino acid sequence (SEQ ID NO.: 19) of a wild-type LPT is operably linked, and isolating the protein variant from a resulting culture; (20) a method of preparing a protein variant, comprising cultivating a host cell transformed or transfected with a recombinant expression vector to which a DNA encoding a LIF variant that substitutes valine for the phenylalanine residue at the position 41, 52, 67, 70, 156 or 180 of an amino acid sequence (SEQ ID NO.: 20) of a wild-type LIF is operably linked, and isolating the protein variant from a resulting culture; (21) a method of preparing a protein variant, comprising cultivating a host cell transformed or transfected with a recombinant expression vector to which a DNA encoding a M-CSF variant that substitutes valine for the phenylalanine residue at the position 35, 37, 54, 67, 91, 106, 121, 135, 143, 229, 255, 311, 439, 466 or 485 of an amino acid sequence (SEQ ID NO.: 21) of a wild-type M-CSF is operably linked, and isolating the protein variant from a resulting culture; (22) a method of preparing a protein variant, comprising cultivating a host cell transformed or transfected with a recombinant expression vector to which a DNA encoding an OSM variant that substitutes valine for the phenylalanine residue at the position 56, 70, 160, 169, 176 or 184 of an amino acid sequence (SEQ ID NO.: 22) of a wild-type OSM is operably linked, and isolating the protein variant from a resulting culture; (23) a method of preparing a protein variant, comprising cultivating a host cell transformed or transfected with a recombinant expression vector to which a DNA encoding a PL variant that substitutes valine for the phenylalanine residue at the position 10, 31, 44, 52, 54, 92, 97, 146, 166, 176 or 191 of an amino acid sequence (SEQ ID NO.: 23) of a wild-type PL is operably linked, and isolating the protein variant from a resulting culture; (24) a method of preparing a protein variant, comprising cultivating a host cell transformed or transfected with a recombinant expression vector to which a DNA encoding a SCF variant that substitutes valine for the phenylalanine residue at the position 63, 102, 110, 115, 116, 119, 126, 129, 158, 199, 205, 207 or 245 of an amino acid sequence (SEQ ID NO.: 24) of a wild-type SCF is operably linked, and isolating the protein variant from a resulting culture; and (25) a method of preparing a protein variant, comprising cultivating a host cell transformed or transfected with a recombinant expression vector to which a DNA encoding a TPO variant that substitutes valine for the phenylalanine residue at the position 46, 128, 131, 141, 186, 204, 240 or 286 of an amino acid sequence (SEQ ID NO.: 25) of a wild-type TPO is operably linked, and isolating the protein variant from a resulting culture.

In still another specific aspect the present invention provides the following pharmaceutical compositions: (1) a pharmaceutical composition comprising a CNTF variant that substitutes valine for the phenylalanine residue at the position 3, 83, 98, 105, 119, 152 or 178 of an amino acid sequence (SEQ ID NO.: 1) of a wild-type CNTF and a pharmaceutically acceptable carrier, (2) a pharmaceutical composition comprising an EPO variant that substitutes valine for the phenylalanine residue at the position 48, 138, 142 or 148 of an amino acid sequence (SEQ ID NO.: 2) of a wild-type EPO and a pharmaceutically acceptable carrier, (3) a pharmaceutical composition comprising a Flt3L variant that substitutes valine for the phenylalanine residue at the position 6, 15, 81, 87, 96 or 124 of an amino acid sequence (SEQ ID NO.: 3) of a wild-type Flt3L and a pharmaceutically acceptable carrier, (4) a pharmaceutical composition comprising a G-CSF variant that substitutes valine for the phenylalanine residue at the position 13, 83, 113, 140, 144 or 160 of an amino acid sequence (SEQ ID NO.: 4) of a wild-type G-CSF and a pharmaceutically acceptable carrier, (5) a pharmaceutical composition comprising a GM-CSF variant that substitutes valine for the phenylalanine residue at the position 47, 103, 106, 113 or 119 of an amino acid sequence (SEQ ID NO.: 5) of a wild-type GM-CSF and a pharmaceutically acceptable carrier, (6) a pharmaceutical composition comprising a GH variant that substitutes valine for the phenylalanine residue at the position 1, 10, 25, 31, 44, 54, 92, 97, 139, 146, 166, 176 or 191 of an amino acid sequence (SEQ ID NO.: 6) of a wild-type GH and a pharmaceutically acceptable carrier, (7) a pharmaceutical composition comprising an IFN-α2A variant that substitutes valine for the phenylalanine residue at the position 27, 36, 38, 43, 47, 64, 67, 84, 123 or 151 of an amino acid sequence (SEQ ID NO.: 7) of a wild-type IFN-α2A and a pharmaceutically acceptable carrier, (8) a pharmaceutical composition comprising an IFN-α2B variant that substitutes valine for the phenylalanine residue at the position 27, 36, 38, 43, 47, 64, 67, 84, 123 or 151 of an amino acid sequence (SEQ ID NO.: 8) of a wild-type IFN-α2B and a pharmaceutically acceptable carrier, (9) a pharmaceutical composition comprising an IFN-β variant that substitutes valine for the phenylalanine residue at the position 8, 38, 50, 67, 70, 111 or 154 of an amino acid sequence (SEQ ID NO.: 9) of a wild-type IFN-β and a pharmaceutically acceptable carrier; (10) a pharmaceutical composition comprising an IFN-γ variant that substitutes valine for the phenylalanine residue at the position 18, 32, 55, 57, 60, 63, 84, 85, 95 or 139 of an amino acid sequence (SEQ ID NO.: 10) of a wild-type IFN-γ and a pharmaceutically acceptable carrier, (11) a pharmaceutical composition comprising an IFN-ω variant that substitutes valine for the phenylalanine residue at the position 27, 36, 38, 65, 68, 124 or 153 of an amino acid sequence (SEQ ID NO.: 11) of a wild-type IFN-ω and a pharmaceutically acceptable carrier, (12) a pharmaceutical composition comprising an IFN-τ variant that substitutes valine for the phenylalanine residue at the position 8, 39, 68, 71, 88, 127, 156, 157, 159 or 183 of an amino acid sequence (SEQ ID NO.: 12) of a wild-type IFN-τ and a pharmaceutically acceptable carrier, (13) a pharmaceutical composition comprising an IL-2 variant that substitutes valine for the phenylalanine residue at the position 42, 44, 78, 103, 117 or 124 of an amino acid sequence (SEQ ID NO.: 13) of a wild-type IL-2 and a pharmaceutically acceptable carrier; (14) a pharmaceutical composition comprising an IL-3 variant that substitutes valine for the phenylalanine residue at the position 37, 61, 107, 113 or 133 of an amino acid sequence (SEQ ID NO.: 14) of a wild-type IL-3 and a pharmaceutically acceptable carrier, (15) a pharmaceutical composition comprising an IL-4 variant that substitutes valine for the phenylalanine residue at the position 33, 45, 55, 73, 82 or 112 of an amino acid sequence (SEQ ID NO.: 15) of a wild-type IL-4 and a pharmaceutically acceptable carrier, (16) a pharmaceutical composition comprising an IL-5 variant that substitutes valine for the phenylalanine residue at the position 49, 69, 96 or 103 of an amino acid sequence (SEQ ID NO.: 16) of a wild-type IL-5 and a pharmaceutically acceptable carrier, (17) a pharmaceutical composition comprising an IL-6 variant that substitutes valine for the phenylalanine residue at the position 73, 77, 93, 104, 124, 169 or 172 of an amino acid sequence (SEQ ID NO.: 17) of a wild-type IL-6 and a pharmaceutically acceptable carrier, (18) a pharmaceutical composition comprising an IL12p35 variant that substitutes valine for the phenylalanine residue at the position 13, 39, 82, 96, 116, 132, 150, 166 or 180 of an amino acid sequence (SEQ ID NO.: 18) of a wild-type IL-12p35 and a pharmaceutically acceptable carrier, (19) a pharmaceutical composition comprising a LPT variant that substitutes valine for the phenylalanine residue at the position 41 or 92 of an amino acid sequence (SEQ ID NO.: 19) of a wild-type LPT and a pharmaceutically acceptable carrier, (20) a pharmaceutical composition comprising a LIF variant that substitutes valine for the phenylalanine residue at the position 41, 52, 67, 70, 156 or 180 of an amino acid sequence (SEQ ID NO.: 20) of a wild-type LIF and a pharmaceutically acceptable carrier, (21) a pharmaceutical composition comprising a M-CSF variant that substitutes valine for the phenylalanine residue at the position 35, 37, 54, 67, 91, 106, 121, 135, 143, 229, 255, 311, 439, 466 or 485 of an amino acid sequence (SEQ ID NO.: 21) of a wild-type M-CSF and a pharmaceutically acceptable carrier, (22) a pharmaceutical composition comprising an OSM variant that substitutes valine for the phenylalanine residue at the position 56, 70, 160, 169, 176 or 184 of an amino acid sequence (SEQ ID NO.: 22) of a wild-type OSM and a pharmaceutically acceptable carrier, (23) a pharmaceutical composition comprising a PL variant that substitutes valine for the phenylalanine residue at the position 10, 31, 44, 52, 54, 92, 97, 146, 166, 176 or 191 of an amino acid sequence (SEQ ID NO.: 23) of a wild-type PL and a pharmaceutically acceptable carrier, (24) a pharmaceutical composition comprising a SCF variant that substitutes valine for the phenylalanine residue at the position 63, 102, 110, 115, 116, 119, 126, 129, 158, 199, 205, 207 or 245 of an amino acid sequence (SEQ ID NO.: 24) of a wild-type SCF and a pharmaceutically acceptable carrier, and (25) a pharmaceutical composition comprising a TPO variant that substitutes valine for the phenylalanine residue at the position 46, 128, 131, 141, 186, 204, 240 or 286 of an amino acid sequence (SEQ ID NO.: 25) of a wild-type TPO and a pharmaceutically acceptable carrier.

The present purpose to improve the efficacy in modulating biological responses was accomplished in the following examples using TPO, EPO, G-CSF and GH. It will be apparent to those skilled in the art that the following examples are provided only to illustrate the present invention, and the scope of the present invention is not limited to the examples.

EXAMPLE 1

Construction of DNA Coding Wild Type TPO/EPO/G-CSF/GH

A. Construction of DNA Coding Wild Type TPO

750 µl of TRIzol reagent (MRC., USA) was added to bone marrow tissue in a microcentrifuge tube and incubated at room temperature for 5 minutes. 200 µl of chloroform was added into the tube and then the tube was shaken vigorously for 15 seconds. After incubating the tube at room temperature for 2-3 minutes, it was centrifuged at 15,000 rpm for 15 minutes at 4° C. The upper phase was transferred to a 1.5 ml tube and 500 µl of isopropanol was added. The sample was incubated at −70° C. for 30 minutes and centrifuged at 15,000 rpm for 15 minutes at 4° C. After discarding supernatant, RNA pellet was washed once with 75% DEPC ethanol by vortexing and centrifuged at 15,000 rpm for 15 minutes at 4° C. The supernatant was removed and the RNA pellet was dried for 5 minutes at room temperature and then the pellet was dissolved in 50 µl of DEPC-treated 3° distilled water.

2 µg of mRNA purified as above and 1 µl of oligo dT30 primer (10 µM, PROMEGA, USA) were mixed and heated at 70° C. for 2 minutes and then it was immediately cooled on ice for 2 minutes. After that, this reaction mixture was added with 200 U M-MLV reverse transcriptase (PROMEGA, USA), 10 µl of 5× reaction buffer (250 mM Tris-HCl, pH 8.3, 375 mM KCl, 15 mM MgCl.sub.2, 50 nM DTT), 1 µl of dNTP (10 mM DATP, 10 mM dTTP, 10 mM dGTP, 10 mM dCTP) and DEPC-treated 3° C. water was added to make the total volume of 50 µl. After mixing gently, the reaction mixture was incubated at 42° C. for 60 minutes.

To amplify cDNA coding wild type TPO, the first strand cDNA as template, primer 1 and primer 2 (Table 1) were added into a PCR tube including 2 U of pfu DNA polymerase (STRATAGENE, USA), 10 µl of 10× reaction buffer, 1% TRITON X-100, 1 mg/ml BSA, 3 µl of primer 1 (10 µM), 3 µl of primer 2 (10 µM), 2 µl of dNTP (10 mM dATP, 10 mM dTTP, 10 mM dGTP, 10 mM dCTP), and distilled water was added to make the total volume of 100 µl. The PCR reaction condition was as follows; 1 cycle at 95° C. for 3 minutes, and then 30 cycles at 95° C. for 30 seconds, at 52° C. for 1 minute, and at 72° C. for 1.5 minutes, and finally 1 cycle at 72° C. for 10 minutes to make PCR product with completely blunt end.

The PCR product obtained was separated in 0.8% agarose gel (BMA, USA) and was purified with Qiaex II gel extraction kit (QIAGEN, USA). After the isolated DNA was mixed with 15 U of EcoRI 10 U of NotI, 3 µl of 10× reaction buffer and 3° C. distilled water was added to make the total volume of 30 µl DNA was restricted by incubation at 37° C. for 2 hours. The PCR product was separated in 0.8% agarose gel and was purified with Qiaex II gel extraction kit.

After 5 µg of PBLUESCRIPT KS II(+) vector was mixed with 15 U of EcoRI, 10 U of NotI, 3 µl of 10× reaction buffer and 3° C. distilled water was added to make the total volume of 30 µl, DNA was restricted by incubation at 37° C. for 2 hours. The restricted PBLUESCRIPT KS II(+) vector was separated in 0.8% agarose gel and was purified with Qiaex II gel extraction kit.

100 ng of the digested pBluescript KS II(+) vector was ligated with 20 ng of the PCR product which was digested with same enzymes. This ligation mixture was incubated at 16° C. water bath for 16 hours, thus producing a recombinant vector comprising cDNA coding wild type TPO. Then, it was transformed into a E.coli Top10(INVITROGEN, USA) which was made to a competent cell by rubidium chloride method. The transformed bacteria was cultured on LB agar plate containing 50 µg/ml of ampicillin (SIGMA, USA). After overnight incubation, colonies were transferred into tubes with 3 ml of LB medium containing 50 µg/ml ampicillin and then they were cultured at 37° C. for 16 hours. Plasmid was isolated from the cultured bacteria with alkaline lysis method and the restriction of EcoRI/NotI was used to detect inclusion of cloned gene in the plasmid.

B. Construction of DNA Coding Wild Type EPO

Procedure of cloning DNA coding wild type EPO was basically same to that used for cloning DNA coding wild type TPO.

The first strand cDNA as template, primer 11 and primer 12 (Table 2) were used for PCR amplification of DNA coding wild type EPO. The PCR product and cloning vector, pBluescript KS II(+) were digested with both EcoRI and BamHI endonucleases. The digested PCR product and cloning vector were ligated and transformed into competent cell, E.coli Top10(INVITROGEN, USA). Plasmid was isolated from the cultured bacteria with alkaline lysis method and the restriction of EcoRI/BamHI was used to detect existence of cloned gene in the plasmid.

C. Construction of DNA Coding Wild Type G-CSF

Construction procedure of DNA coding wild type G-CSF was similar to that used for DNA coding wild type TPO.

Leukocytes from healthy people were used for the mRNA extraction, and primers 21 and 22 (Table 3) were used for PCR amplification of cDNA coding wild type G-CSF. Both the PCR product and cloning vector, pBluescript KS II(+) were digested with SmaI and EcoRI endonuclease. The digested PCR product and cloning vector were ligated and transformed into competent cell, *E.coli* Top10 (INVITROGEN, USA). Plasmid was isolated from the cultured bacteria with alkaline lysis method and the restriction of SmaI/EcoRI was used to detect existence of cloned gene in the plasmid.

D. Construction of DNA Coding Wild Type GH

DNA coding wild type GH was purchased from ATCC (ATCC No. 67097). To add leader sequence to N-terminal end of this cDNA, primer 35 and 36 (Table 4) were used for PCR. In order to make complete cDNA coding wild type GH linked to the leader sequence, secondary PCR was carried out using primers 37 and 38 (Table 4). The PCR product and cloning vector, pBluescript KS II(+) were digested with EcoRI and HindIII endonuclease. Plasmid was isolated from the cultured bacteria with alkaline lysis method and the restriction of EcoRI/HindIII was used to detect existence of cloned gene in the plasmid

EXAMPLE 2

Construction of cDNA coding TPO/EPO/G-CSF/GH Muteins

A. Construction of cDNAs Coding TPO Muteins

Four muteins of TPO, TPO-[F46V], TPO-[F128V], TPO-[F131V] and TPO-[F141V] were constructed according to procedures as follows to have a single amino acid-substitution from phenylalanine to valine at each positions, respectively.

was used as a megaprimer in the secondary PCR together with universal primer T7(10 pmole). The cDNA coding wild type TPO cloned in pBluescript KS II(+) was used as the template in the secondary PCR. The secondary PCR was performed by adding 2.5 U Ex taq, 5 μl of 10× buffer, 2.5 mM dNTP and D.W was added to make the total volume of 50 μl. The PCR condition consist of 1 cycle at 94° C. for 3 minutes followed by 30 cycles at 94° C. for 1 minute, at 58° C. for 1 minute, and at 72° C. for 1.5 minutes and finally linked to 1 cycle at 72° C. for 7 minutes prior to termination.

To minimize errors derived form DNA synthesis, $Mg^{2+}$ concentration was reduced to 1 mM in the primary PCR. Sizes of megaprimers amplified were 280 b.p for TPO-[F46V], 520 b.p for TPO-[F128V], 530 b.p for TPO-[F131V] and 560 b.p for TPO-[F141V]. In the secondary PCR using megaprimers, cDNA coding each muteins produced showed the same size of 1062 b.p. Substitution from phenylalanine to valine at nucleotide sequence of the individual TPO mutein was verified by direct sequencing.

Each PCR product of 1062 b.p was separated in 0.8% agarose gel and purified with Qiaex II gel extraction kit. The PCT product was digested with 15 U EcoRI and 10 U NotI at 37° C. for 2 hours. The digested PCR product was separated in 0.8% agarose gel and purified with Qiaex II gel extraction kit and ligated with pBluescript KS II(+) as described above. The recombinant expression vector containing DNA which codes TPO-[F141V] was named Tefficacin-4 and was deposited at the KCCM (Korean Culture Center of Microorganisms) under the Budapest Treaty on Jun. 9, 2003. Accession number given by international depositary authority was KCCM-10500.

TABLE 1

Primers used in constructing cDNAs coding TPO- wild type and muteins

| | Primer No. | | Nucleotide sequence | Sequence No. |
|---|---|---|---|---|
| 1 | Wild type TPO | Sense | 5'-CGGAATTCCG<u>ATG</u>GAGCTGACTGAATTG-3' | 26 |
| 2 | | Antisense | 5'-TTTAGCGGCCGCATTC<u>TTA</u>CCCTTCCTGAG-3' | 27 |
| 3 | TPO-[F46V] | Sense | T3 | |
| 4 | | Antisense | 5'-CCAAGCTAACGTCCACAGCAG-3' | 28 |
| 5 | TPO-[F128V] | Sense | T3 | |
| 6 | | antisense | 5'-GCTCAGGACGATGGGAT-3' | 29 |
| 7 | TPO-[F131V] | Sence | T3 | |
| 8 | | antisense | 5'-GGTGTTGGACGCTCAGGAAGATG-3' | 30 |
| 9 | TPO-[F141V] | Sense | T3 | |
| 10 | | antisense | 5'-CATCAGGACACGCACCTTTCC-3' | 31 | cDNA which code TPO-[F46V], TPO-[F128V], TPO-[F131V] and TPO-[F141V] was constructed by primary PCR using specific primers (Table 1) and universal primer T3 and secondary PCR using the primary PCR product and universal primer T7. The template for these reactions was the cDNA coding wild type TPO cloned in pBluescript KS II(+) obtained from Example 1.

The primary PCR was performed by adding 2.5 U Ex taq (Takara, Japan), 5 μl of 10× buffer, 1 mM $MgCl_2$, 2.5 mM dNTP and D.W was added to make the total volume of 50 μl. The PCR condition consisted of 1 cycle at 94° C. for 3 minutes followed by 30 cycles at 95° C. for 30 seconds, at 60° C. for 30 seconds and at 72° C. for 30 seconds and then linked to 1 cycle at 72° C. for 7 minutes. The primary PCR product B. Construction of cDNAs Coding EPO Muteins Four muteins of EPO, EPO-[F48V], EPO-[F138V], EPO-[F142V] and EPO-[F148V] were constructed according to procedures as follows to have a single amino acid-substitution from phenylalanine to valine at each positions, respectively.

TABLE 2

Primers used in constructing cDNAs coding EPO- wild type and muteins

| Primer No. | | | Nucleotide sequence | Sequence No. |
|---|---|---|---|---|
| 11 | Wild EPO | Sense | 5'-GGCGCGGAGATGGGGGT-3' | 32 |
| 12 | | Antisense | 5'-TGGTCATCTGTCCCCTGTCCTG-3' | 33 |
| 13 | EPO-[F48V] | Sense | T3 | |
| 14 | | Antisense | 5'-GACATTAACTTTGGTGTCTGGGAC-3' | 34 |
| 15 | EPO-[F138V] | Sense | 5'-CTGTCCGCAAACTCTTCCGAG-3' | 35 |
| 16 | | Antisense | T7 | |
| 17 | EPO-[F142V] | Sense | 5'-CGGAAACTCGTCCGAGTCTAT-3' | 36 |
| 18 | | Antisense | T7 | |
| 19 | EPO-[F148V] | Sense | 5'-GAGTCTACTCCAATGTGGTGGG-3' | 37 |
| 20 | | Antisense | T7 | |

Construction procedure of cDNA coding EPO muteins was basically similar to that of TPOs. cDNAs which code EPO-[F48V], EPO-[F38V], EPO-[F142V], and EPO-[F148V] were constructed by primary PCR using specific primers (Table 2) and universal primer T3 and secondary PCR using the primary PCR product and universal primer T7. The template for these reactions was the cDNA coding wild type EPO cloned in pBluescript KS II(+) obtained from Example 1.

$Mg^{2+}$ concentration was adjusted to 1 mM in the primary PCR. Sizes of amplified megaprimers were 300 b.p for EPO-[F48V], 550 b.p for EPO-[I38V], 550 b.p for EPO-[F142V] and 550 b.p for EPO-[F148V]. In the secondary PCR using the megaprimers, cDNAs coding the individuals muteins were amplified as the same size of 580 b.p. Substitution from phenylalanine to valine at nucleotide sequence of the individual EPO mutein was verified by direct sequencing.

Each PCR product of 580 b.p was separated in 0.8% agarose gel and was purified with Qiaex II gel extraction kit. The PCR product was digested with 15 U EcoRI and 10 U BamHI at 37° C. for 2 hours. The digested PCR product was ligated into pBluescript KS II(+) as described above and was used for constructing the expression vector. The recombinant expression vector containing DNA which codes TPO-[F141V] was named Refficacin-4 and was deposited at the KCCM (Korean Culture Center of Microorganisms) under the Budapest Treaty on Jun. 9, 2003. Accession number given by international depositary authority was KCCM-10501.

C. Construction of cDNAs Coding G-CSF Muteins

Muteins of G-CSF, G-CSF[F13V], G-CSF[F83V], G-CSF [F113V], G-CSF[F140V], G-CSF[F144V] and G-CSF [F160V] were constructed according to procedures as follows to have a single amino acid-substitution from phenylalanine to valine at each positions, respectively.

TABLE 3

Primers used in constructing cDNAs coding G-CSF- wild type and muteins

| Primer No. | | | Nucleotide sequence | Sequence No. |
|---|---|---|---|---|
| 21 | wild G-CSF | Sense | 5'-CCCCGGGACCATGGCTGGACCTGCCACCCAG-3' | 38 |
| 22 | | Antisense | 5'-CGAATTCGCTCAGGGCTGGGCAAGGAG-3' | 39 |
| 23 | G-CSF-[F13V] | Sense | T7 | |
| 24 | | Antisense | 5'-ACTTGAGCAGGACGCTCT-3' | 40 |
| 25 | G-CSF-[F83V] | Sense | 5'-AGCGGCCTTGTCCTCTA-3' | 41 |
| 26 | | Antisense | T3 | |
| 27 | G-CSF-[F113V] | Sense | 5'-GACGTTGCCACCACCAT-3' | 42 |
| 28 | | Antisense | T3 | |
| 29 | G-CSF-[F140V] | Sense | 5'-GCCGTCGCCTCTGCTTT-3' | 43 |
| 30 | | Antisense | T3 | |
| 31 | G-CSF-[F144V] | Sense | 5'-TCGCCTTCTGCTGTCCAG-3' | 44 |
| 32 | | Antisense | T3 | |
| 33 | G-CSF-[F160V] | Sense | 5'-TCTGCAAGACGTCCTGG-3' | 45 |
| 34 | | Antisense | T3 | |

Construction procedure of cDNA coding G-CSF muteins was basically similar to that of TPOs. cDNAs which code G-CSF-[F13V], G-CSF-[F83V], G-CSF-[F113V], G-CSF-[F140V], G-CSF-[F144V], and G-CSF-[F160V] were constructed by primary PCR using specific primers (Table 3) and universal primer T3 and secondary PCR using the primary PCR product and universal primer 17. The template for these reactions was the cDNA coding wild type G-CSF cloned in pBluescript KS II(+) obtained from the Example 1.

Mg$^{2+}$ concentration was adjusted to 1 mM in the primary PCR. Sizes of amplified megaprimers were 600 b.p for G-CSF-[F13V], 390 b.p for G-CSF-[F83V], 300 b.p for G-CSF-[F113V], 200 b.p for G-CSF-[F140V], 200 b.p for G-CSF-[F144V], and 150 b.p for G-CSF[F160V]. In the secondary PCR using the megaprimers, cDNAs coding each muteins were amplified as the same size of 640 b.p. Substitution from phenylalanine to valine at nucleotide sequence of the individual G-CSF mutein was verified by direct sequencing.

Each PCR product of 640 b.p was separated in 0.8% agarose gel and purified with Qiaex II gel extraction kit The PCR product was digested with 15 U SmaI and 10 U EcoRI at 37° C. for 2 hours and separated in 0.8% agarose gel and purified with Qiaex II gel extraction kit The digested PCR product was ligated into pBluescript KS II(+) as described above. The recombinant expression vector containing DNA which codes G-CSF-[F140V] was named Grefficacin4 and was deposited at the KCCM (Korean Culture Center of Microorganisms) under the Budapest Treaty on May 17, 2004. Accession number given by international depositary authority was KCCM-10571.

D. Construction of cDNAs Coding GH Muteins

Four muteins of GH, GH-[F44V], GH-[F97V], GH-[F139V], GH-[F146V], GH-[F166V], and GH-[F176V] were constructed according to procedures as follows to have a single amino acid-substitution from phenylalanine to valine at each positions, respectively.

Mg$^{2+}$ concentration was adjusted to 1 mM in the primary PCR. Sizes of each amplified megaprimers were 130 b.p for GH-[F44V], 300 b.p for GH-[F97V], 420 b.p for GH-[F139V], 450 b.p for GH-[F146V], 500 b.p for GH-[F166V] and 530 b.p for GH-[F176V] PCRs. Substitution from phenylalanine to valine at nucleotide sequence of the individual GH mutein was verified by direct sequencing.

Each PCR product of 650 b.p was separated in 0.8% agarose gel and purified with Qiaex II gel extraction kit. The PCR product was digested with 15 U EcoRI and 10 U HindIII at 37° C. for 2 hours and separated in 0.8% agarose gel and purified with Qiaex II gel extraction kit The digested PCR product was ligated into pBluescript KS II(+) as described above.

EXAMPLE 3

Expression and Purification of TPO Muteins

A. TPO Muteins a. Establishments of Transfected Cell Lines by Using Lipofection Method Chinese hamster ovary ("CHO-K1")(ATCC, CCL61) cells were prepared at a density 1.5×10$^5$ cells per 35 mm dish containing Dulbecco's modified Eagle's medium ("DMEM")[Gibco BRL, USA] supplemented with 10% fetal bovine serum ("FBS"). The cells were grown at 37° C. in a 5% CO$_2$ for 18-24 hrs. 6 μl of Lipofectamine was added to 1.5 μg

TABLE 4

Primers used in constructing cDNAs coding GH- wild type and muteins

| Primer No. | | Nucleotide Sequeuce | Sequence No. |
|---|---|---|---|
| 35 | Leader sequence | Sense-1 5'-CTTTTGGCCTGCTCTGCCTGTCCTGGCTTCAA GAGGGCAGTGCCTTCCCAACCATTCCCTTATC-3' | 46 |
| 36 | addition | Antisense T3 | |
| 37 | | Sense-2 5'-GGAATTCATGGCTGCAGGCTCCCGGACGTCC CTGCTCCTGGCTTTTGGCCTGCTCTGCCT-3' | 47 |
| 38 | | Antisense T3 | |
| 39 | GH- | Sense T7 | |
| 40 | [F44V] | Antisense 5'-GGGGTTCTGCAGGACTGAATACTTC-3' | 48 |
| 41 | GH- | Sense T7 | |
| 42 | [F97V] | Antisense 5'-GGCTGTTGGCGACGATCCTG-3' | 49 |
| 43 | GH- | Sense T7 | |
| 44 | [F139V] | Antisense 5'-GTAGGTCTGCTTGACGATCTGCCCAG-3' | 50 |
| 45 | GH- | Sense T7 | |
| 46 | [F146V] | Antisense 5'-GAGTTTGTGTCGACCTTGCTGTAG-3' | 51 |
| 47 | GH- | Sense T7 | |
| 48 | [F166V] | Antisense 5'-GTCCTTCCTGACGCAGTAGAGCAG-3' | 52 |
| 49 | GH- | Sense T7 | |
| 50 | [F176V] | Antisense 5'-CGATGCGCAGGACTGTCTCGACCTTGTC-3' | 53 |

Construction procedure of cDNA coding GH muteins was basically similar to that of TPOs. cDNAs which code muteins GH-[F44V], GH-[F97V], GH-[F139V], GH-[F146V], GH-[F166V] and GH-[F176V] were constructed by primary PCR using specific primers (Table 4) and universal primer T3 and secondary PCR using the primary PCR product and universal primer T7. The template for these reactions was the cDNA coding wild type GH cloned in pBluescript KS II(+) obtained from Example 1.

of the recombinant expression vector comprising DNA coding TPO mutein in a sterile tube. Volume of his mixture was adjusted to 100 μl by adding serum-free DMEM. The tube was incubated at room temperature for 45 min. The cells grown in 35 mm dish were washed twice with serum-free DMEM and 800 μl of serum-free DMEM was added to the dish. The washed cells were gently overlaid on the lipofectamine-DNA complex and then incubated for 5 hrs at 37° C. in 5% CO$_2$. After 5 hrs incubation, 1 ml of DMEM containing 20% FBS was added to transfected cells and then the cells were incubated for 18-24 hrs at 37° C., 5% $CO_2$. After the incubation, the cells were washed twice with serum-free DM and then 2 ml of DMEM containing 10% FBS was added to the culture. These cells were incubated for 72 hrs at 37° C., 5% $CO_2$.

b. Analysis of Expression Level of TPO Muteins Using ELISA

The cells transfected with plasmid containing cDNA coding TPO-wild type or muteins were analyzed on their protein expression level by using ELISA assay. An goat anti-human TPO polyclonal antibody (R&D, U.S.A) diluted to 10 μg/ml with coating buffer [0.1M Sodium bicarbonate, (pH 9.6)] was added into each wells of 96 well plate (Falcon, USA) up to 100 μl per well and incubated for 1 hour at room temperature. The plate was washed with 0.1% Tween-20 in 1×PBS (PBS three times. After washing, the plate was incubated with 200 μl of blocking buffer (1% FBS, 5% sucrose, 0.05% sodium azide) for 1 hour at room temperature and then washed three times with PBST. The cultured supernatants (including the transfected cells) and dilution buffer[0.1% BSA, 0.05% Tween-20, 1×PBS] were mixed with serial dilutions. 25 ng/ml of recombinant human TPO [CALBIOCHEM, USA] as a positive control and untransfected CHO-K1 cultured supernatants as a negative control were equally diluted. These controls and samples were incubated for 1 hr at room temperature. Then, the plate was washed with PBST three times. A biotinylated goat anti-human TPO antibody (R&D, USA) diluted to 0.2 μg/ml with dilution buffer was added to the 96 well plate up to 100 μl per well and incubated for 1 hr at room temperature. The plate was washed with PBST three times. Streptavidin-HRP (R&D, USA) diluted to 1:200 in dilution buffer was added 100 μl per well to the 96 well plate and incubated for 1 hr at room temperature. After 1 hour, the plates was washed three times with PBST, and then coloring reaction was performed by using TMB microwell peroxidase substrate system (KPL, USA) and OD was read at 630 nm with microplate reader[BIO-RAD, Model 550].

c. Analysis of Expression Level and Molecular Weight of Mutein TPO Using Western Blotting In order to exclude FBS in medium, CHO-S-SFM II (Gibco BRL, USA) was used for culture of the above-transfected cell. Culture medium from CHO-S-SFM II was filtrated with 0.2 μm syringe filter and concentrated with centricon (Mol. 30,000 Millipore, USA). To perform the reduced SDS-PAGE, sample-loading buffer containing 5% β-mercaptoethanol was added to the sample and heated for 5 minutes. Stacking gel and running gel were used for this SDS-PAGE. The stacking gel was composed of 3.5% acrylamide, 0.375 M Tris (pH6.8), 0.4% SDS and the running gel was composed of 10% acrylamide gel, 1.5 M Tris (pH8.8), 0.4% SDS. After SDS-PAGE gel running treatment, protein samples were transferred to Westran (PVDF transfermembrane, S&S) having 4 μm pore at 350 mA for 2 hrs in a 25 mM Tris-192 mM glycine (pH 8.3) –20% methanol buffer-containing reservoir. After transferring, it was blocked three times for 10 minutes with 5% fat free milk powder in PBST. The biotinylated goat anti-human TPO antibody (R&D, USA) was diluted to 0.25 μg/ml in blocking buffer and 3 ml of this solution was added and shaken for 6 hrs. The membrane was washed with washing solution three times. Streptavidin-HRP (R&D, USA) was diluted to 1:100 in blocking buffer and incubated for 1 hr. The membrane was washed three times with washing solution. Protein bands were visualized by incubating with DAB substrate (VECTOR LABORATORIES, USA) for 10 minutes. This reaction was stopped with soaking the membrane in deionized water.

Figure 2A:
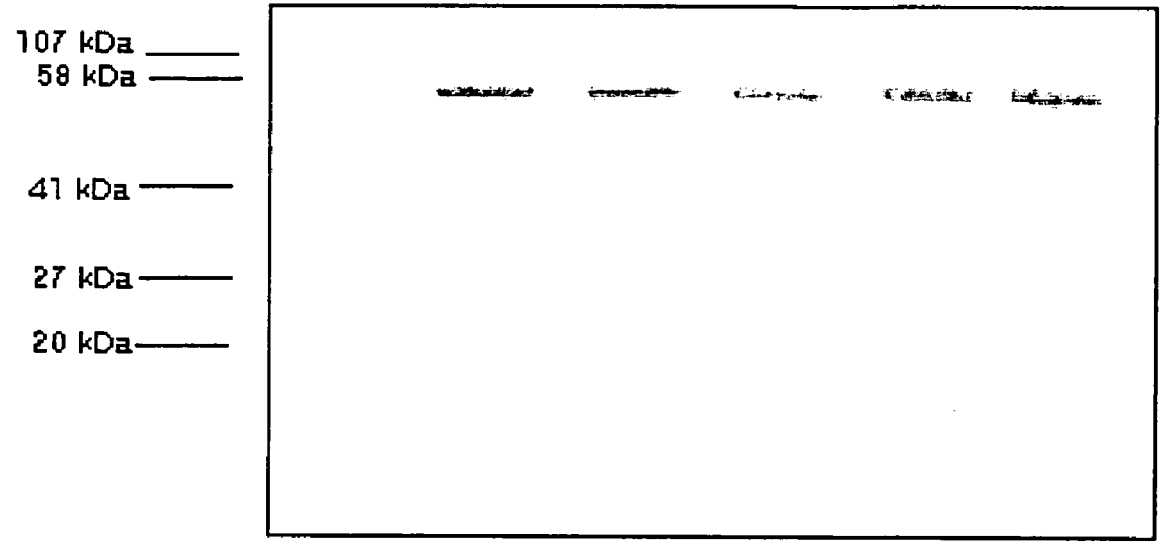

In FIG. 2a, wild type and mutein forms of TPOs had the same molecular weight (55 kD).

Figure 3A:
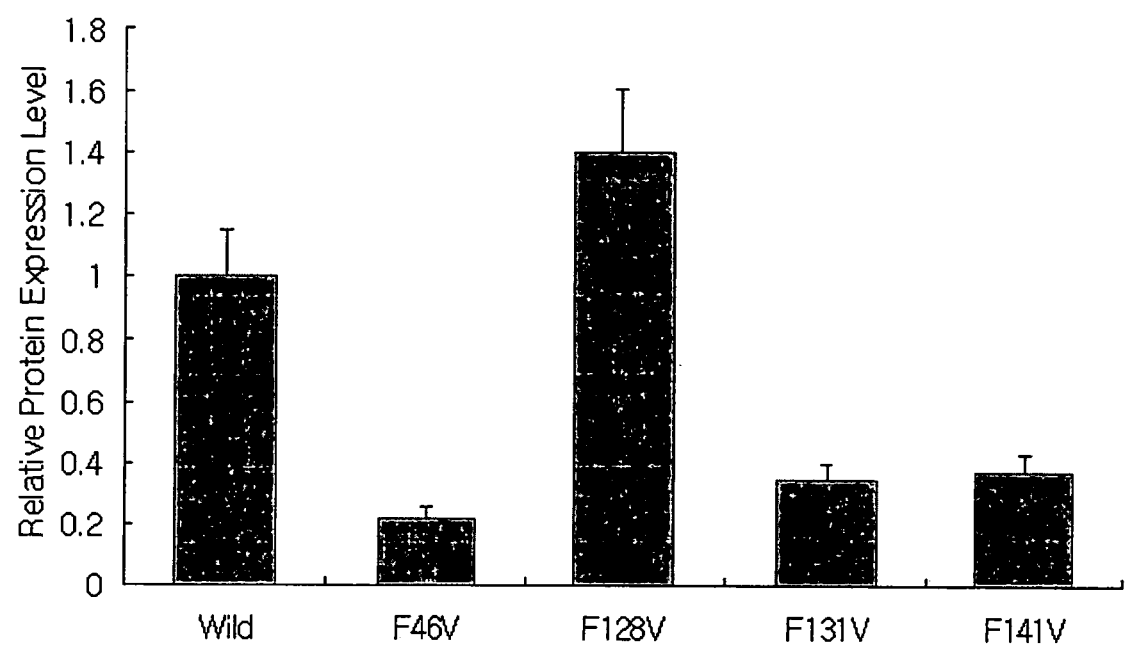
FIG. 3A is a graph showing the relative expression levels of TPO variants according to the present invention, compared to a wild-type TPO.

Relative expression level of wild type and muteins of TPO was shown in FIG. 3a Expression level of each TPO mutein was compared to that of wild type TPO as a control. Expression level of TPO-[F128V] was increased 1.4 times more than that of wild type TPO. But expressions of TPO-[F46V], -[F131V] and -[F141V] were decreased to 20%, 40%, and 40% of wild type, respectively.

B. EPO Muteins

Expression vectors containing cDNAs coding EPO muteins were transfected to CHO-K1 cell and expression level of each of EPO mutein was detected by using ELISA assay. And molecular weight of each of wild type and mutein of EPO was analyzed by western blotting.

Figure 2B:
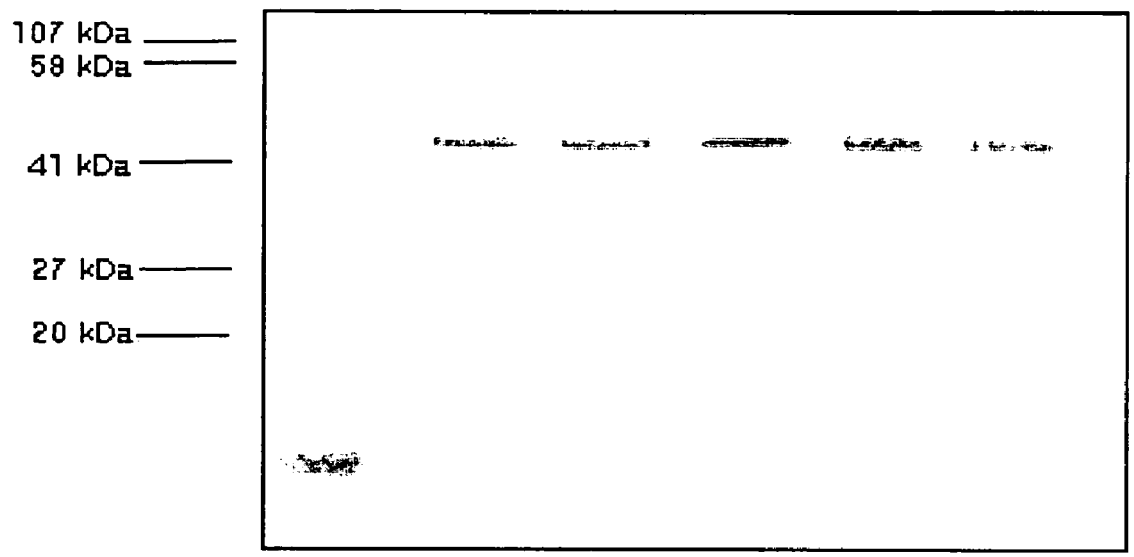

In FIG. 2b, wild type and mutein forms of EPO had the same molecular weight (45 kD).

Figure 3B:
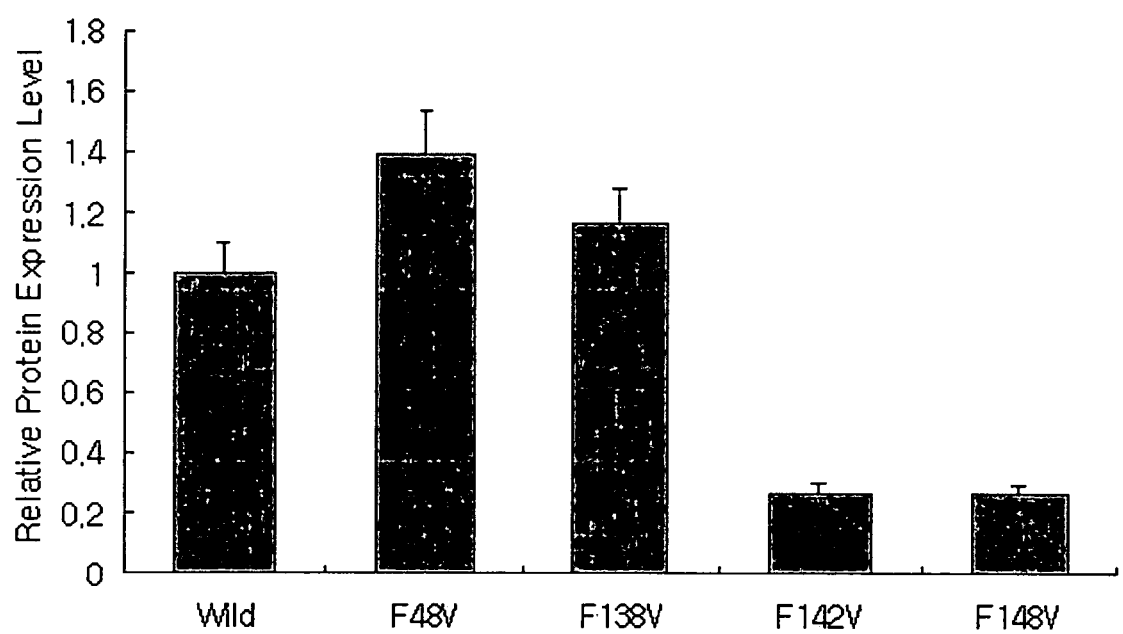
FIG. 3B is a graph showing the relative expression levels of EPO variants according to the present invention, compared to a wild-type EPO.

Relative expression level of wild type and muteins of EPO was shown in FIG. 3b. Expressions level of EPO-[F48V] and -[F138V] was increased 1.4 and 1.2 times more than that of the wild type EPO, respectively. But expression level of EPO-[F142V] and -[F148V] was decreased to 20% and 30% of that of wild type EPO, respectively.

C. G-CSF Muteins

Expression vectors containing cDNAs coding G-CSF muteins were transfected to CHO-K1 cell and expression level of each G-CSF mutein was detected by using ELISA assay. And molecular weight of each of wild type and muteins of G-CSF was analyzed by western blotting.

Figure 2C:
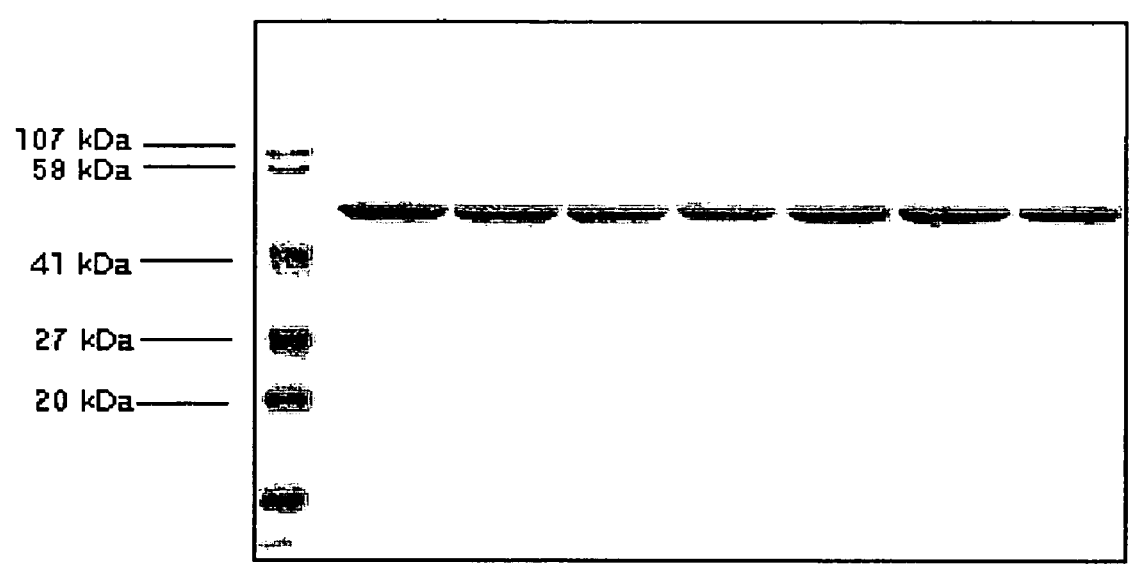

In FIG. 2c, wild type and mutein forms of G-CSF had the same molecular weight (50 kD).

Figure 3C:
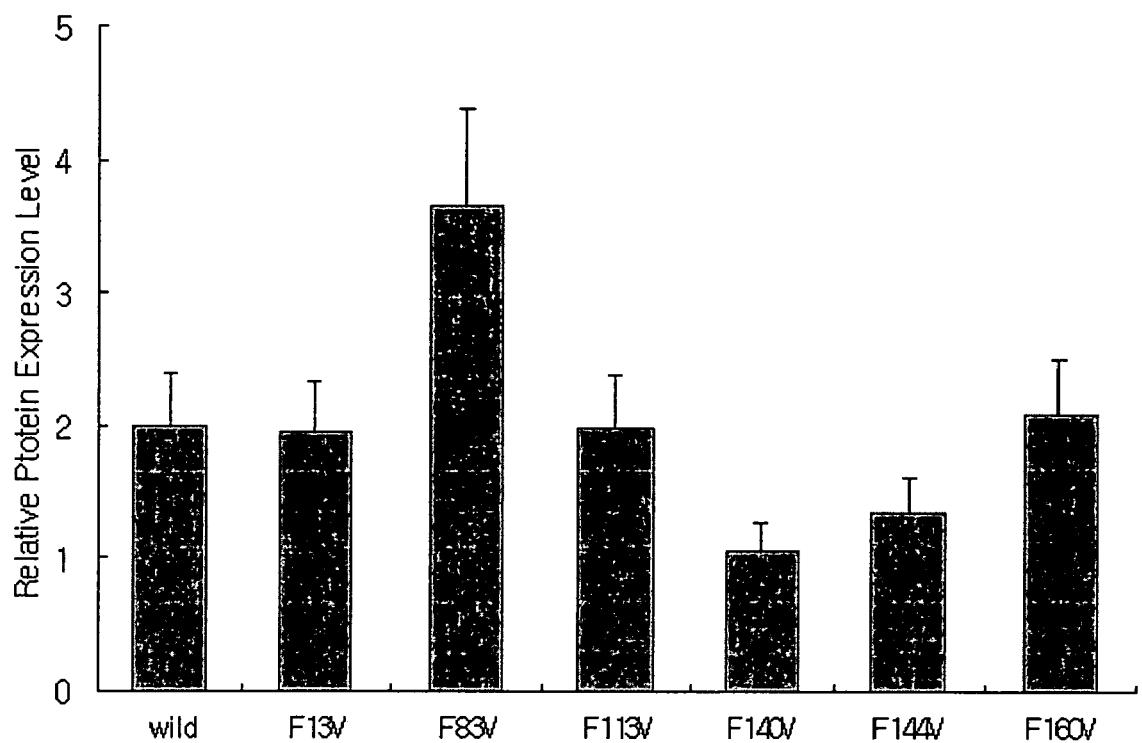
FIG. 3C is a graph showing the relative expression levels of G-CSF variants according to the present invention, compared to a wild-type G-CSF.

Relative expression level of wild type- and muteins of G-CSF was shown in FIG. 3c. Expression levels of rest of G-CSF muteins were similar to that of wild type G-CSF. Expression level of G-CSF mutein-[F83V] was increased 1.9 times than that of wild-type. But expression levels of G-CSF muteins-[F140V] and -[F144V] were decreased to 50% and 70% of that of wild type G-CSF, respectively.

D. GH Muteins

Expression vectors containing cDNAs coding GH muteins were transfected to CHO-K1 cell. Method for the expression of each of the GH muteins was the same as those used for TPO production.

EXAMPLE 4

Construction of DNA Coding EPO, TPO, G-CSF, and GH Receptors

A. Construction of DNA Coding EPO and TPO Receptors

DNAs coding EPO and TPO receptors were constructed to analyze binding affinities of each of EPO muteins and TPO muteins. DNA coding extracellular domain of each receptor was linked to DNA coding Fc domain of IgG1 such that the C-terminal region of extracellular domain of each receptor was used to N-terminal region of human IgG1 Fc domain. cDNA coding EPO receptor was constructed by PCR using sense primer (primer 51) with restriction sites of EcoRI and leader sequence of EPO receptor and antisense primer (primer 52) with the sequence coding 3' end of EPO receptor and the sequence coding 5'end Fc domain of IgG. cDNA coding TPO receptor linked to Fc domain of IgG1 was constructed by PCR using sense primer (primer 53) with restriction sites of HindIII and leader sequence of TPO receptor and antisense primer (primer 54) with the sequence coding 3' end of TPO receptor and the sequence coding 5'end of Fc domain of IgG.

cDNA coding EPO receptor produced as described above and DNA coding Fc domain of IgG1 were mixed in the same tube, complementary binding between the common sequences was induced. Using this mixture, cDNA coding EPO receptor linked to Fc domain of IgG1 was constructed by PCR using sense primer (primer 51) with restriction sites of EcoRI and leader sequence of EPO receptor and antisense primer (primer 55) with restriction sites of XbaI and 3'end of Fc domain of IgG. The PCR product was cut with EcoRI and XbaI and inserted into PCR-3 expression vector for production of EPO receptor-Fc fusion protein cDNA coding TPO receptor produced as described above and DNA coding Fc domain of IgG1 were mixed in the same tube, thus complementary binding between the common sequences was induced. Using this mixture, cDNA coding TPO receptor linked to Fc domain of IgG1 was constructed by PCR using sense primer (primer 53) with restriction sites of EcoRI and leader sequence of EPO receptor and antisense primer (primer 55) with restriction sites of XbaI and 3'end of Fc domain of IgG. The PCR product was cut with HindIII and XbaI and inserted into PCR-3 expression vector for production of TPO receptor-Fc fusion protein.

The PCR product encoding G-CSF receptor was digested with HindIII and EcoRI, and was cloned by inserting into a commercially available cloning vector, pBluescript KS II(+) at HindIII/EcoRI site. The PCR product encoding GH receptor was digested with EcoRI and SpeI, and cloned by inserting into a commercially available cloning vector, pBluescript KS II(+) at EcoRI/SpeI site.

Fc domain of human IgG was constructed by PCR using sense primer (primer 60 for G-CSF, primer 61 for GH) with sequence coding 5' end part of hinge region of human IgG and antisense primer (primer 62). For G-CSF receptor, the PCR product coding Fc domain of human IgG was digested with EcoRI and XbaI and cloned by inserting into a commercially available cloning vector, pBluescript KS II(+) at EcoRI/XbaI site. For GH receptor, the PCR product coding Fc domain of human IgG was digested with SpeI and XbaI, and cloned by inserting into a commercially available cloning vector, pBluescript KS II(+) at SpeI site/XbaI.

Both of the cloned cDNA coding G-CSF receptor and the cloned Fc domain of human IgG were digested with EcoRI/

TABLE 5

A List of primers used in constructing TPO and EPO receptors fused to immunoglobulin

| | Primer No. | | Nucleotide sequence | Sequence No. |
|---|---|---|---|---|
| EPO receptor | 51 | Sense | 5'-CGGAATTCATGGACCACCTCGGGGCG-3' | 54 |
| | 52 | Antisense | 5'-GCTCTAGACTAAGAGCAAGCCACATAGCTGGG-3' | 55 |
| TPO receptor | 53 | Sense | 5'-CCCAAGCTTATGGAGCTGACTGAATTGCTCCTC-3' | 56 |
| | 54 | Antisense | 5'-GGAATTCTTACCCTTCCTGAGACAGATTCTGG-3' | 57 |
| IgG1-R-XbaI | 55 | | 5'-GCTCTAGAGCTCATTTACCCGGAGACAGGGAGAG-3' | 58 |

B. Construction of DNA Coding G-CSF and GH Receptors cDNA coding G-CSF receptor was constructed by PCR using sense primer (primer 56) with restriction site of HindIII and leader sequence of G-CSF receptor and antisense primer (primer 57) with restriction site of EcoRI and the sequence coding 3' end of G-CSF receptor. cDNA coding GH receptor was constructed by PCR using sense primer (primer 58) with restriction site of EcoRI and leader sequence of G-CSF receptor and antisense primer (primer 59) with restriction site of SpeI and the sequence coding 3' end of G-CSF receptor.

XbaI and then ligated to prepare DNA coding G-CSF receptor linked to Fc domain of human IgG. This DNA construct was cut with HindIII and XbaI and inserted into PCR-3 expression vector. Both of the cloned cDNA coding GH receptor and the cloned Fc domain of human IgG were digested with SpeI/XbaI and then ligated to prepare DNA coding G-CSF receptor linked to Fc domain of human IgG. This DNA construct was cut with EcoRI and XbaI and inserted into PCR-3 expression vector.

TABLE 6

A List of primers used in constructing G-CSF and GH receptors fused to Immunoglobulin

| | Primer No. | | Nucleotide sequence | Sequence No. |
|---|---|---|---|---|
| G-CSF receptor | 56 | Sense | 5'-CCCAAGCTTATGGCTGGACCTGCCACCC-3' | 59 |
| | 57 | Antisense | 5'-GGAATTCGCAACAGAGCCAGGCAGTTCCA-3' | 60 |
| GH receptor | 58 | Sense | 5'-CGGAATTCATGGATCTCTGGCAGCTG-3' | 61 |
| | 59 | Antisense | 5'-GGACTAGTTTGGCTCATCTGAGGAAGTG-3' | 62 |
| IgG1-F-EcoRI | 60 | Sense | 5'-GGAATTCGCAGAGCCCAAATCTTGTGACAAAACTC-3' | 63 |

TABLE 6-continued

A List of primers used in constructing
G-CSF and GH receptors fused to Immunoglobulin

| Primer No. | | | Nucleotide sequence | Sequence No. |
|---|---|---|---|---|
| IgG1-F-SpeI | 61 | Sense | 5'-GACTAGTGCAGAGCCCAAATCTTGTGA-3' | 64 |
| IgG1-R-XbaI | 62 | Antisense | 5'-GCTCTAGAGCTCATTTACCCGGAGACAGGGAGAG-3' | 65 |

EXAMPLE 5

Measurement of Binding Affinity of Cytokines and Their Muteins to Each of Their Receptors by Using ELISA A. Binding of TPO and TPO Muteins to TPO Receptor Culture supernatants of CHO cell transfected with expression vectors carrying genes for TPO muteins were used for measuring cytokine-receptor interactions.

TPO receptor-Ig fusion protein was purified from culture supernatant of CHO cell transfected with recombinant expression vector carrying gene coding for TPO receptor-Fc fusion protein by using Protein A Sepharose-4B column (PHARMACIA, Sweden). The purified fusion protein diluted to 10 μg/ml with coating buffer [0.1M Sodium bicarbonate, (pH 9.6)] was added into each wells of 96 well plate (Falcon, USA) up to 100 μl per well and incubated for 1 hour at room temperature. The plate was washed with 0.1% Tween-20 in 1×PBS [PBST] three times. After washing, the plate was incubated with 200 μl of blocking buffer (1% FBS, 5% sucrose, 0.05% sodium azide) for 1 hour at room temperature and then washed three times with PBST.

After washing, culture supernatants consisting of four TPO muteins and one TPO wild type, respectively were diluted serially with dilution buffer [0.1% BSA, 0.05% Tween-20, 1×PBS] and was added to 96 well plate coated with the IPO receptor-Fc fusion protein and incubated for 1 hr. The washing was repeated three times with PBST. A recombinant human TPO [CALBIOCHEM, USA] as a positive control and untransfected CHO-K1cultured supernatants as a negative control were equally diluted. The plates were washed with PBST three times. A biotinylated goat anti-human IPO antibody (R&D, USA) diluted to 0.2 μg/ml in dilution buffer was added to the 96 well plate to 100 μl per well and incubated for 1 hr at room temperature. The plate was washed with PBST three tunes. Streptavidin-HRP (R&D, USA) diluted to 1:200 in dilution buffer was added 100 μl per well to 96 well plate and incubated for 1 hr at room temperature. The plate was washed three times with PBST after 1 hour. Coloring reaction was performed using TMB microwell peroxidase substrate system (KPL, USA) and O.D was read at 630 nm with microplate reader [BIG-RAD, Model 550].

Figure 4A:
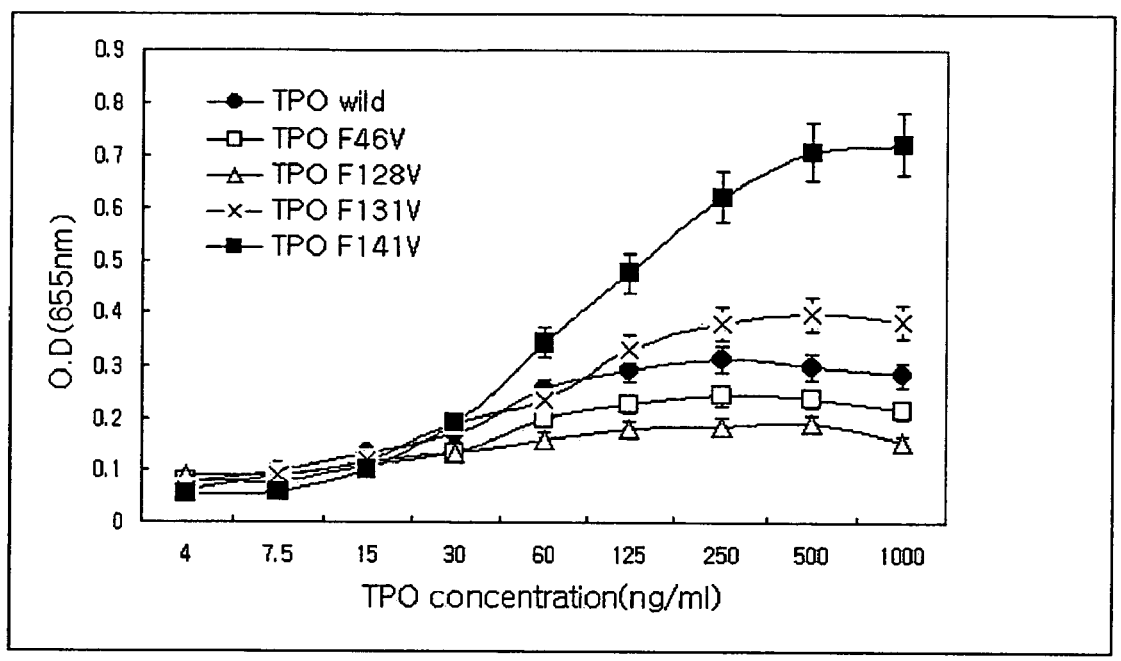
FIG. 4A shows the results of an ELISA assay for binding affinity of TPO variants according to the present invention to TPO receptors.

The binding affinity of TPO-[F141V] and TPO-[F131V] to the TPO receptor was increased compared to that of wild type TPO (FIG. 4a). And the former mutein had the strongest binding affinity among all TPO muteins.

B. Binding of EPO and EPO Muteins to EPO Receptor

Measurement of binding affinity of EPO wild type and Muteins to the receptor was basically similar to that of binding affinity of TPO and TPO muteins to TPO Receptor.

Figure 4B:
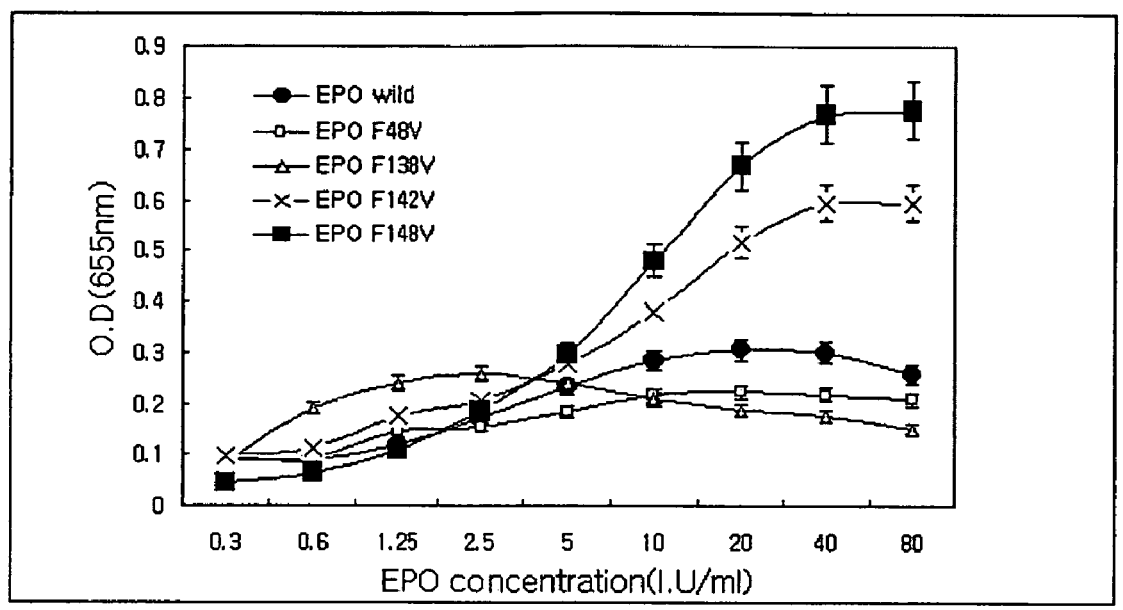
FIG. 4B shows the results of an ELISA assay for binding affinity of EPO variants according to the present invention to EPO receptors.

The binding affinity of EPO-[F148V] and EPO-[F142V] to the EPO receptor was increased compared to that of wild type EPO (FIG. 4b). And the former mutein had the strongest binding affinity among all EPO muteins.

C. Binding of G-CSF and G-CSF Muteins to G-CSF Receptor

Measurement of binding affinity of G-CSF wild type and muteins to the receptor was basically similar to that of binding affinity of TPO and TPO muteins to TPO Receptor.

Figure 4C:
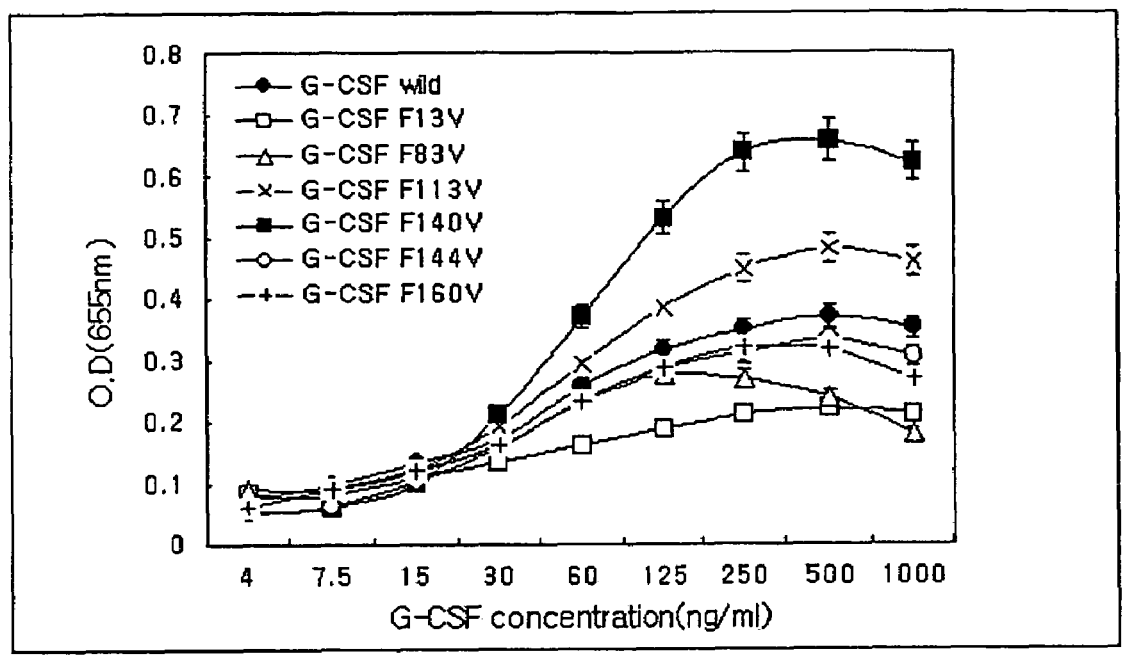
FIG. 4C shows the results of an ELISA assay for binding affinity of G-CSF variants according to the present invention to G-CSF receptors.

Results (FIG. 4c) showed binding affinity of G-CSF-[F140V], G-CSF-[F144V], and G-CSF-[F160V] to the G-CSF receptor was increased compared to that of wild type G-CSF. And the first mutein (G-CSF-[F140V]) had the strongest binding affinity among all G-CSF muteins.

D. Binding of GH and GH Muteins to GH Receptor

Measurement of binding affinity of GH wild type and muteins to the receptor was basically similar to that of binding affinity of TPO and TPO muteins to TPO Receptor.

Figure 4D:
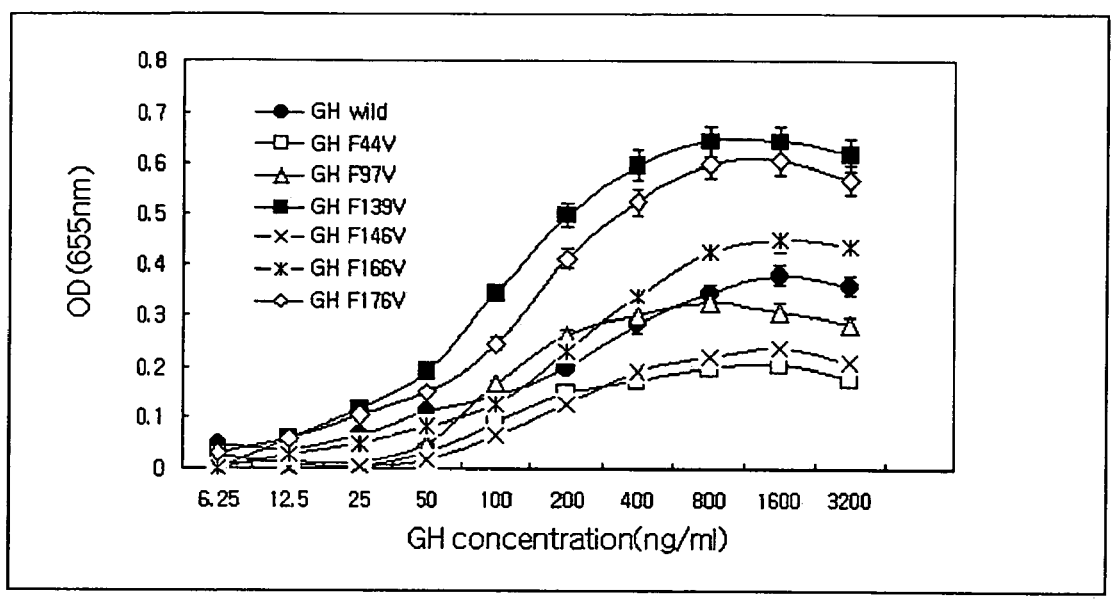
FIG. 4D shows the results of an ELISA assay for binding affinity of GH variants according to the present invention to GH receptors.

Results (FIG. 4d) showed that GH-[F139V] had the strongest binding affinity to the GH receptor.

EXAMPLE 6

Measurement of Bindings of Cytokines and Their Muteins to Each of Their Receptors by Using SPR A. Binding of TPO and TPO Muteins to TPO Receptor To measure the binding affinity of TPO-[F141V] and TPO-[F131V] to TPO receptor, SPR was performed on a BIAcore 3000 instrument containing CM5 sensor chip. Anti-human IgG antibody was immobilized onto each flow cells 1 and 2 using amine-coupling chemistry. To inactivate any active group, surfaces were blocked with 1 M ethanolamine. TPO receptor-Fc fusion protein was added to bind to the anti-human IgG antibody for 2 min at 30 μl/min and then TPO and TPO muteins were reacted to bind to the TPO receptor.

Figure 5A:
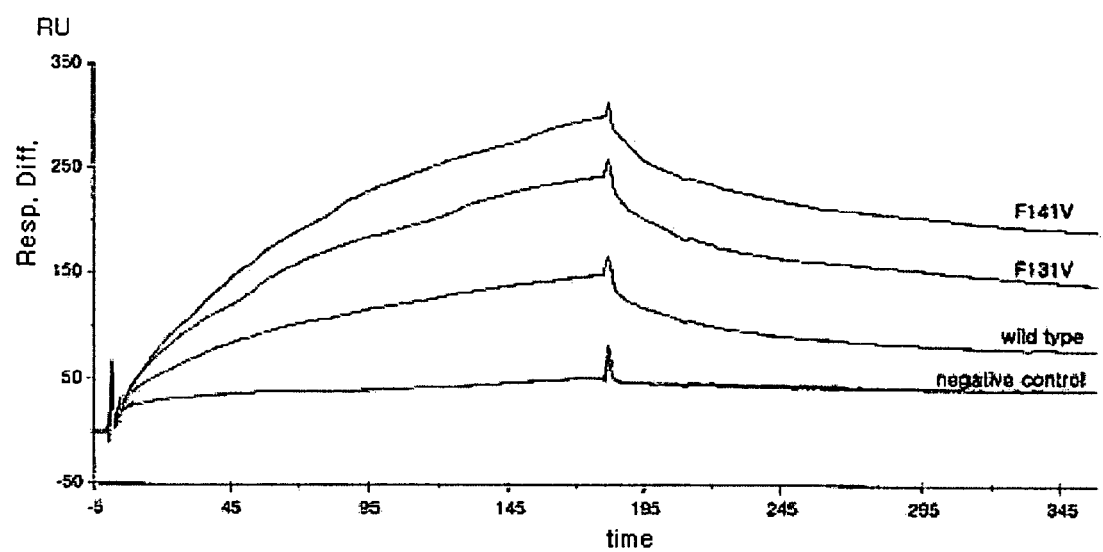
FIG. 5A shows the results of an SPR assay for binding affinity of TPO variants according to the present invention to TPO receptors.

At the same density of ligand, increased resonance unit (RU) means higher binding affinities. In FIG. 5a, wild TPO, TPO-[F141V] and TPO-[F131V] were 10RU, 30RU and 20RU, respectively. This result showed that TPO-[F141V] had the strongest binding affinity. In addition, $K_D$ values of wild type and mutein TPO were shown in Table 7.

TABLE 7

Changes of Binding-kinetic rate constant of wild type and mutein TPO

|  | $K_{on}(M^{-1}s^{-1}) \times 10^5$ | $K_{off}(S^{-1}) \times 10^{-2}$ | $K_D(\mu M) = K_{off}/K_{on}$ | $Chi^2$ | Relative Binding affinity |
|---|---|---|---|---|---|
| Wild type TPO | 2.42 | 13.7 | 5.66 | 5.81 | 1 |
| TPO-[F141] | 12.8 | 0.51 | 0.04 | 6.03 | 141 |

B. EPO Muteins

SPR was performed to measure binding affinities of EPO mutein-[F148V] and EPO-[F142V] with EPO receptor. Experimental procedure was similar to that for TPOs.

Figure 5B:
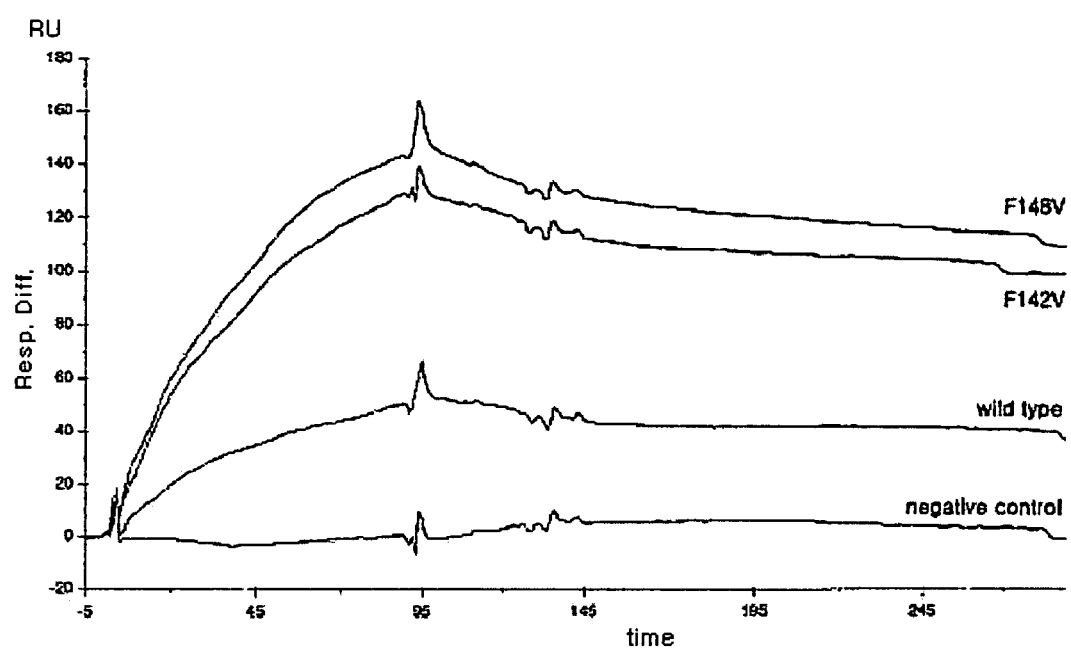
FIG. 5B shows the results of an SPR assay for binding affinity of EPO variants according to the present invention to EPO receptors.

FIG. 5b was the SPR result of EPO wild type and muteins. In FIG. 5b, EPO-[F148V] showed 40RU, EPO-[F142V] 30RU. These results show that EPO-[F148V] had the strongest binding affinity. In addition, $K_D$ values of EPO muteins were shown in Table 8.

TABLE 8

Changes of Binding-kinetic rate constant of wild type and mutein EPO

|  | $K_{on}(M^{-1}s^{-1}) \times 10^5$ | $K_{off}(S^{-1}) \times 10^{-2}$ | $K_D(\mu M) = K_{off}/K_{on}$ | $Chi^2$ | Relative Binding affinity |
|---|---|---|---|---|---|
| Wild type EPO | 1.84 | 8.83 | 4.80 | 4.55 | 1 |
| EPO-[F148] | 14.0 | 0.64 | 0.05 | 2.26 | 105 |

EXAMPLE 7

Measurement of Binding Affinities of Wild Type and Muteins of Cytokine by Using FACS A. Establishment of TF-1/c-Mpl Cell Line TF-1/c-Mpl cell line was established by transfecting cDNA coding c-Mpl into TF-1 cell. Expression of c-Mpl was verified by using FACS analysis. The $1 \times 10^6$/ml of the TF-1/c-Mpl cells was washed with PBS buffer and purified c-Mpl mouse anti-human monoclonal antibody (BD PharMingen, USA) was incubated with the TF-1/c-Mpl cells. And then FTC-conjugated anti-mouse IgG (whole molecule; SIGMA, USA) was added to verify expression of c-Mpl on surface of the TF-1/c-Mpl cells. As a result, graph of the TF-1/c-Mpl cell was shifted rightward from that of TF-1 cells. This result showed that c-Mpl, TPO receptor, was expressed on the TF-1/c-Mpl cell.

B. FACS Analysis of TPO Muteins

The $1 \times 10^6$/ml of TF-1/c-Mpl cell was suspended in PBS buffer and TPO wild type and -[F141V] was added to the suspension and incubated at 4° C. for 30-60 minutes, respectively. Biotinylated goat anti-human IPO polyclonal antibody (R&D, USA) was added to the cells above and incubated at 4° C. for 30-60 minutes. Streptavidin-FITC (SIGMA, USA) was added to the cells above and incubated at 4° C. for 30-60 minutes. The cells were washed twice with PBS buffer to remove non-reacted Streptavidin-FITC. The cells were suspended in PBS buffer and flow cytometric analysis was performed at 488 nm using EXCALIBUR (BD, U.S.A).

Figure 6A:
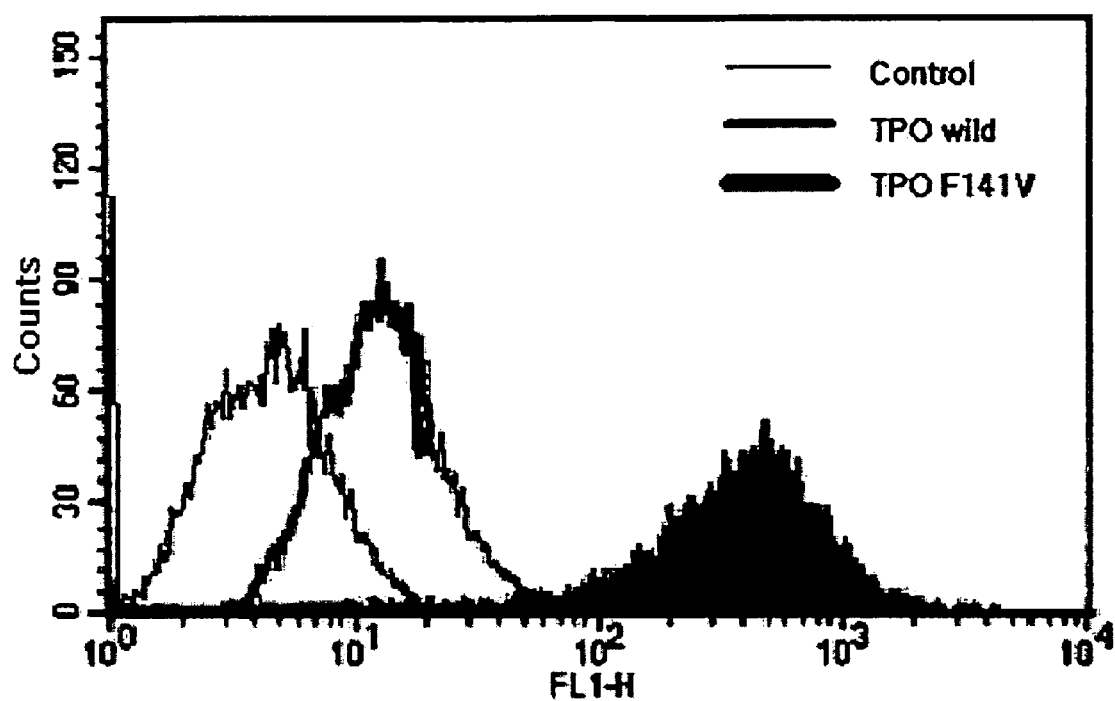
FIG. 6A shows the results of a FACS analysis for binding affinity of a TPO variant according to the present invention to TPO receptors.

In FIG. 6a, a binding curve of TPO-[F141V] was shifted rightward from that of wild type TPO. This result showed that TPO-[F141V] had much stronger receptor-binding affinity than the wild type TPO.

C. FACS Analysis of EPO Muteins

FACS procedure of EPO muteins was carried out similarly to that of TPO.

Figure 6B:
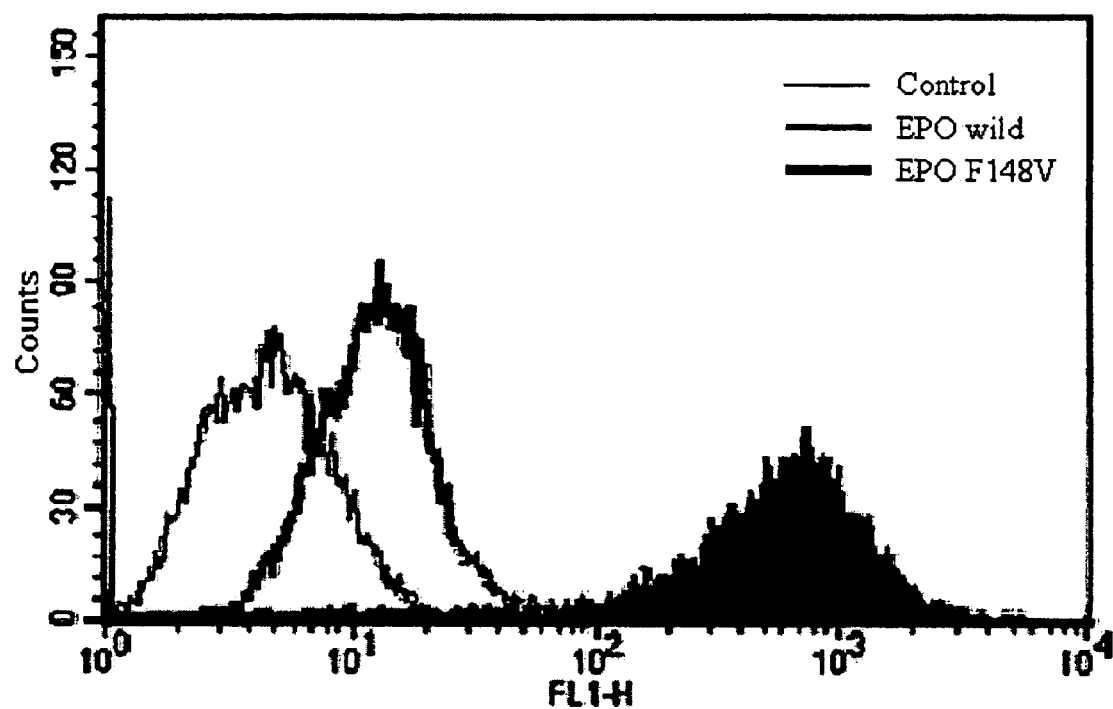
FIG. 6B shows the results of a FACS analysis for binding affinity of an EPO variant according to the present invention to EPO receptors.

In FIG. 6b, a binding curve of EPO-[F148V] was shifted rightward from that of wild type TPO. This result showed that TPO-[F141V] is much stronger in receptor-binding affinity than the wild type EPO.

EXAMPLE 8

Measurement of Biological Activities of TPO, EPO, G-CSF and GH Muteins

A. Cell Proliferation Assay of TPO Muteins

To investigate differences of cell proliferation and biological activities between TPO-wild type and muteins, TF-1/c-Mpl cell line produced above was used. TF-1c-Mpl cells were grown m DMEM medium supplemented with 10% fetal bovine serm, 1 ng/ml GM-CSF at 37° C., 5% $CO_2$. 0.4, 1,5, 10, 20, 40, 75 ng/ml of each of TPO-wild type and muteins in RPMI-1640 were seeded in 96-well tissue-culture plates (FALCON, USA). $1 \times 10^4$ cell of the TF-1c-Mpl cells in RPMI-1640 containing 10% fetal bovine serum was added to each wells of the 96-well plate. After 4 days cultivation at 37° C., 5% $CO_2$, 20 μl of MTS solution [3-(4,5-dimethyl-2-yl)-5-(3-arboxymethoxyphenyl)-2-(4-sulf-ophenyl)-2H-tetrazolium, inner salt, MTS] and the phenazine ethosulfate (PES; PROMEGA) was added and incubated for 4 hours. O.D. was measured with microplate reader (BIO-RAD Model 550) at 490 nm.

Figure 7A:
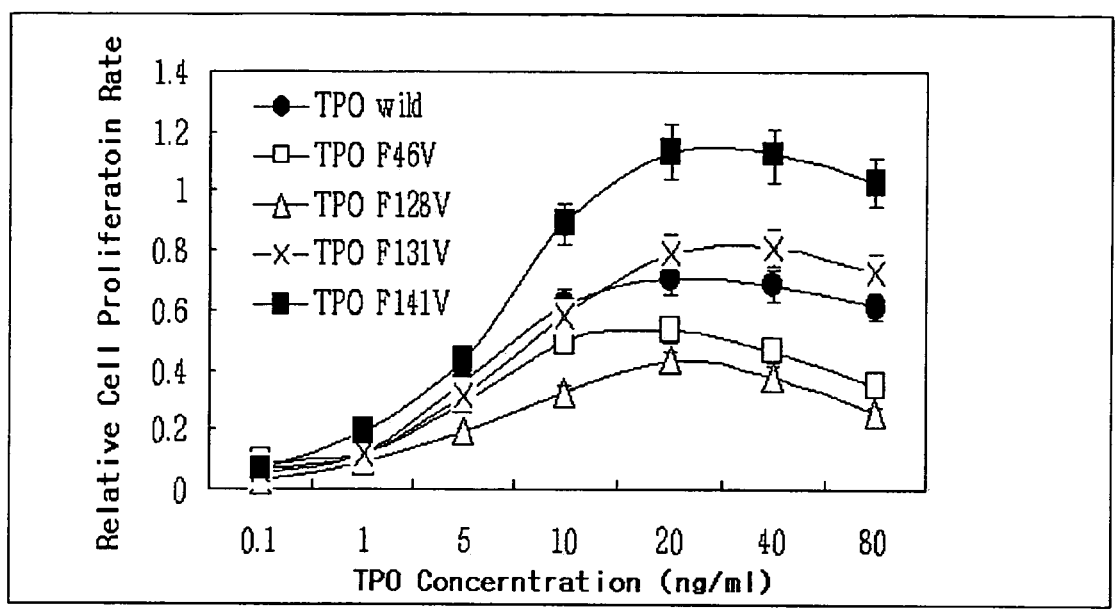
FIG. 7A is a graph showing the proliferation rates of TF-1/c-Mp1 cells according to the concentration of TPO variants according to the present invention.

FIG. 7a showed differences of TPO wild type and muteins in stimulating TF-1/c-Mpl cell proliferation. TPO was applied to the TF-1/c-Mpl from 0.4 ng/ml to 75 ng/ml. Cell proliferation was increased up to 50 ng/ml of TPO concentration. TF-1/c-Mpl cell proliferation potential of TPO-[F141V] was much stronger than that of wild type and was the first in biological activity among TPO muteins. Biological activity of TPO-[F131V] was the second strongest among TPO muteins. Activity of TPO-[F46V] was similar to that of wild type.

B. Cell Proliferation Assay of EPO Muteins

Biological activity for EPO muteins was examined by cell proliferation assay using EPO-dependent TF-1 cell. Experimental procedure of cell proliferation assay of EPO muteins was similar to that of TPO muteins.

Figure 7B:
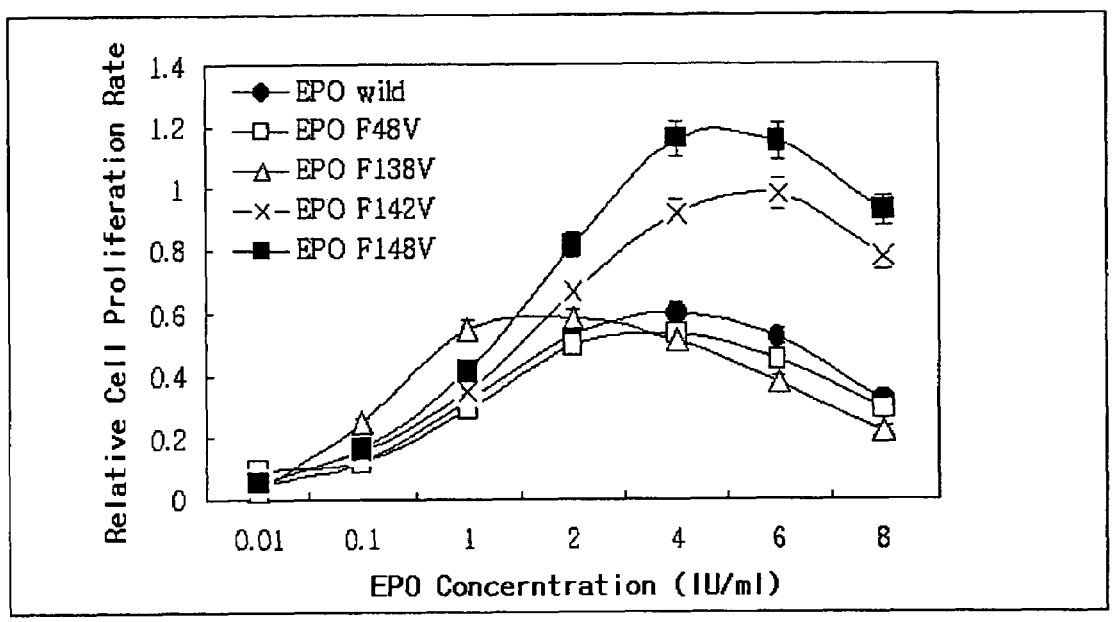
FIG. 7B is a graph showing the proliferation rates of TF-1 cells according to the concentration of EPO variants according to the present invention.

FIG. 7b showed differences of EPO wild type and muteins in stimulating TF-1 cell proliferation EPO was applied to the TF-1 Cell from 0.01 U/ml to 7 IU/ml. TF-1 cell proliferation potential of EPO-[F148V] was much stronger than that of the wild type and was the first in biological strength among EPO muteins. Biological activities of EPO-[F142V] and EPO-[F138V] were the second and the third strongest among EPO muteins, respectively.

TABLE 9

Biological activities of TPOs

| TPO | | The maximum activity comparision(%) |
|---|---|---|
| Wild type | | 100 |
| Muteins | TPO-[F46V] | 107 |
| | TPO-[F128V] | 63 |
| | TPO-[F131V] | 119 |
| | TPO-[F141V] | 146 |

TABLE 10

Biological activities of EPOs

| EPO | | The maximum activity comparision(%) |
|---|---|---|
| Wild type | | 100 |
| Muteins | EPO-[F48V] | 84 |
| | EPO-[F138V] | 57 |
| | EPO-[F142V] | 122 |
| | EPO-[F148V] | 137 |

C. G-CSF Muteins

Biological activity for G-CSF muteins was examined by cell proliferation assay using G-CSF dependent HL-60 cell. Experimental procedure of cell proliferation assay of G-CSF muteins was similar to that of TPO muteins.

Figure 7C:
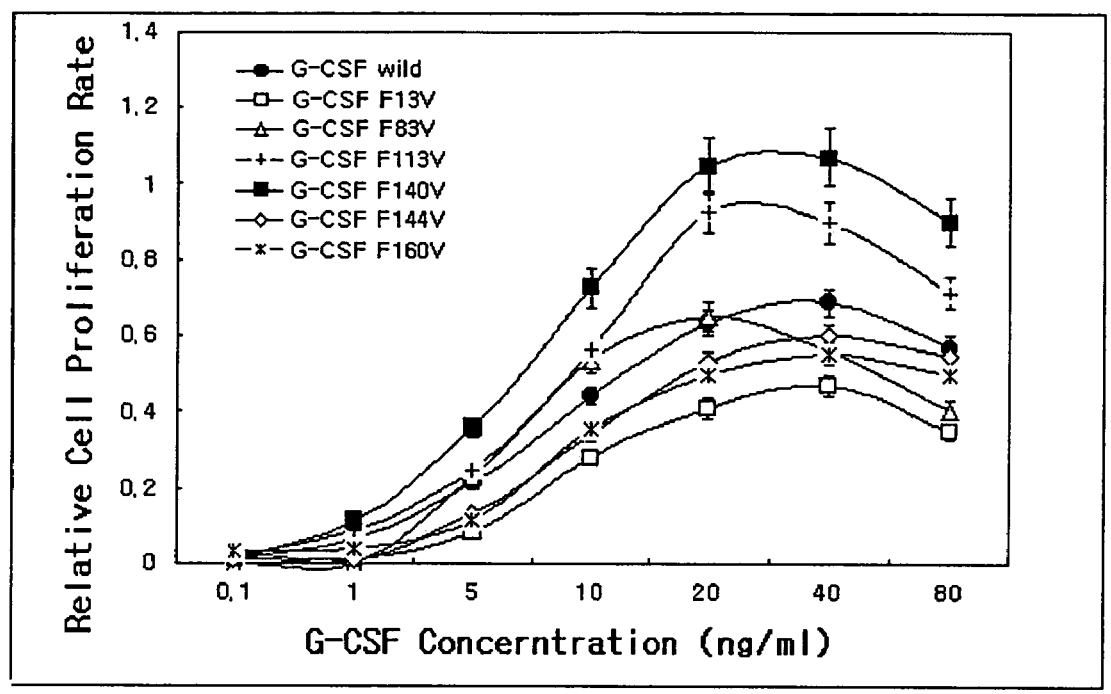
FIG. 7C is a graph showing the proliferation rates of HL60 cells according to the concentration of G-CSF variants according to the present invention.

FIG. 7c showed differences of G-CSF wild type and muteins in stimulating HL-60 cell proliferation G-CSF was applied to the HL-60 Cell from 0.4 ng/ml to 75 ng/ml. HL-60 cell proliferation potential of G-CSF-[F140V] was much stronger than that of the wild type and was the fist in biological strength among G-CSF muteins.

D. GH Muteins

Biological activity for GH muteins was examined by cell proliferation assay using GH dependent NB2 cell. Experimental procedure of cell proliferation assay of GH muteins was similar to that of GH muteins.

Figure 7D:
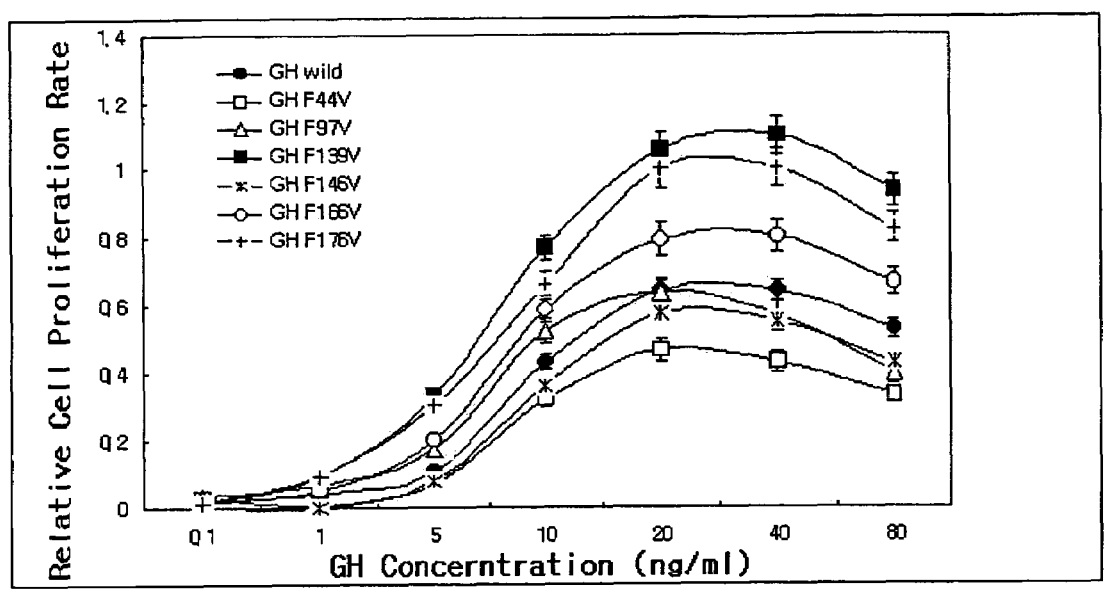
FIG. 7D is a graph showing the proliferation rates of Nb2 cells according to the concentration of GH variants according to the present invention.

FIG. 7d showed differences of GH wild type and muteins in stimulating NB2 cell proliferation. GH was applied to the NB2 Cell from 0.4 ng/ml to 75 ng/ml NB2 cell proliferation potential of GH-[F139V] was much stronger than that of the wild type and was the first in biological strength among GH muteins.

EXAMPLE 9

Pharmacokinetic Profiles of EPO- and TPO-Wild Types and Muteins

Difference of Pharmacokinetic profiles of each EPO- and TPO-muteins between their wildtype was investigated. TPO or TPO muteins was injected intravenously into rabbits (New Zealand White, 3 kg). And then blood samples were collected serially. EPO and TPO concentrations from each samples were detected by using quantitative ELISA assay as described above. Injection of EPOs into mice (12 weeks, Balb/c, 30 g) was performed by both intraperitonealy and intravenously. Blood samples in heparin-containing tubes were separated by centrifugation at 3,000 rpm for 10 minutes. Supernatant containing plasma was used to detect blood concentrations of EPO and TPO by using ELISA.

Figure 8A:
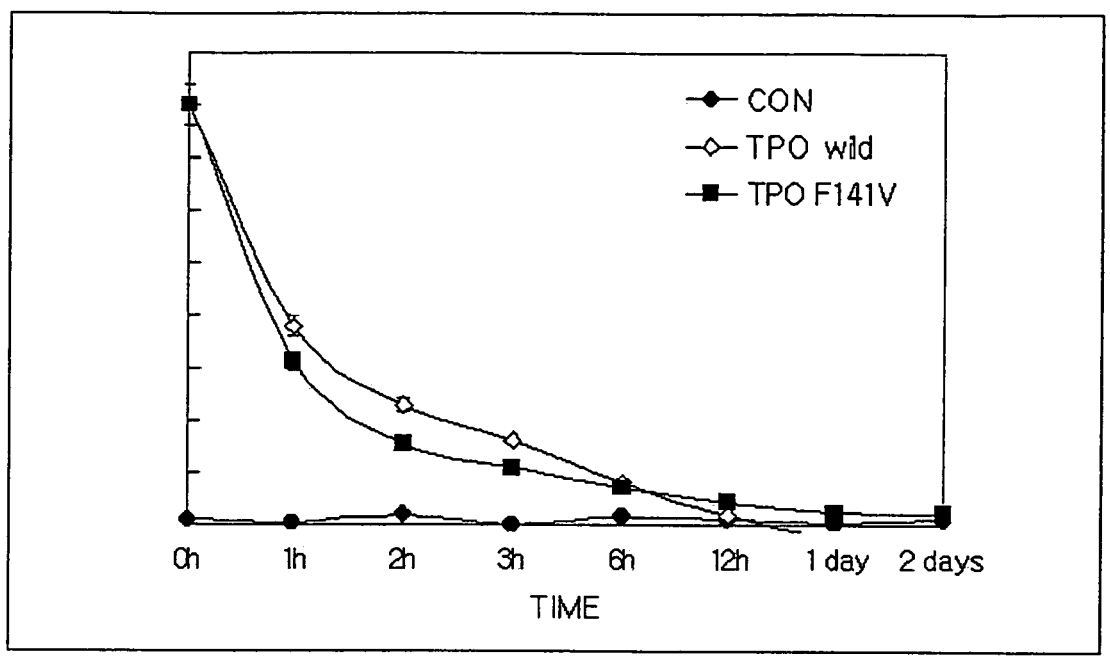
FIG. 8A is a graph showing the results of a pharmacokinetic assay of a TPO variant according to the present invention, in which the TPO variant was intravenously injected into rabbits, and serum levels of the TPO variant were measured.

After intravenous injection of 5 μg/kg of TPO wild type and -[F141V] into rabbit, plasma concentration profiles of TPO wild type and -[F141V] were shown in FIG. 8a. Concentration of TPO-[F141V] was decreased more rapidly thin that of wild type TPO. TPO-[F141V] was shifted from blood to peripheral target tissues more rapidly, due to its stronger binding affinity to receptor.

Figure 8B:
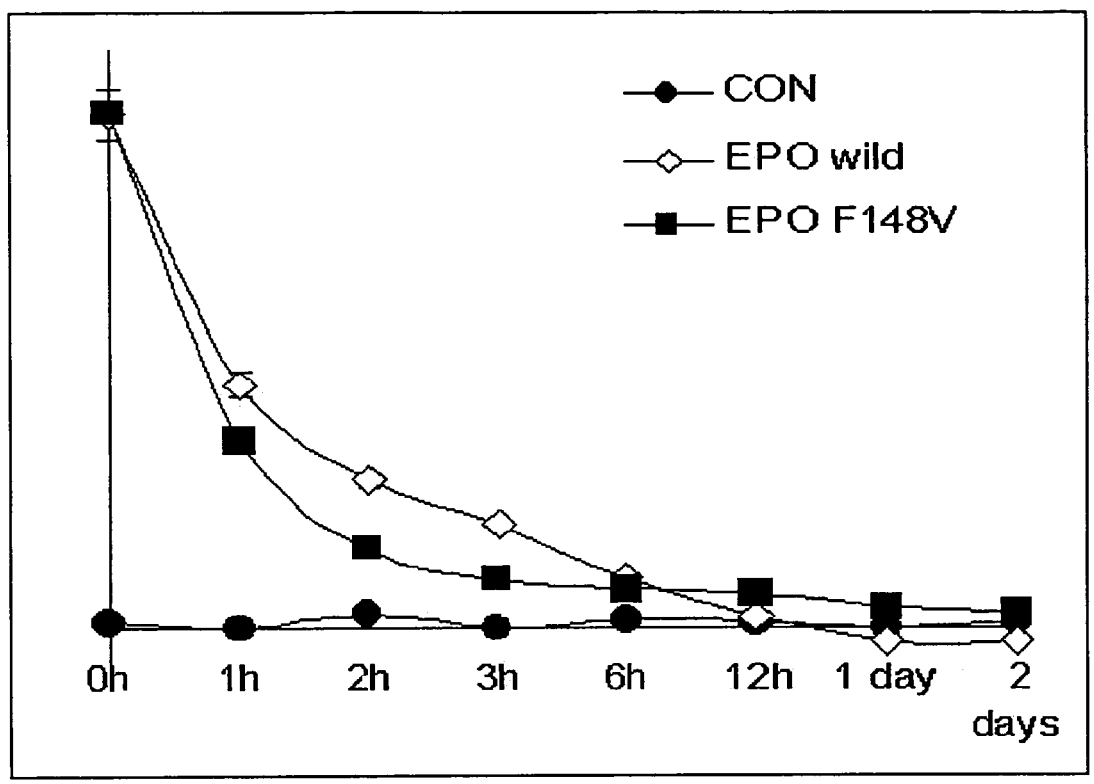
FIG. 8B is a graph showing the results of a pharmacokinetic assay of an EPO variant according to the present invention, in which the EPO variant was intravenously injected into rabbits, and serum levels of the EPO variant were measured.

After intravenous injection of 1000 I.U/kg of wild type EPO and EPO-[F148V] into rabbit, plasma concentration profiles of wild type EPO and EPO-[F148V] in blood were shown in FIG. 8b. Concentration of EPO-[F148V] was decreased more rapidly than that of EPO wild type.

Figure 8C:
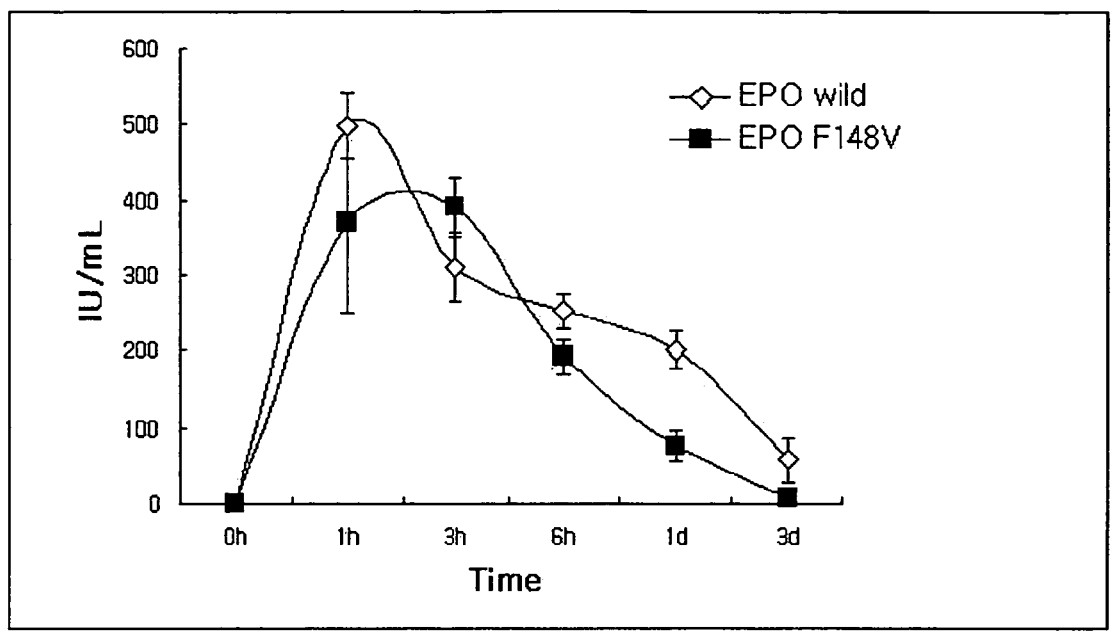
FIG. 8C is a graph showing the results of a pharmacokinetic assay of an EPO variant according to the present invention, in which the EPO variant was intraperitoneally injected into mice, and serum levels of the EPO variant were measured.

After intraperitoneal injection of 20 I.U/g of wild type EPO and EPO-[F148V] into mice, plasma concentration profiles were shown in FIG. 8c. The diffusion velocity of EPO wild type was higher than that of EPO-[F148V] at early stage and maximum concentration in blood (Cmax) of wild type EPO was also higher than that of EPO-[F148V]. Cmax of EPO-[F148V] remained longer than wild type EPO. These results suggested that EPO-[F148V] was more hydrophobic and had higher binding affinity to receptor than the wild type EPO. And these results lead to the conclusion that EPO-[F148V] was diffused into blood more slowly and shifted from blood to peripheral target tissues more quickly than those of wild type EPO.

TABLE 11

Pharmacokinetic parameters of EPO wild type and EPO-[F148V] mutein

| | Mouse | | Rabbit | |
|---|---|---|---|---|
| | Wild type EPO | EPO-mutein [F148V] | Wild type EPO | EPO-mutein [F148V] |
| $T_{1/2}$(Half life) | 1.9 | 1.4 | 3.8 | 2.4 |
| AUC | 100 | 78 | 100 | 80 |

EXAMPLE 10

In Vivo Activities of EPO Muteins

Difference of biological activities between EPO-wild type and muteins was verified in mice. Mice (12 weeks Balb/c, 20 g, Jungang Lab Animal Inc., Korea) were γ-irradiated at 700 Rad. 250 ng of purified EPO wild type and muteins in 50 μl of PBS were injected intraperitoneally 3 times everyday. Blood samples were collected from their tail vein. And then hematologic parameters were tested according to ordinary CBC test wild type EPO was used as a positive control and CHO cell culture supernatant was used as a negative control. Blood was collected into tubes containing EDTA at 0, 1st, 2nd, 4th, 7th, 10th, 15th, 20th, 25th, and 30th days after the injection.

FIG. 9 showed that CBC results in mice injected intraperitoneally with EPO-wild type and muteins to verify change in count of RBC and reticulocyte. Increase of RBC count (FIG. 9a) was much more remarkable in EPO[F148V]-injected mice than mice injected with wild type EPO. And the RBC increase of in EPO[F48V]- and EPO[138V]-injected mice was weaker than that of mice injected with wild type EPO. Increase of reticulocyte count (FIG. 9b) and hematocrit was similar to the result of RBC count change in mice injected with EPO-[F148V].

EXAMPLE 11

In vivo Activities of TPO Muteins

Difference of biological activities between TPO-wild type and muteins was studied in mice. Mice (12 weeks Balb/c, 20 g, Jungang Lab Animal Inc., Korea) were γ-irradiated at 700 Rad 250 ng of purified TPO wild type and muteins in 50 μl of PBS were injected intraperitoneally 3 times everyday. Blood samples were collected from their tail vein. And then hematologic parameters were tested according to ordinary CBC test. Wild type TPO was used as a positive control and CHO cell culture supernatant was used as a negative control. Blood was collected into tubes containing EDTA at 0, 1st, 4th, 7th, 10th, 14th, 18th 23rd, 28th, and 32nd days after injection.

FIG. 10 showed the changes of platelet count (FIG. 10a), leukocyte count (FIG. 10b), and neutrophil count (FIG. 10c) in mice injected intraperitoneally with TPO-wild type and muteins. Increase of platelet count was the most remarkable in mice injected with TPO-[F141V]. And mice injected with TPO-[F131V] was the second highest Mice injected with TPO-[F46V] was similar to those injected with wild type TPO. And mice injected with TPO-[128V] showed platelet count similar to that of negative controls injected with PBS (FIG. 10a). Increase of leukocyte count (FIG. 10b) and neutrophil count (FIG. 10c) showed similar patterns as those seen in platelet change.

INDUSTRIAL APPLICABILITY

As apparent from the above results of the present invention, valine substitution for phenylalanine residue, which is present in a domain participating in the binding of conventional wild-type biological response-modulating proteins to corresponding receptors, ligands or substrates, leads to an increase in binding affinity and biological activity, and reduces the production of autoantibodies to conventional protein variants, thereby making it possible to produce improved protein drugs.

The invention claimed is:

1. An isolated protein variant of thrombopoietin comprising an amino acid substitution of a valine residue for a phenylalanine residue in at least one of the phenylalanine amino acid residues at positions 46, 128 and 131 of SED ID NO.:25.

2. The isolated protein variant according to claim 1, wherein:
the thrombopoietin is altered by substituting a valine residue for a phenylalanine residue at position 131 of an amino acid sequence designed as SEQ ID NO.:25.

3. A pharmaceutical composition comprising the isolated protein variant of claim 1 and a pharmaceutically acceptable carrier.

4. A pharmaceutical composition comprising the isolated protein variant of claim 2 and a pharmaceutically acceptable carrier.

* * * * *

SEQUENCE LISTING

```
<160> NUMBER OF SEQ ID NOS: 65

<210> SEQ ID NO 1
<211> LENGTH: 200
<212> TYPE: PRT
<213> ORGANISM: Artificial Sequence
<220> FEATURE:
<223> OTHER INFORMATION: CNTF: 3rd, 83rd, 98th, 105th, 119th, 152nd or
      178th Phe is replaced by Val.

<400> SEQUENCE: 1

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140
```

```
Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
            165                 170                 175

Arg Phe Ile Ser Ser His Gln Thr Gly Ile Pro Ala Arg Gly Ser His
        180                 185                 190

Tyr Ile Ala Asn Asn Lys Lys Met
        195                 200

<210> SEQ ID NO 2
<211> LENGTH: 166
<212> TYPE: PRT
<213> ORGANISM: Artificial Sequence
<220> FEATURE:
<223> OTHER INFORMATION: EPO: 48th, 138th, 142nd or 148th Phe is
      replcaced by Val.

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Arg Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 209
<212> TYPE: PRT
<213> ORGANISM: Artificial Sequence
<220> FEATURE:
<223> OTHER INFORMATION: Flt3L: 6th, 15th, 81st, 87th, 96th or 124th Phe
      is replaced by Val.

<400> SEQUENCE: 3

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60
```

```
Gly Ser Lys Met Gln Gly Leu Leu Glu Arg Val Asn Thr Glu Ile His
 65                  70                  75                  80

Phe Val Thr Lys Cys Ala Phe Gln Pro Pro Ser Cys Leu Arg Phe
                 85                  90                  95

Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
                115                 120                 125

Glu Leu Gln Cys Gln Pro Asp Ser Ser Thr Leu Pro Pro Pro Trp Ser
            130                 135                 140

Pro Arg Pro Leu Glu Ala Thr Ala Pro Thr Ala Pro Gln Pro Pro Leu
145                 150                 155                 160

Leu Leu Leu Leu Leu Pro Val Gly Leu Leu Leu Leu Ala Ala Ala
                165                 170                 175

Trp Cys Leu His Trp Gln Arg Thr Arg Arg Thr Pro Arg Pro Gly
            180                 185                 190

Glu Gln Val Pro Pro Val Pro Ser Pro Gln Asp Leu Leu Leu Val Glu
            195                 200                 205

His

<210> SEQ ID NO 4
<211> LENGTH: 174
<212> TYPE: PRT
<213> ORGANISM: Artificial Sequence
<220> FEATURE:
<223> OTHER INFORMATION: G-CSF: 13rd, 83rd, 113rd, 140th, 144th or 160th
      Phe is replaced by Val.

<400> SEQUENCE: 4

Thr Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
                 20                  25                  30

Glu Lys Leu Cys Ala Thr Tyr Lys Leu Cys His Pro Glu Glu Leu Val
             35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 5
<211> LENGTH: 127
<212> TYPE: PRT
<213> ORGANISM: Artificial Sequence
<220> FEATURE:
```

<223> OTHER INFORMATION: GM-CSF: 47th, 103rd, 106th, 113rd or 119th Phe is replaced by Val.

<400> SEQUENCE: 5

```
Ala Pro Ala Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
             20                  25                  30

Ala Ala Glu Met Asn Glu Thr Val Glu Val Ile Ser Glu Met Phe Asp
         35                  40                  45

Leu Gln Glu Pro Thr Cys Leu Gln Thr Arg Leu Glu Leu Tyr Lys Gln
 50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
             85                  90                  95

Ala Thr Gln Ile Ile Thr Phe Glu Ser Phe Lys Glu Asn Leu Lys Asp
        100                 105                 110

Phe Leu Leu Val Ile Pro Phe Asp Cys Trp Glu Pro Val Gln Glu
    115                 120                 125
```

<210> SEQ ID NO 6
<211> LENGTH: 191
<212> TYPE: PRT
<213> ORGANISM: Artificial Sequence
<220> FEATURE:
<223> OTHER INFORMATION: GH: 1st, 10th, 25th, 31st, 44th, 54th, 92th, 97th, 139th, 146th, 166th, 176th or 191st Phe is replaced by Val.

<400> SEQUENCE: 6

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
             20                  25                  30

Glu Ala Tyr Ile Pro Lys Glu Gln Lys Tyr Ser Phe Leu Gln Asn Pro
         35                  40                  45

Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
             85                  90                  95

Phe Ala Asn Ser Leu Val Tyr Gly Ala Ser Asp Ser Asn Val Tyr Asp
        100                 105                 110

Leu Leu Lys Asp Leu Glu Glu Gly Ile Gln Thr Leu Met Gly Arg Leu
    115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 7
<211> LENGTH: 165

```
<212> TYPE: PRT
<213> ORGANISM: Artificial Sequence
<220> FEATURE:
<223> OTHER INFORMATION: IFN-alpha 2A: 27th, 36th, 38th, 43rd, 47th,
      64th, 67th, 84th, 123rd or 151st Phe is replaced by Val.

<400> SEQUENCE: 7

Cys Asp Leu Pro Gln Thr His Ser Leu Gly Ser Arg Arg Thr Leu Met
 1               5                  10                  15

Leu Leu Ala Gln Met Arg Lys Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 8
<211> LENGTH: 165
<212> TYPE: PRT
<213> ORGANISM: Artificial Sequence
<220> FEATURE:
<223> OTHER INFORMATION: IFN-alpha 2B: 27th, 36th, 38th, 43rd, 47th,
      64th, 67th, 84th, 123rd or 151st Phe is replaced by Val.

<400> SEQUENCE: 8

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140
```

```
Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 9
<211> LENGTH: 166
<212> TYPE: PRT
<213> ORGANISM: Artificial Sequence
<220> FEATURE:
<223> OTHER INFORMATION: IFN-Beta: 8th, 38th, 50th, 67th, 70th, 111st or
      154th Phe is replaced by Val.

<400> SEQUENCE: 9

Met Ser Tyr Asn Leu Leu Gly Phe Leu Gln Arg Ser Ser Asn Cys Gln
1               5                   10                  15

Cys Gln Lys Leu Leu Trp Gln Leu Asn Gly Arg Leu Glu Tyr Cys Leu
            20                  25                  30

Lys Asp Arg Arg Asn Phe Asp Ile Pro Glu Glu Ile Lys Gln Leu Gln
        35                  40                  45

Gln Phe Gln Lys Glu Asp Ala Ala Val Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Arg Asn
                85                  90                  95

His Leu Lys Thr Val Leu Glu Glu Lys Leu Glu Lys Glu Asp Phe Thr
            100                 105                 110

Arg Gly Lys Arg Met Ser Ser Leu His Leu Lys Arg Tyr Tyr Gly Arg
        115                 120                 125

Ile Leu His Tyr Leu Lys Ala Lys Glu Asp Ser His Cys Ala Trp Thr
    130                 135                 140

Ile Val Arg Val Glu Ile Leu Arg Asn Phe Tyr Val Ile Asn Arg Leu
145                 150                 155                 160

Thr Gly Tyr Leu Arg Asn
                165

<210> SEQ ID NO 10
<211> LENGTH: 146
<212> TYPE: PRT
<213> ORGANISM: Artificial Sequence
<220> FEATURE:
<223> OTHER INFORMATION: IFN-gamma: 18th, 32nd, 55th, 57th, 60th, 63rd,
      84th, 85th, 95th or 139th Phe is replaced by Val.

<400> SEQUENCE: 10

Cys Tyr Cys Gln Asp Pro Tyr Val Lys Glu Ala Glu Asn Leu Lys Lys
1               5                   10                  15

Tyr Phe Asn Ala Gly His Ser Asp Val Ala Asp Asn Gly Thr Leu Phe
            20                  25                  30

Leu Gly Ile Leu Lys Asn Trp Lys Glu Glu Ser Asp Arg Lys Ile Met
        35                  40                  45

Gln Ser Gln Ile Val Ser Phe Tyr Phe Lys Leu Phe Lys Asn Phe Lys
    50                  55                  60

Asp Asp Gln Ser Ile Gln Lys Ser Val Glu Thr Ile Lys Glu Asp Met
65                  70                  75                  80

Asn Val Lys Phe Phe Asn Ser Asn Lys Lys Arg Asp Asp Phe Glu
                85                  90                  95
```

-continued

```
Lys Leu Thr Asn Tyr Ser Val Thr Asp Leu Asn Val Gln Arg Lys Ala
            100                 105                 110

Ile His Glu Leu Ile Gln Val Met Ala Glu Leu Ser Pro Ala Ala Lys
        115                 120                 125

Thr Gly Lys Arg Lys Arg Ser Gln Met Leu Phe Gln Gly Arg Arg Ala
    130                 135                 140

Ser Gln
145

<210> SEQ ID NO 11
<211> LENGTH: 172
<212> TYPE: PRT
<213> ORGANISM: Artificial Sequence
<220> FEATURE:
<223> OTHER INFORMATION: IFN-omega: 27th, 36th, 38th, 65th, 68th, 124th
      or 153rd Phe is replaced by Val.

<400> SEQUENCE: 11

Cys Asp Leu Pro Gln Asn His Gly Leu Leu Ser Arg Asn Thr Leu Val
 1               5                  10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170

<210> SEQ ID NO 12
<211> LENGTH: 187
<212> TYPE: PRT
<213> ORGANISM: Artificial Sequence
<220> FEATURE:
<223> OTHER INFORMATION: IFN-tau: 8th, 39th, 68th, 71st, 88th, 127th,
      156th, 157th, 159th or 183rd Phe is replaced by Val.

<400> SEQUENCE: 12

Leu Asp Leu Lys Leu Ile Ile Phe Gln Gln Arg Gln Val Asn Gln Glu
 1               5                  10                  15

Ser Leu Lys Leu Leu Asn Lys Leu Gln Thr Leu Ser Ile Gln Gln Cys
            20                  25                  30

Leu Pro His Arg Lys Asn Phe Leu Leu Pro Gln Lys Ser Leu Ser Pro
        35                  40                  45

Gln Gln Tyr Gln Lys Gly His Thr Leu Ala Ile Leu His Glu Met Leu
    50                  55                  60
```

```
Gln Gln Ile Phe Ser Leu Phe Arg Ala Asn Ile Ser Leu Asp Gly Trp
 65                  70                  75                  80

Glu Glu Asn His Thr Glu Lys Phe Leu Ile Gln Leu His Gln Gln Leu
             85                  90                  95

Glu Tyr Leu Glu Ala Leu Met Gly Leu Glu Ala Glu Lys Leu Ser Gly
        100                 105                 110

Thr Leu Gly Ser Asp Asn Leu Arg Leu Gln Val Lys Met Tyr Phe Arg
    115                 120                 125

Arg Ile His Asp Tyr Leu Glu Asn Gln Asp Tyr Ser Thr Cys Ala Trp
130                 135                 140

Ala Ile Val Gln Val Glu Ile Ser Arg Cys Leu Phe Phe Val Phe Ser
145                 150                 155                 160

Leu Thr Glu Lys Leu Ser Lys Gln Gly Arg Pro Leu Asn Asp Met Lys
                165                 170                 175

Gln Glu Leu Thr Thr Glu Phe Arg Ser Pro Arg
            180                 185

<210> SEQ ID NO 13
<211> LENGTH: 133
<212> TYPE: PRT
<213> ORGANISM: Artificial Sequence
<220> FEATURE:
<223> OTHER INFORMATION: IL-2: 42nd, 44th, 78th, 103rd, 117th or 124th
      Phe is replaced by Val.

<400> SEQUENCE: 13

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 14
<211> LENGTH: 133
<212> TYPE: PRT
<213> ORGANISM: Artificial Sequence
<220> FEATURE:
<223> OTHER INFORMATION: IL-3: 37th, 61st, 107th, 113rd or 133rd Phe is
      replaced by Val.

<400> SEQUENCE: 14

Ala Pro Met Thr Gln Thr Thr Pro Leu Lys Thr Ser Trp Val Asn Cys
  1               5                  10                  15

Ser Asn Met Ile Asp Glu Ile Ile Thr His Leu Lys Gln Pro Pro Leu
             20                  25                  30
```

-continued

```
Pro Leu Leu Asp Phe Asn Asn Leu Asn Gly Glu Asp Gln Asp Ile Leu
        35                  40                  45

Met Glu Asn Asn Leu Arg Arg Pro Asn Leu Glu Ala Phe Asn Arg Ala
    50                  55                  60

Val Lys Ser Leu Gln Asn Ala Ser Ala Ile Glu Ser Ile Leu Lys Asn
65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
            100                 105                 110

Phe Tyr Leu Lys Thr Leu Glu Asn Ala Gln Ala Gln Gln Thr Thr Leu
        115                 120                 125

Ser Leu Ala Ile Phe
    130

<210> SEQ ID NO 15
<211> LENGTH: 129
<212> TYPE: PRT
<213> ORGANISM: Artificial Sequence
<220> FEATURE:
<223> OTHER INFORMATION: IL-4: 33rd, 45th, 55th, 73rd, 82nd or 112nd Phe
      is replaced by Val.

<400> SEQUENCE: 15

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 16
<211> LENGTH: 115
<212> TYPE: PRT
<213> ORGANISM: Artificial Sequence
<220> FEATURE:
<223> OTHER INFORMATION: IL-5: 49th, 69th, 96th or 103rd Phe is replaced
      by Val.

<400> SEQUENCE: 16

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
```

```
                50                  55                  60
Val Glu Arg Leu Phe Lys Asn Leu Ser Leu Ile Lys Lys Tyr Ile Asp
 65                  70                  75                  80

Gly Gln Lys Lys Cys Gly Glu Arg Arg Val Asn Gln Phe
                 85                  90                  95

Leu Asp Tyr Leu Gln Glu Phe Leu Gly Val Met Asn Thr Glu Trp Ile
                100                 105                 110

Ile Glu Ser
        115

<210> SEQ ID NO 17
<211> LENGTH: 183
<212> TYPE: PRT
<213> ORGANISM: Artificial Sequence
<220> FEATURE:
<223> OTHER INFORMATION: IL-6: 73rd, 77th, 93rd, 104th, 124th, 169th or
      172nd Phe is replaced by Val.

<400> SEQUENCE: 17

Val Pro Pro Gly Glu Asp Ser Lys Asp Val Ala Ala Pro His Arg Gln
  1               5                  10                  15

Pro Leu Thr Ser Ser Glu Arg Ile Asp Lys Gln Ile Arg Tyr Ile Leu
                 20                  25                  30

Asp Gly Ile Ser Ala Leu Arg Lys Glu Thr Cys Asn Lys Ser Asn Met
             35                  40                  45

Cys Glu Ser Ser Lys Glu Ala Leu Ala Glu Asn Asn Leu Asn Leu Pro
 50                  55                  60

Lys Met Ala Glu Lys Asp Gly Cys Phe Gln Ser Gly Phe Asn Glu Glu
 65                  70                  75                  80

Thr Cys Leu Val Lys Ile Ile Thr Gly Leu Leu Glu Phe Glu Val Tyr
                 85                  90                  95

Leu Glu Tyr Leu Gln Asn Arg Phe Glu Ser Ser Glu Glu Gln Ala Arg
                100                 105                 110

Ala Val Gln Met Ser Thr Lys Val Leu Ile Gln Phe Leu Gln Lys Lys
            115                 120                 125

Ala Lys Asn Leu Asp Ala Ile Thr Thr Pro Asp Pro Thr Thr Asn Ala
130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180

<210> SEQ ID NO 18
<211> LENGTH: 197
<212> TYPE: PRT
<213> ORGANISM: Artificial Sequence
<220> FEATURE:
<223> OTHER INFORMATION: IL-12p35: 13rd, 39th, 82nd, 96th, 116th, 132nd,
      150th, 166th or 180th Phe is replaced by Val.

<400> SEQUENCE: 18

Arg Asn Leu Pro Val Ala Thr Pro Asp Pro Gly Met Phe Pro Cys Leu
  1               5                  10                  15

His His Ser Gln Asn Leu Leu Arg Ala Val Ser Asn Met Leu Gln Lys
                 20                  25                  30

Ala Arg Gln Thr Leu Glu Phe Tyr Pro Cys Thr Ser Glu Glu Ile Asp
```

-continued

His Glu Asp Ile Thr Lys Asp Lys Thr Ser Thr Val Glu Ala Cys Leu
          50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
            195

<210> SEQ ID NO 19
<211> LENGTH: 146
<212> TYPE: PRT
<213> ORGANISM: Artificial Sequence
<220> FEATURE:
<223> OTHER INFORMATION: LPT: 41st or 92nd Phe is replaced by Val.

<400> SEQUENCE: 19

Val Pro Ile Gln Lys Val Gln Asp Asp Thr Lys Thr Leu Ile Lys Thr
  1               5                  10                  15

Ile Val Thr Arg Ile Asn Asp Ile Ser His Thr Gln Ser Val Ser Ser
                 20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
                 85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 20
<211> LENGTH: 180
<212> TYPE: PRT
<213> ORGANISM: Artificial Sequence
<220> FEATURE:
<223> OTHER INFORMATION: LIF: 41st, 52nd, 67th, 70th, 156th or 180th Phe is replaced by Val.

<400> SEQUENCE: 20

```
Ser Pro Leu Pro Ile Thr Pro Val Asn Ala Thr Cys Ala Ile Arg His
 1               5                  10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Ala Lys Leu
65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Ile Ile Ala Val Leu
                165                 170                 175

Ala Gln Ala Phe
            180
```

<210> SEQ ID NO 21
<211> LENGTH: 522
<212> TYPE: PRT
<213> ORGANISM: Artificial Sequence
<220> FEATURE:
<223> OTHER INFORMATION: M-CSF: 35th, 37th, 54th, 67th, 91st, 106th,
      121st, 135th, 143rd, 229th, 255th, 311st, 439th, 466th or 485th
      Phe is replaced by Val.

<400> SEQUENCE: 21

```
Glu Glu Val Ser Glu Tyr Cys Ser His Met Ile Gly Ser Gly His Leu
 1               5                  10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140
```

```
Glu Cys Ser Ser Gln Asp Val Val Thr Lys Pro Asp Cys Asn Cys Leu
145                 150                 155                 160

Tyr Pro Lys Ala Ile Pro Ser Asp Pro Ala Ser Val Ser Pro His
            165                 170                 175

Gln Pro Leu Ala Pro Ser Met Ala Pro Val Ala Gly Leu Thr Trp Glu
            180                 185                 190

Asp Ser Glu Gly Thr Glu Gly Ser Ser Leu Leu Pro Gly Glu Gln Pro
            195                 200                 205

Leu His Thr Val Asp Pro Gly Ser Ala Lys Gln Arg Pro Pro Arg Ser
210                 215                 220

Thr Cys Gln Ser Phe Glu Pro Pro Glu Thr Pro Val Val Lys Asp Ser
225                 230                 235                 240

Thr Ile Gly Gly Ser Pro Gln Pro Arg Pro Ser Val Gly Ala Phe Asn
                245                 250                 255

Pro Gly Met Glu Asp Ile Leu Asp Ser Ala Met Gly Thr Asn Trp Val
            260                 265                 270

Pro Glu Glu Ala Ser Gly Glu Ala Ser Glu Ile Pro Val Pro Gln Gly
            275                 280                 285

Thr Glu Leu Ser Pro Ser Arg Pro Gly Gly Gly Ser Met Gln Thr Glu
            290                 295                 300

Pro Ala Arg Pro Ser Asn Phe Leu Ser Ala Ser Ser Pro Leu Pro Ala
305                 310                 315                 320

Ser Ala Lys Gly Gln Gln Pro Ala Asp Val Thr Gly Thr Ala Leu Pro
                325                 330                 335

Arg Val Gly Pro Val Arg Pro Thr Gly Gln Asp Trp Asn His Thr Pro
            340                 345                 350

Gln Lys Thr Asp His Pro Ser Ala Leu Leu Arg Asp Pro Pro Glu Pro
            355                 360                 365

Gly Ser Pro Arg Ile Ser Ser Leu Arg Pro Gln Gly Leu Ser Asn Pro
            370                 375                 380

Ser Thr Leu Ser Ala Gln Pro Gln Leu Ser Arg Ser His Ser Ser Gly
385                 390                 395                 400

Ser Val Leu Pro Leu Gly Glu Leu Glu Gly Arg Arg Ser Thr Arg Asp
                405                 410                 415

Arg Arg Ser Pro Ala Glu Pro Glu Gly Gly Pro Ala Ser Glu Gly Ala
            420                 425                 430

Ala Arg Pro Leu Pro Arg Phe Asn Ser Val Pro Leu Thr Asp Thr Gly
            435                 440                 445

His Glu Arg Gln Ser Glu Gly Ser Ser Ser Pro Gln Leu Gln Glu Ser
            450                 455                 460

Val Phe His Leu Leu Val Pro Ser Val Ile Leu Val Leu Leu Ala Val
465                 470                 475                 480

Gly Gly Leu Leu Phe Tyr Arg Trp Arg Arg Ser His Gln Glu Pro
                485                 490                 495

Gln Arg Ala Asp Ser Pro Leu Glu Gln Pro Glu Gly Ser Pro Leu Thr
            500                 505                 510

Gln Asp Asp Arg Gln Val Glu Leu Pro Val
            515                 520

<210> SEQ ID NO 22
<211> LENGTH: 227
<212> TYPE: PRT
<213> ORGANISM: Artificial Sequence
<220> FEATURE:
<223> OTHER INFORMATION: OSM: 56th, 70th, 160th, 169th, 176th or 184th
```

-continued

Phe is replaced by Val.

<400> SEQUENCE: 22

Ala Ala Ile Gly Ser Cys Ser Lys Glu Tyr Arg Val Leu Leu Gly Gln
1               5                   10                  15

Leu Gln Lys Gln Thr Asp Leu Met Gln Asp Thr Ser Arg Leu Leu Asp
            20                  25                  30

Pro Tyr Ile Arg Ile Gln Gly Leu Asp Val Pro Lys Leu Arg Glu His
        35                  40                  45

Cys Arg Glu Arg Pro Gly Ala Phe Pro Ser Glu Glu Thr Leu Arg Gly
    50                  55                  60

Leu Gly Arg Arg Gly Phe Leu Gln Thr Leu Asn Ala Thr Leu Gly Cys
65                  70                  75                  80

Val Leu His Arg Leu Ala Asp Leu Glu Gln Arg Leu Pro Lys Ala Gln
                85                  90                  95

Asp Leu Glu Arg Ser Gly Leu Asn Ile Glu Asp Leu Glu Lys Leu Gln
            100                 105                 110

Met Ala Arg Pro Asn Ile Leu Gly Leu Arg Asn Asn Ile Tyr Cys Met
        115                 120                 125

Ala Gln Leu Leu Asp Asn Ser Asp Thr Ala Glu Pro Thr Lys Ala Gly
    130                 135                 140

Arg Gly Ala Ser Gln Pro Pro Thr Pro Thr Pro Ala Ser Asp Ala Phe
145                 150                 155                 160

Gln Arg Lys Leu Glu Gly Cys Arg Phe Leu His Gly Tyr His Arg Phe
                165                 170                 175

Met His Ser Val Gly Arg Val Phe Ser Lys Trp Gly Glu Ser Pro Asn
            180                 185                 190

Arg Ser Arg Arg His Ser Pro His Gln Ala Leu Arg Lys Gly Val Arg
        195                 200                 205

Arg Thr Arg Pro Ser Arg Lys Gly Lys Arg Leu Met Thr Arg Gly Gln
    210                 215                 220

Leu Pro Arg
225

<210> SEQ ID NO 23
<211> LENGTH: 191
<212> TYPE: PRT
<213> ORGANISM: Artificial Sequence
<220> FEATURE:
<223> OTHER INFORMATION: PL: 10th, 31st, 44th, 52nd, 54th, 92nd, 97th,
    146th, 166th, 176th or 191st Phe is replaced by Val.

<400> SEQUENCE: 23

Val Gln Thr Val Pro Leu Ser Arg Leu Phe Asp His Ala Met Leu Gln
1               5                   10                  15

Ala His Arg Ala His Gln Leu Ala Ile Asp Thr Tyr Gln Glu Phe Glu
            20                  25                  30

Glu Thr Tyr Ile Pro Lys Asp Gln Lys Tyr Ser Phe Leu His Asp Ser
        35                  40                  45

Gln Thr Ser Phe Cys Phe Ser Asp Ser Ile Pro Thr Pro Ser Asn Met
    50                  55                  60

Glu Glu Thr Gln Gln Lys Ser Asn Leu Glu Leu Leu Arg Ile Ser Leu
65                  70                  75                  80

Leu Leu Ile Glu Ser Trp Leu Glu Pro Val Arg Phe Leu Arg Ser Met
                85                  90                  95

Phe Ala Asn Asn Leu Val Tyr Asp Thr Ser Asp Ser Asp Asp Tyr His

```
                100             105             110
Leu Leu Lys Asp Leu Glu Glu Gly Ile Gln Thr Leu Met Gly Arg Leu
            115                 120                 125

Glu Asp Gly Ser Arg Arg Thr Gly Gln Ile Leu Lys Gln Thr Tyr Ser
        130                 135                 140

Lys Phe Asp Thr Asn Ser His Asn His Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Met Val Gln Cys Arg Ser Val Glu Gly Ser Cys Gly Phe
            180                 185                 190

<210> SEQ ID NO 24
<211> LENGTH: 248
<212> TYPE: PRT
<213> ORGANISM: Artificial Sequence
<220> FEATURE:
<223> OTHER INFORMATION: SCF: 63rd, 102nd, 110th, 115th, 116th, 119th,
      126th, 129th, 158th, 199th, 205th, 207th or 245th Phe is replaced
      by Val.

<400> SEQUENCE: 24

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser Ser Thr Leu
130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
            180                 185                 190

Met Ala Leu Pro Ala Leu Phe Ser Leu Ile Ile Gly Phe Ala Phe Gly
        195                 200                 205

Ala Leu Tyr Trp Lys Lys Arg Gln Pro Ser Leu Thr Arg Ala Val Glu
    210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245

<210> SEQ ID NO 25
```

-continued

```
<211> LENGTH: 332
<212> TYPE: PRT
<213> ORGANISM: Artificial Sequence
<220> FEATURE:
<223> OTHER INFORMATION: TPO: 46th, 128th, 131st, 141st, 186th, 204th,
      240th or 286th Phe is replaced by Val.

<400> SEQUENCE: 25

Ser Pro Ala Pro Ala Cys Asp Leu Arg Val Leu Ser Lys Leu Leu
  1               5                  10                  15

Arg Asp Ser His Val Leu His Ser Arg Leu Ser Gln Cys Pro Glu Val
             20                  25                  30

His Pro Leu Pro Thr Pro Val Leu Leu Pro Ala Val Asp Phe Ser Leu
         35                  40                  45

Gly Glu Trp Lys Thr Gln Met Glu Glu Thr Lys Ala Gln Asp Ile Leu
     50                  55                  60

Gly Ala Val Thr Leu Leu Leu Glu Gly Val Met Ala Ala Arg Gly Gln
 65                  70                  75                  80

Leu Gly Pro Thr Cys Leu Ser Ser Leu Leu Gly Gln Leu Ser Gly Gln
                 85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu Pro Asn
                165                 170                 175

Arg Thr Ser Gly Leu Leu Glu Thr Asn Phe Thr Ala Ser Ala Arg Thr
            180                 185                 190

Thr Gly Ser Gly Leu Leu Lys Trp Gln Gln Gly Phe Arg Ala Lys Ile
        195                 200                 205

Pro Gly Leu Leu Asn Gln Thr Ser Arg Ser Leu Asp Gln Ile Pro Gly
    210                 215                 220

Tyr Leu Asn Arg Ile His Glu Leu Leu Asn Gly Thr Arg Gly Leu Phe
225                 230                 235                 240

Pro Gly Pro Ser Arg Arg Thr Leu Gly Ala Pro Asp Ile Ser Ser Gly
                245                 250                 255

Thr Ser Asp Thr Gly Ser Leu Pro Pro Asn Leu Gln Pro Gly Tyr Ser
            260                 265                 270

Pro Ser Pro Thr His Pro Pro Thr Gly Gln Tyr Thr Leu Phe Pro Leu
        275                 280                 285

Pro Pro Thr Leu Pro Thr Pro Val Val Gln Leu His Pro Leu Leu Pro
    290                 295                 300

Asp Pro Ser Ala Pro Thr Pro Thr Pro Thr Ser Pro Leu Leu Asn Thr
305                 310                 315                 320

Ser Tyr Thr His Ser Gln Asn Leu Ser Gln Glu Gly
                325                 330

<210> SEQ ID NO 26
<211> LENGTH: 28
<212> TYPE: DNA
<213> ORGANISM: Artificial Sequence
<220> FEATURE:
<223> OTHER INFORMATION: primer 1
```

<400> SEQUENCE: 26
cggaattccg atggagctga ctgaattg                                28

<210> SEQ ID NO 27
<211> LENGTH: 30
<212> TYPE: DNA
<213> ORGANISM: Artificial Sequence
<220> FEATURE:
<223> OTHER INFORMATION: primer 2

<400> SEQUENCE: 27
tttagcggcc gcattcttac ccttcctgag                              30

<210> SEQ ID NO 28
<211> LENGTH: 21
<212> TYPE: DNA
<213> ORGANISM: Artificial Sequence
<220> FEATURE:
<223> OTHER INFORMATION: primer 4

<400> SEQUENCE: 28
ccaagctaac gtccacagca g                                       21

<210> SEQ ID NO 29
<211> LENGTH: 17
<212> TYPE: DNA
<213> ORGANISM: Artificial Sequence
<220> FEATURE:
<223> OTHER INFORMATION: primer 6

<400> SEQUENCE: 29
gctcaggacg atggcat                                            17

<210> SEQ ID NO 30
<211> LENGTH: 23
<212> TYPE: DNA
<213> ORGANISM: Artificial Sequence
<220> FEATURE:
<223> OTHER INFORMATION: primer 8

<400> SEQUENCE: 30
ggtgttggac gctcaggaag atg                                     23

<210> SEQ ID NO 31
<211> LENGTH: 21
<212> TYPE: DNA
<213> ORGANISM: Artificial Sequence
<220> FEATURE:
<223> OTHER INFORMATION: primer 10

<400> SEQUENCE: 31
catcaggaca cgcacctttc c                                       21

<210> SEQ ID NO 32
<211> LENGTH: 17
<212> TYPE: DNA
<213> ORGANISM: Artificial Sequence
<220> FEATURE:
<223> OTHER INFORMATION: primer 11

<400> SEQUENCE: 32
ggcgcggaga tgggggt                                            17

<210> SEQ ID NO 33

```
<211> LENGTH: 22
<212> TYPE: DNA
<213> ORGANISM: Artificial Sequence
<220> FEATURE:
<223> OTHER INFORMATION: primer 12

<400> SEQUENCE: 33
tggtcatctg tccctgtcc tg                                           22

<210> SEQ ID NO 34
<211> LENGTH: 24
<212> TYPE: DNA
<213> ORGANISM: Artificial Sequence
<220> FEATURE:
<223> OTHER INFORMATION: primer 14

<400> SEQUENCE: 34
gacattaact ttggtgtctg ggac                                        24

<210> SEQ ID NO 35
<211> LENGTH: 21
<212> TYPE: DNA
<213> ORGANISM: Artificial Sequence
<220> FEATURE:
<223> OTHER INFORMATION: primer 15

<400> SEQUENCE: 35
ctgtccgcaa actcttccga g                                           21

<210> SEQ ID NO 36
<211> LENGTH: 22
<212> TYPE: DNA
<213> ORGANISM: Artificial Sequence
<220> FEATURE:
<223> OTHER INFORMATION: primer 17

<400> SEQUENCE: 36
cgcaaactcg tccgagtcta ct                                          22

<210> SEQ ID NO 37
<211> LENGTH: 22
<212> TYPE: DNA
<213> ORGANISM: Artificial Sequence
<220> FEATURE:
<223> OTHER INFORMATION: primer 19

<400> SEQUENCE: 37
gagtctactc caatgtggtg gg                                          22

<210> SEQ ID NO 38
<211> LENGTH: 31
<212> TYPE: DNA
<213> ORGANISM: Artificial Sequence
<220> FEATURE:
<223> OTHER INFORMATION: primer 21

<400> SEQUENCE: 38
ccccgggacc atggctggac ctgccaccca g                                31

<210> SEQ ID NO 39
<211> LENGTH: 27
<212> TYPE: DNA
<213> ORGANISM: Artificial Sequence
<220> FEATURE:
<223> OTHER INFORMATION: primer 22

<400> SEQUENCE: 39
```

-continued

```
cgaattcgct cagggctggg caaggag                                    27

<210> SEQ ID NO 40
<211> LENGTH: 18
<212> TYPE: DNA
<213> ORGANISM: Artificial Sequence
<220> FEATURE:
<223> OTHER INFORMATION: primer 24

<400> SEQUENCE: 40
acttgagcag gacgctct                                              18

<210> SEQ ID NO 41
<211> LENGTH: 17
<212> TYPE: DNA
<213> ORGANISM: Artificial Sequence
<220> FEATURE:
<223> OTHER INFORMATION: primer 25

<400> SEQUENCE: 41
agcggccttg tcctcta                                               17

<210> SEQ ID NO 42
<211> LENGTH: 17
<212> TYPE: DNA
<213> ORGANISM: Artificial Sequence
<220> FEATURE:
<223> OTHER INFORMATION: primer 27

<400> SEQUENCE: 42
gacgttgcca ccaccat                                               17

<210> SEQ ID NO 43
<211> LENGTH: 17
<212> TYPE: DNA
<213> ORGANISM: Artificial Sequence
<220> FEATURE:
<223> OTHER INFORMATION: primer 29

<400> SEQUENCE: 43
gccgtcgcct ctgcttt                                               17

<210> SEQ ID NO 44
<211> LENGTH: 18
<212> TYPE: DNA
<213> ORGANISM: Artificial Sequence
<220> FEATURE:
<223> OTHER INFORMATION: primer 31

<400> SEQUENCE: 44
tcgccttctg ctgtccag                                              18

<210> SEQ ID NO 45
<211> LENGTH: 17
<212> TYPE: DNA
<213> ORGANISM: Artificial Sequence
<220> FEATURE:
<223> OTHER INFORMATION: primer 33

<400> SEQUENCE: 45
tctgcaagac gtcctgg                                               17

<210> SEQ ID NO 46
<211> LENGTH: 64
<212> TYPE: DNA
```

```
<213> ORGANISM: Artificial Sequence
<220> FEATURE:
<223> OTHER INFORMATION: primer 35

<400> SEQUENCE: 46
cttttggcct gctctgcctg tcctggcttc aagagggcag tgccttccca accattccct      60
tatc                                                                  64

<210> SEQ ID NO 47
<211> LENGTH: 60
<212> TYPE: DNA
<213> ORGANISM: Artificial Sequence
<220> FEATURE:
<223> OTHER INFORMATION: primer 37

<400> SEQUENCE: 47
ggaattcatg gctgcaggct cccggacgtc cctgctcctg gcttttggcc tgctctgcct      60

<210> SEQ ID NO 48
<211> LENGTH: 25
<212> TYPE: DNA
<213> ORGANISM: Artificial Sequence
<220> FEATURE:
<223> OTHER INFORMATION: primer 40

<400> SEQUENCE: 48
ggggttctgc aggactgaat acttc                                           25

<210> SEQ ID NO 49
<211> LENGTH: 20
<212> TYPE: DNA
<213> ORGANISM: Artificial Sequence
<220> FEATURE:
<223> OTHER INFORMATION: primer 42

<400> SEQUENCE: 49
ggctgttggc gacgatcctg                                                 20

<210> SEQ ID NO 50
<211> LENGTH: 26
<212> TYPE: DNA
<213> ORGANISM: Artificial Sequence
<220> FEATURE:
<223> OTHER INFORMATION: primer 44

<400> SEQUENCE: 50
gtaggtctgc ttgacgatct gcccag                                          26

<210> SEQ ID NO 51
<211> LENGTH: 24
<212> TYPE: DNA
<213> ORGANISM: Artificial Sequence
<220> FEATURE:
<223> OTHER INFORMATION: primer 46

<400> SEQUENCE: 51
gagtttgtgt cgaccttgct gtag                                            24

<210> SEQ ID NO 52
<211> LENGTH: 24
<212> TYPE: DNA
<213> ORGANISM: Artificial Sequence
<220> FEATURE:
<223> OTHER INFORMATION: primer 48

<400> SEQUENCE: 52
```

-continued gtccttcctg acgcagtaga gcag                                                   24

<210> SEQ ID NO 53
<211> LENGTH: 28
<212> TYPE: DNA
<213> ORGANISM: Artificial Sequence
<220> FEATURE:
<223> OTHER INFORMATION: primer 50

<400> SEQUENCE: 53
cgatgcgcag gactgtctcg accttgtc                                               28

<210> SEQ ID NO 54
<211> LENGTH: 26
<212> TYPE: DNA
<213> ORGANISM: Artificial Sequence
<220> FEATURE:
<223> OTHER INFORMATION: primer 51

<400> SEQUENCE: 54
cggaattcat ggaccacctc ggggcg                                                 26

<210> SEQ ID NO 55
<211> LENGTH: 32
<212> TYPE: DNA
<213> ORGANISM: Artificial Sequence
<220> FEATURE:
<223> OTHER INFORMATION: primer 52

<400> SEQUENCE: 55
gctctagact aagagcaagc cacatagctg gg                                          32

<210> SEQ ID NO 56
<211> LENGTH: 33
<212> TYPE: DNA
<213> ORGANISM: Artificial Sequence
<220> FEATURE:
<223> OTHER INFORMATION: primer 53

<400> SEQUENCE: 56
cccaagctta tggagctgac tgaattgctc ctc                                         33

<210> SEQ ID NO 57
<211> LENGTH: 32
<212> TYPE: DNA
<213> ORGANISM: Artificial Sequence
<220> FEATURE:
<223> OTHER INFORMATION: primer 54

<400> SEQUENCE: 57
ggaattctta cccttcctga gacagattct gg                                          32

<210> SEQ ID NO 58
<211> LENGTH: 34
<212> TYPE: DNA
<213> ORGANISM: Artificial Sequence
<220> FEATURE:
<223> OTHER INFORMATION: primer 55

<400> SEQUENCE: 58
gctctagagc tcatttaccc ggagacaggg agag                                        34

<210> SEQ ID NO 59
<211> LENGTH: 28
<212> TYPE: DNA

<213> ORGANISM: Artificial Sequence
<220> FEATURE:
<223> OTHER INFORMATION: primer 56

<400> SEQUENCE: 59
cccaagctta tggctggacc tgccaccc                                      28

<210> SEQ ID NO 60
<211> LENGTH: 29
<212> TYPE: DNA
<213> ORGANISM: Artificial Sequence
<220> FEATURE:
<223> OTHER INFORMATION: primer 57

<400> SEQUENCE: 60
ggaattcgca acagagccag gcagttcca                                     29

<210> SEQ ID NO 61
<211> LENGTH: 26
<212> TYPE: DNA
<213> ORGANISM: Artificial Sequence
<220> FEATURE:
<223> OTHER INFORMATION: primer 58

<400> SEQUENCE: 61
cggaattcat ggatctctgg cagctg                                        26

<210> SEQ ID NO 62
<211> LENGTH: 28
<212> TYPE: DNA
<213> ORGANISM: Artificial Sequence
<220> FEATURE:
<223> OTHER INFORMATION: primer 59

<400> SEQUENCE: 62
ggactagttt ggctcatctg aggaagtg                                      28

<210> SEQ ID NO 63
<211> LENGTH: 35
<212> TYPE: DNA
<213> ORGANISM: Artificial Sequence
<220> FEATURE:
<223> OTHER INFORMATION: primer 60

<400> SEQUENCE: 63
ggaattcgca gagcccaaat cttgtgacaa aactc                              35

<210> SEQ ID NO 64
<211> LENGTH: 27
<212> TYPE: DNA
<213> ORGANISM: Artificial Sequence
<220> FEATURE:
<223> OTHER INFORMATION: primer 61

<400> SEQUENCE: 64
gactagtgca gagcccaaat cttgtga                                       27

<210> SEQ ID NO 65
<211> LENGTH: 34
<212> TYPE: DNA
<213> ORGANISM: Artificial Sequence -continued

```
<220> FEATURE:
<223> OTHER INFORMATION: primer 62

<400> SEQUENCE: 65
gctctagagc tcatttaccc ggagacaggg agag                              34
```